(12) United States Patent
Kobussen et al.

(10) Patent No.: US 11,793,731 B2
(45) Date of Patent: Oct. 24, 2023

(54) MULTI-PART DENTAL COMPOSITION HAVING STAGED VISCOSITY PRIOR TO HARDENING

(71) Applicant: 3M INNOVATIVE PROPERTIES COMPANY, St. Paul, MN (US)

(72) Inventors: Gregory A. Kobussen, Woodbury, MN (US); Ahmed S. Abuelyaman, Woodbury, MN (US); Paul J. Homnick, Lake Elmo, MN (US); Bradley D. Craig, Lake Elmo, MN (US); Ying Lin, Woodbury, MN (US); Hassan Sahouani, Hastings, MN (US); Chuntao Cao, Woodbury, MN (US); William H. Moser, Edina, MN (US); Kolby L. White, Woodbury, MN (US); Joseph D. Rule, Woodbury, MN (US); Joachim Zech, Kaufering (DE)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 448 days.

(21) Appl. No.: 16/954,726

(22) PCT Filed: Dec. 19, 2018

(86) PCT No.: PCT/IB2018/060371
§ 371 (c)(1),
(2) Date: Jun. 17, 2020

(87) PCT Pub. No.: WO2019/123333
PCT Pub. Date: Jun. 27, 2019

(65) Prior Publication Data
US 2020/0383877 A1   Dec. 10, 2020

Related U.S. Application Data

(60) Provisional application No. 62/607,636, filed on Dec. 19, 2017.

(51) Int. Cl.
*A61K 6/30* (2020.01)
*A61K 6/77* (2020.01)
(Continued)

(52) U.S. Cl.
CPC .................. *A61K 6/30* (2020.01); *A61K 6/62* (2020.01); *A61K 6/76* (2020.01); *A61K 6/77* (2020.01);
(Continued)

(58) Field of Classification Search
CPC combination set(s) only.
See application file for complete search history.

(56) References Cited

U.S. PATENT DOCUMENTS 3,218,305 A * 11/1965 Krieble .................. C09J 4/00
526/89
4,167,618 A  9/1979 Schmitt
(Continued)

FOREIGN PATENT DOCUMENTS

DE  20121446  10/2002
EP  0463862  1/1992
(Continued)

OTHER PUBLICATIONS

Konuray, "Sequential curing of amine-acrylate-methacrylate mixtures based on selective aza-Michael addition followed by radical photopolymenzation", European Polymer Journal, Nov. 2016, vol. 84, pp. 256-267, XP29832435.
(Continued)

*Primary Examiner* — Peter A Salamon
(74) *Attorney, Agent, or Firm* — 3M Innovative Properties Company

(57) ABSTRACT

Disclosed herein are non-aqueous compositions including: a flowable Part A including at least one resin and Reactant A; and a flowable Part B including at least one resin and
(Continued)

Reactant B; wherein at least one of flowable Part A and flowable Part B further includes a free radically polymerizable resin; wherein at least one of flowable Part A and flowable Part B further includes a free radical initiator system; wherein flowable Part A and flowable Part B are capable of being mixed to provide a flowable mixed composition; wherein when flowable Part A and flowable Part B are mixed, Reactant A and Reactant B are capable of interacting to cause a non-free radical reaction within a first staging time to provide a first staged stable consistency for the mixed composition; wherein Reactant A comprises an acid and Reactant B comprises a base, and upon mixing flowable Part A and flowable Part B, the Reactant A acid is capable of reacting with the Reactant B base in an ionic acid-base reaction; and wherein the mixed composition having the first staged stable consistency is capable of forming a hardened dental composition upon initiation of free radical polymerization.

20 Claims, 1 Drawing Sheet

(51) Int. Cl.

| | | |
|---|---|---|
| *A61K 6/887* | (2020.01) | |
| *A61K 6/76* | (2020.01) | |
| *A61K 6/62* | (2020.01) | |
| *C08K 3/22* | (2006.01) | |
| *C08K 3/40* | (2006.01) | |
| *C08K 9/06* | (2006.01) | |
| *C08L 33/10* | (2006.01) | |
| *C08L 33/14* | (2006.01) | |

(52) U.S. Cl.
CPC ............... *A61K 6/887* (2020.01); *C08K 3/22* (2013.01); *C08K 3/40* (2013.01); *C08K 9/06* (2013.01); *C08L 33/10* (2013.01); *C08L 33/14* (2013.01)

(56) References Cited

U.S. PATENT DOCUMENTS

| | | | | |
|---|---|---|---|---|
| 4,180,640 A * | 12/1979 | Melody | ...................... | C09J 5/04 |
| | | | | 156/332 |
| 4,287,330 A * | 9/1981 | Rich | ......................... | C09J 4/00 |
| | | | | 523/176 |
| 4,321,349 A * | 3/1982 | Rich | ......................... | C09J 4/00 |
| | | | | 526/321 |
| 4,468,202 A | 8/1984 | Cohen | | |
| 4,503,161 A | 3/1985 | Korbel | | |
| 4,503,169 A | 3/1985 | Randklev | | |
| 4,642,126 A | 2/1987 | Zador | | |
| 4,652,274 A | 3/1987 | Boettcher | | |
| 4,695,251 A | 9/1987 | Randklev | | |
| 5,154,762 A | 10/1992 | Mitra | | |
| 5,501,727 A | 3/1996 | Wang | | |
| 5,545,676 A | 8/1996 | Palazzotto | | |
| 5,918,772 A | 7/1999 | Keller | | |
| 5,944,419 A | 8/1999 | Streiff | | |
| 6,187,836 B1 | 2/2001 | Oxman | | |
| 6,383,279 B1 | 5/2002 | Eckhardt | | |
| 6,460,464 B1 * | 10/2002 | Attarwala | ................ | F42B 5/36 |
| | | | | 102/470 |
| 6,506,816 B1 | 1/2003 | Ario | | |
| 6,572,693 B1 | 6/2003 | Wu | | |
| 6,624,211 B2 | 9/2003 | Karim | | |
| 6,632,908 B1 * | 10/2003 | Maandi | ............... | C08F 290/062 |
| | | | | 526/236 |
| 6,676,795 B1 * | 1/2004 | Levandoski | ........... | C09J 175/16 |
| | | | | 101/167 |
| 6,730,156 B1 | 5/2004 | Windisch | | |
| 6,899,948 B2 | 5/2005 | Zhang | | |
| 6,939,900 B2 | 9/2005 | Ario | | |
| 6,982,288 B2 | 1/2006 | Mitra | | |
| 7,173,074 B2 | 2/2007 | Mitra | | |
| 7,429,422 B2 | 9/2008 | Davidson | | |
| 7,674,850 B2 | 3/2010 | Karim | | |
| 7,816,423 B2 | 10/2010 | Karim | | |
| 8,501,834 B2 | 8/2013 | Maletz | | |
| 8,822,564 B2 | 9/2014 | Drechsler | | |
| 10,729,622 B2 | 8/2020 | Maurer et al. | | |
| 2003/0153726 A1 | 8/2003 | Eckhardt | | |
| 2004/0069175 A1 * | 4/2004 | Attarwala | ................. | F42B 5/36 |
| | | | | 102/438 |
| 2004/0077746 A1 * | 4/2004 | Takeshita | ................. | A61K 6/77 |
| | | | | 523/116 |
| 2004/0122126 A1 | 6/2004 | Wu | | |
| 2006/0187752 A1 | 8/2006 | Keller | | |
| 2007/0090079 A1 | 4/2007 | Keller | | |
| 2009/0048364 A1 | 2/2009 | Liu | | |
| 2009/0208909 A1 | 8/2009 | Rusin | | |
| 2011/0249922 A1 * | 10/2011 | Tsuchiya | ................ | C09J 175/16 |
| | | | | 384/41 |
| 2013/0277890 A1 | 10/2013 | Bowman | | |
| 2015/0257984 A1 | 9/2015 | Shchori | | |
| 2016/0369040 A1 * | 12/2016 | Das | .......... | C08L 63/00 |
| 2020/0383877 A1 * | 12/2020 | Kobussen | ................ | A61K 6/30 |
| 2022/0298498 A1 * | 9/2022 | Nishida | .................... | C12N 1/20 |

FOREIGN PATENT DOCUMENTS

| | | |
|---|---|---|
| EP | 2022464 | 2/2009 |
| EP | 2526921 | 11/2012 |
| JP | 04235109 | 8/1992 |
| JP | 2011-116695 | 6/2011 |
| JP | 2011116695 A * | 6/2011 |
| WO | WO2001-30307 | 5/2001 |
| WO | WO2002-058641 | 8/2002 |
| WO | WO2005-016783 | 2/2005 |
| WO | WO2006-020760 | 2/2006 |
| WO | WO2007-104037 | 9/2007 |
| WO | WO2009-061884 | 5/2009 |
| WO | WO2010-123800 | 10/2010 |
| WO | WO2011-133495 | 10/2011 |
| WO | WO2012-177985 | 12/2012 |
| WO | WO2016-130673 | 8/2016 |
| WO | WO2016-196028 | 12/2016 |
| WO | WO 2016-202744 | 12/2016 |
| WO | WO 2017-015193 | 1/2017 |
| WO | WO 2017-093206 | 6/2017 |
| WO | WO 2017-178383 | 10/2017 |
| WO | WO 2018-057335 | 3/2018 |

OTHER PUBLICATIONS

Macosko, "Rheology Principles, Measurements, and Applications", 92 (1994).
Wang, "Thiol-Michael addition miniemulsion polymerizations: functional nanoparticles and reactive latex films", Polymer Chemistry, 2015, vol. 6, No. 20, pp. 3758-3763.
International Search Report for PCT International Application No. PCT/IB2018/060269, dated Jul. 26, 2019, 9 pages.
International Search Report for PCT International Application No. PCT/IB2018/060371, dated Jun. 6, 2019, 7 pages.

* cited by examiner

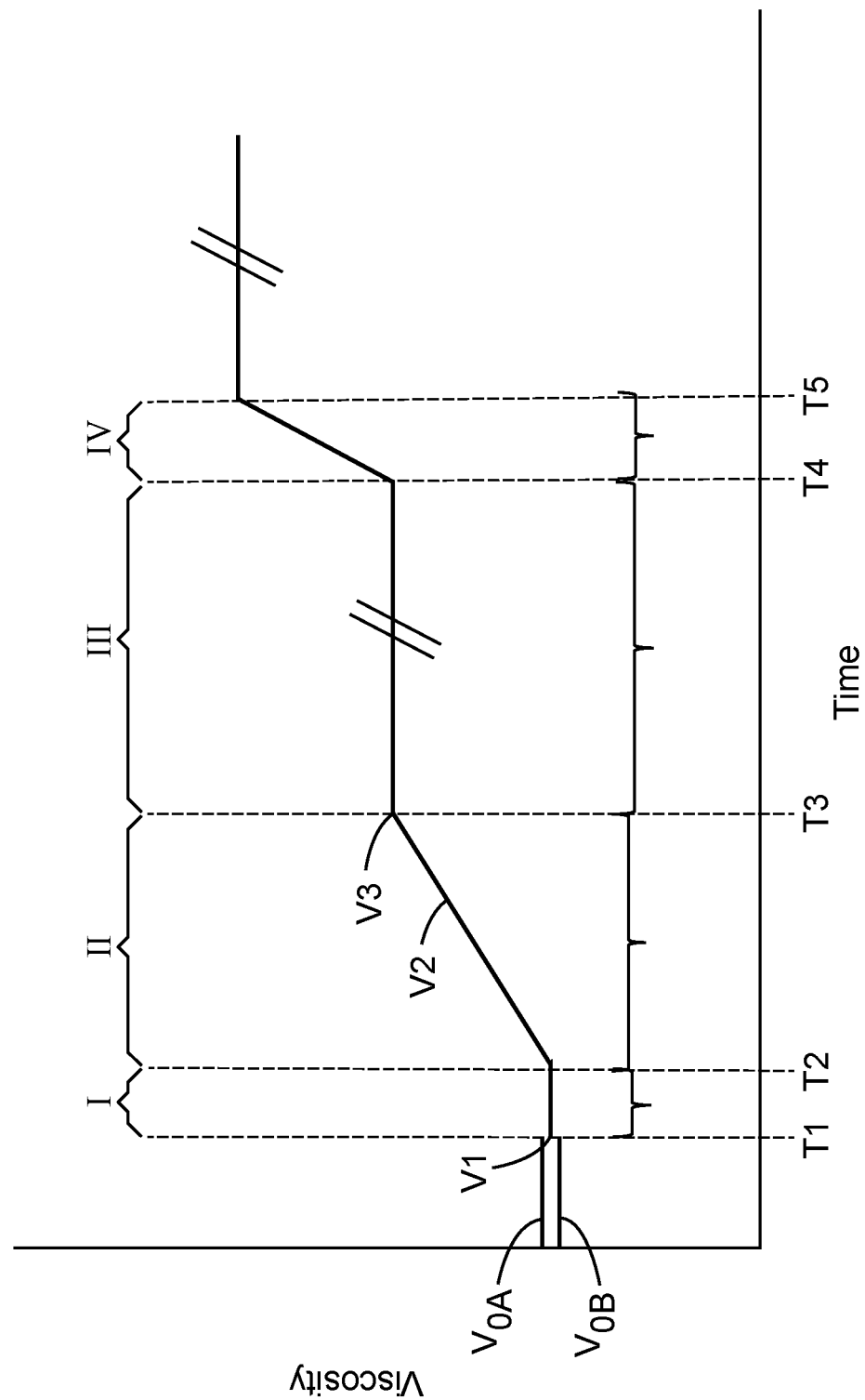

MULTI-PART DENTAL COMPOSITION HAVING STAGED VISCOSITY PRIOR TO HARDENING

CROSS REFERENCE TO RELATED APPLICATIONS

This application is a national stage filing under 35 U.S.C. 371 of PCT/IB2018/060371, filed 19 Dec. 2018, which claims the benefit of U.S. Provisional Application No. 62/607,636, filed 19 Dec. 2017, the disclosures of each of which are incorporated by reference herein in their entireties.

BACKGROUND

Since introduced more than half a century ago, resin-based dental composites have become popular dental restorative materials due, for example, to their tooth-colored aesthetics, high strength, and ease of use. Dental resin composites are commonly categorized based on viscosity into either universal composites or flowable composites Universal composites have paste-like viscosity. They have higher viscosity and are thick and packable. Flowable composites have lower viscosity and are thinner and able to flow with minimal force. Flowable composites are typically delivered through a needle tip. Both classes of composites are used in dental clinics because of their unique features.

Flowable composites are easy to use. They flow into the prepped cavities, have good adaptation, and a smaller chance of trapping air bubbles. However, flowable composites are runny and sticky, making it difficult to shape occlusal surfaces prior to hardening.

Universal composites have different properties than flowable composites. Universal composites are non-sticky and packable. Dentists regularly sculpt and shape universal composites to make occlusal surfaces and interproximal walls. However, universal composites need to be packed into place, which requires more effort from dentists to ensue good adaptation, and to avoid trapping air in the cavities.

Consequently, a dental practitioner can choose a flowable composite that will flow and adapt, but cannot be shaped prior to cure. Alternatively, a dental practitioner can choose a universal composite that can be shaped, but will only adapt after manipulation by the dentist (e.g., packing in place with a hand instrument).

There is a continuing need for dental composite materials with improved handling properties.

SUMMARY

A dental practitioner restoring a tooth has needs for materials that can adapt or conform to the shape of the cavity, such as relatively low viscosity materials that can flow into undercuts or other complex geometries of the cavity. The dental practitioner restoring the tooth also has a desire for materials that are shapeable so that the practitioner can sculpt the natural anatomy of the tooth prior to curing. Shaping the restorative prior to curing can save time by reducing or eliminating the need to cut and shape the restoration after cure with a hand piece.

Since both flowable composites and universal composites are used extensively, and each has features that dental practitioners like, a single composite that has properties of both a flowable composite and a universal composite would be desirable. For example, a single composite that behaves like a flowable composite during application (i.e., flowing into cavity with great adaption not trapping air) and behaves like a universal composite after application (e.g., packable and contourable, sculptable, or shapable) would be desirable. For example, a composite that has the capability of changing its viscosity from flowable to packable could meet the desired needs.

Disclosed herein are direct dental restorative materials that can flow and adapt to the cavity like a flowable composite, that undergo a transition in viscosity (i.e., "staging") that allows them to be sculpted and shaped, after which they can be hardened to full restorative properties.

In one aspect, the present disclosure provides a non-aqueous composition including: a flowable Part A including at least one resin and Reactant A; and a flowable Part B including at least one resin and Reactant B; wherein at least one of flowable Part A and flowable Part B further includes a free radically polymerizable resin; wherein at least one of flowable Part A and flowable Part B further includes a free radical initiator system; wherein flowable Part A and flowable Part B are capable of being mixed to provide a flowable mixed composition; wherein when flowable Part A and flowable Part B are mixed, Reactant A and Reactant B are capable of interacting to cause a non-free radical reaction within a first staging time to provide a first staged stable consistency for the mixed composition that is lower than the arithmetic mean of the consistency of flowable Part A and the consistency of flowable Part B; wherein Reactant A includes an acid and Reactant B includes a base, and upon mixing flowable Part A and flowable Part B, the Reactant A acid is capable of reacting with the Reactant B base in an ionic acid-base reaction; and wherein the mixed composition having the first staged stable consistency is capable of fonning a hardened dental composition upon initiation of free radical polymerization. In certain embodiments, flowable Part A is a paste, flowable Part B is a paste, and/or flowable Part A and flowable Part B are both pastes.

In another aspect, the present disclosure provides a method of preparing a composition having a first staged stable consistency.

In one embodiment, the method includes: providing a non-aqueous composition as described herein; mixing flowable Part A and flowable Part B to provide a mixed composition; and allowing the consistency of the mixed composition to decrease to a first staged stable consistency that is lower than the arithmetic mean of the consistency of flowable Part A and the consistency of flowable Part B.

In another embodiment, the method includes providing a non-aqueous composition as described herein; mixing flowable Part A and flowable Part B to provide a mixed composition; allowing the consistency of the mixed composition to decrease to a first staged stable consistency that is lower than the arithmetic mean of the consistency of flowable Part A and the consistency of flowable Part B; and subjecting the mixed composition having the first staged stable consistency to conditions sufficient to initiate free radical polymerization to provide the hardened dental composition.

In another aspect, the present disclosure provides a device for storing a non-aqueous composition as described herein. In one embodiment, the device includes: a first compartment containing flowable Part A; and a second compartment containing flowable Part B.

In another aspect, the present disclosure provides a method of preparing a composition having a first staged stable consistency.

In one embodiment, the method includes: providing a device as described herein; combining flowable Part A and flowable Part B to provide a mixed composition; and allowing the consistency of the mixed composition to decrease to a first staged stable consistency that is lower than the arithmetic mean of the consistency of flowable Part A and the consistency of flowable Part B.

In another embodiment, the method includes: providing a device as described herein; combining flowable Part A and flowable Part B to provide a mixed composition; allowing the consistency of the mixed composition to decrease to a first staged stable consistency that is lower than the arithmetic mean of the consistency of flowable Part A and the consistency of flowable Part B; and subjecting the mixed composition having the first staged stable consistency to conditions sufficient to initiate free radical polymerization to provide the hardened dental composition.

In some embodiments, the non-aqueous compositions disclosed herein can advantageously offer improved handling properties for the dental practitioner. For example, the non-aqueous compositions can be quickly placed and adapted and also easily shaped, properties that can result in a simple process for timely and efficient completion of the restoration. Simple processes that lead to timely and efficient completion of the restoration can reduce the risk of contamination and increase the probability of successful clinical outcomes.

As used herein, the term "compound" or "component" is a chemical substance which has a particular molecular identity or is made of a mixture of such substances, e.g., polymeric substances.

As used herein, unless otherwise noted, the term "consistency" refers to a definite, and measurable quantity according the "consistency test" described in the Example section. Consistency value of a material is not the same as viscosity. In fact, consistency varies in a relatively inverse direction compared to viscosity. In other words, a relatively lower consistency value corresponds to a more viscous or thicker material; a relatively higher consistency value corresponds to a lower viscosity.

As used herein, a "dental composition" or a "composition for dental use" or a "composition to be used in the dental field" or a "dental restorative material" or a "dental restorative" refers to any composition that can be used in the dental field. By "dental composition" is meant an unfilled or filled (e.g. a composite) material (e.g., a dental or orthodontic material) that are capable of being applied or adhered to an oral surface. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives (e.g., a restorative filling material), liners, sealants (e.g., orthodontic sealants), and coatings. Oftentimes a dental composition can be used to bond a dental article to a tooth structure. By "hardenable dental composition" is meant a dental composition, such as a paste, that can be hardened to form a dental article.

By "dental article" is meant an article that can be adhered (e.g., bonded) to an oral surface (e.g., a tooth structure). Typically, the dental article is a restored dentition or a portion thereof. Examples include restoratives, replacements, inlays, onlays, veneers, full and partial crowns, bridges, implants, implant abutments, copings, anterior fillings, posterior fillings, cavity liners, sealants, dentures, posts, bridge frameworks and other bridge structures, abutments, orthodontic appliances and devices, and prostheses (e.g., partial or full dentures).

As used herein, the terms "dental composition" and "dental article" are not limited to compositions and articles used in dental applications, but also include orthodontic compositions (e.g., orthodontic adhesives) and orthodontic devices (e.g., orthodontic appliances such as retainers, night guards, brackets, buccal tubes, bands, cleats, buttons, lingual retainers, bite openers, positioners, and the like), respectively.

By "oral surface" is meant a soft or hard surface in the oral environment. Hard surfaces typically include tooth structure including, for example, natural and artificial tooth surfaces, bone, tooth models, dentin, enamel, cementum, and the like.

Dental compositions are typically hardenable compositions that can be hardened at ambient conditions, including a temperature range from about 15 to 50° C. or from about 20 to 40° C. within a time frame of about 30 minutes or 20 minutes or 10 minutes. Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges.

As used herein, a "polymerizable component" refers to any component that can be cured or solidified, for example, by heating to cause polymerization or chemical crosslinking.

As used herein, the term "resin" refers to a polymerizable component that contains one, two, three, or more polymerizable groups. Exemplary polymerizable groups include, but are not limited to, unsaturated organic groups, such as vinyl groups such as found in a (methyl)acrylate group. A resin can often be cured by radiation induced polymerization or crosslinking, or by using a redox initiator.

As used herein, the term "monomer" refers to any chemical substance that can be characterized by a chemical formula, bearing polymerizable groups (e.g., (meth)acrylate groups) that can be polymerized to oligomers or polymers, thereby increasing the molecular weight. The molecular weight of monomers can typically be calculated from the given chemical formula.

As used herein, "molecular weight" if not otherwise specified means number average molecular weight ($M_n$). The molecular weight ($M_n$) of the polymerizable compound before setting can be determined using nuclear magnetic resonance spectroscopy (end-group determination). In this respect proton ($^1H$) NMR techniques are employed to estimate the molecular weight of the precursor of the prepolymer. Integrated signals of the terminal $=CH_2$ groups are compared to the integrated sum of proton signals from backbone hydrocarbon protons taking into account co-monomer ratio, if applicable. To achieve appropriate separation of terminal methylene proton signals from the backbone proton signals, terminal hydroxyl groups are esterified with trifluoroacetic acid.

As used herein, "(meth)acryl" is a shorthand term referring to "acryl" and/or "methacryl." For example, a "(meth) acryloxy" group is a shorthand term referring to either an acryloxy group (i.e., $CH_2=CH-C(O)-O-$) and/or a methacryloxy group (i.e., $CH_2=C(CH_3)-C(O)-O-$).

As used herein, the terms "initiator" and "starter" refer to a substance capable of starting or initiating a curing process for resins or monomers, for example, by a redox/auto-cure chemical reaction, by a radiation induced reaction, or by a heat induced reaction.

As used herein, the phrase "cationically polymerizable compound" is defined as a compound which can be polymerized using an initiator containing or being able to generate cations, especially reactive cations.

As used herein, the term "powder" refers to a dry, bulk solid composed of a large number of very fine particles that may flow freely when shaken or tilted.

As used herein, the term "paste" refers to a soft, viscous mass of solids dispersed in a liquid.

As used herein, a composition is "essentially free of" or "substantially free of" a certain component (e.g., a resin), if the composition does not contain said component as an essential feature. Thus, said component is not intentionally added to the composition either as such or in combination with other components or ingredients of other components. A composition being essentially free of a certain component (e.g., a resin) usually contains the component in an amount of less than about 5 wt.-%, less than about 1 wt.-%, less than about 0.5 wt.-%, or less than about 0.01 wt.-%, with respect to the total weight of the composition or material. The composition may not contain said component at all. However, sometimes the presence of a small amount of the said component can be unavoidable, for example, due to impurities contained in the raw materials used.

As used herein, a "particle" or "particulate filler" refers to a solid substance having a shape which can be geometrically determined. The shape can be regular or irregular. Particles can typically be analyzed with respect to e.g. grain size and grain size distribution. A particulate filler can be composed of free-flowing particles. "Free-flowing" means that the particulate filler can be sieved, that is, it behaves like dry powdered sugar.

As used herein "nanosilica" is used synonymously with "nano-sized silica particles," and refers to silica particles having an average size of at most 200 nanometers. As used herein for a spherical particle, "size" refers to the diameter of the particle. As used herein for a non-spherical particle, "size" refers to the longest dimension of the particle.

As used herein, the term "silica sol" refers to a stable dispersion of discrete, amorphous silica particles in a liquid, typically water.

As used herein, the terms "pyrogenic silica" and "fumed silica" are used interchangeably and refer to amorphous silicas formed in the vapor phase. Pyrogenic silica may contain, for example, a few hundred primary particles fused into branched-chain, three-dimensional aggregates. Examples of pyrogenic silica include products available under the trade designations AEROSIL OX-50. AEROSIL-130, AEROSIL-150, and AEROSIL-200 available from DeGussa AG, (Hanau, Gennany) and CAB-O-SIL M5 available from Cabot Corp (Tuscola, Ill.).

As used herein, "non-pyrogenic silica" refers to amorphous silica that is not formed in the vapor phase. Examples of non-pyrogenic silicas include precipitated silicas and silica gels.

As used herein, "silane treated" means that the surface of a particle has been modified by application of a silane, wherein "silane" refers to a silane coupling agent comprising an organosilicon compound, such as, for example: 3-methacryloxypropyltrimethoxysilane, γ-methacryloyloxypropyltrimethoxysilane or hexamethyldisilazane.

As used herein, "aggregated silica" is descriptive of an association of primary silica particles often bound together by, for example, residual chemical treatment, covalent chemical bonds, or ionic chemical bonds. Although complete breakdown of aggregated silica into smaller entities may be difficult to achieve, limited or incomplete breakdown may be observed under conditions including, for example, shearing forces encountered during dispersion of the aggregated silica in a liquid.

As used herein, the terms "hardenable" and/or "curable" refer to compositions that can be cured or solidified, for example, by chemical reactions such as crosslinking reactions.

As used herein, the phrase "ambient conditions" refers to conditions to which non-aqueous compositions as described herein are typically subjected during storage and handling Ambient conditions may include, for example, a pressure of about 900 mbar to about 1100 mbar, a temperature of about −10° C. to about 60° C., and/or a relative humidity of about 10% to about 100%. In the laboratory ambient conditions are typically adjusted to about 23° C. and about 1 atmosphere (e.g., 0.95 to 1.05 atmosphere). In the dental and orthodontic field ambient conditions are reasonably understood to include, for example, a pressure of about 950 mbar to about 1050 mbar, a temperature of about 15° C. to about 40° C., and/or a relative humidity of about 20% to about 80%.

As used herein, the term "dental tissue" includes the hard tooth substance (enamel and dentin), the gingival region (soft dental tissue) surrounding the hard tooth substance and hard tooth substance bearing orthodontic appliances.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain situations by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Also, as used herein in connection with a measured quantity, the term "approximately" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

The above brief description of various embodiments of the present disclosure is not intended to describe each embodiment or every implementation of the present disclosure. Rather, a more complete understanding of the disclosure will become apparent and appreciated by reference to the following description and claims in view of the accompanying drawings. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list. Further, it is to be understood that other embodiments may be utilized and structural changes may be made without departing from the scope of the present disclosure.

BRIEF DESCRIPTION OF THE DRAWINGS

FIG. 1 is a graphical representation illustrating the change in viscosity observed after mixing exemplary non-aqueous compositions as disclosed herein.

DETAILED DESCRIPTION OF ILLUSTRATIVE EMBODIMENTS

Most dental composites are photocurable methacrylates, which harden when exposed to curing lights. As disclosed herein, a secondary reaction mechanism can be added into flowable composites. This secondary mechanism can be an orthogonal polymerization, a new chemical reaction, or even secondary interactions such as H-bonding, electrostatic force, or van der Waals forces. When the secondary mechanism is activated, either by mixing or external stimuli, it can form big molecules, or long chain polymers, or networks, or particles, or phase-separated domains. All the above-mentioned reactions/activations can potentially increase the viscosity, changing flowable composites into regular packable composites. Disclosed herein are direct dental restorative materials that can flow and adapt to the cavity like a flowable composite, that undergo a transition in viscosity (i.e., "staging") that allows them to be sculpted and shaped, after which they can be hardened to full restorative properties.

FIG. 1 illustrates the change in viscosity observed after mixing exemplary non-aqueous compositions as disclosed herein, with the y-axis representing viscosity, and the x-axis representing time. For various embodiments of the non-aqueous compositions described herein, two-step curing mechanisms are disclosed, wherein the first step involves a non-free radical reaction including but not limited to, an acid-base interaction or a cationic or conjugate addition or ring opening reaction. The second step involves initiation of a free radical cure of a free radically curable resin. The non-aqueous compositions initially start with at least two parts (e.g., Part A and Part B), each having a flowable viscosity (i.e., a low viscosity). As illustrated in FIG. 1, Part A and Part B are mixed at time T1, where the Part A has an initial viscosity of $V_{0A}$ and the Part B has same or different initial viscosity of $V_{0B}$. The mixed composition maintains a flowable viscosity until time T2. The time interval between time T1 and time T2, represented as interval 1, can be long or short. In some embodiments interval I can be at least 1 second or at least 2 seconds. In other embodiments interval I can be not greater than 1 minute, not greater than 2 minutes or not greater than 5 minutes. Interval I is a time sufficient for the mixed composition to be applied, for example, to a dental surface. A change to a higher staged viscosity (e.g., the viscosity of a universal composite) occurs between time T2 and time T3 following the application of the mixed composition during interval I. The interval between time T2 and T3 is represented by interval II. In some embodiments interval II can be at least 1 second or at least 5 seconds. In other embodiments interval II can be not less than 2 minutes, not less than 3 minutes, not less than 5 minutes or not less than 10 minutes. The mixed composition can maintain a stable staged viscosity (consistency) between time T3 and time T4, represented as time interval III. A stable staged viscosity is defined by a change in viscosity (consistency) of not more than 1%, 2%, 3%, 5%, 10%, 15% or 20%. The time interval III, is sufficient to sculpt and/or shape the mixed composition as desired. The increased viscosity of interval III could also provide a time to place and move a bonded part prior to final cure. The increased viscosity of interval III could also provide green strength to a bonded part, so the assembly could be moved, package or shipped prior to final cure. Due to the wide variety of useful process steps that could be conducted during time interval III, a large time interval would be advantageous. In some embodiments interval III can be not less than 1 minute or not less than 2 minutes. In other embodiments it would be advantageous for interval III to be not greater than 30 or not greater than 40 minutes. In still other embodiments it would be advantageous for interval III to be greater than 30 days, greater than 6 months or even greater than 1 year. Finally, after the mixed composition has been sculpted and/or shaped as desired, free radical polymerization can be initiated at time T4 to provide a hardened composition at time T5. This is represented as time interval IV. It should be noted that the times and viscosities illustrated in FIG. 1 are not necessarily to scale.

In one aspect, the present disclosure provides a non-aqueous composition including: a flowable Part A including at least one free radically polymerizable resin and Reactant A; and a flowable Part B including at least one resin and Reactant B; wherein at least one of flowable Part A and flowable Part B further includes a free radical initiator system; wherein flowable Part A and flowable Part B are capable of being mixed to provide a flowable mixed composition; wherein when flowable Part A and flowable Part B are mixed, Reactant A and Reactant B are capable of interacting to cause a non-free radical reaction within a first staging time to provide a first staged stable consistency for the mixed composition that is lower than the arithmetic mean of the consistency of flowable Part A and the consistency of flowable Part B; and wherein the mixed composition having the first staged stable consistency is capable of forming a hardened dental composition upon initiation of free radical polymerization. In certain embodiments, the at least one resin of flowable Part B includes at least one free radically polymerizable resin.

In certain embodiments, Reactant A may be present on the surface of an inorganic filler. In certain embodiments, Reactant B may be present on the surface of an inorganic filler. Reactant A or B may be placed onto the surface of the inorganic filler by placing the reactant and filler in suitable solvent, adding catalyst, and reacting the non-staging chemistry to the surface of the filler, and then removing the solvent/catalyst, leaving a surface modified with Reactant A or Reactant B.

The non-aqueous compositions described herein are essentially free of water (i.e., they do not include water as an essential feature). Thus, water is not intentionally added to the composition either as such or in combination with other components or ingredients of other components. Notably, glass ionomer cements are intended to be excluded from the non-aqueous compositions described herein. A composition being essentially free of water usually contains water in an amount of less than about 5 wt.-%, and in some embodiments less than about 2 wt.-%, with respect to the total weight of the composition. The composition may not contain water at all. However, sometimes the presence of a small amount of water can be unavoidable, for example, due to impurities contained in the raw materials used.

A wide variety of compounds and materials for Reactant A of flowable Part A and Reactant B of flowable Part B can be used in the non-aqueous compositions disclosed herein. For one example, Reactant A can include an acid and reactant B can include a base, and upon mixing flowable Part A and flowable Part B, the acid can react with the base in an ionic acid-base reaction.

The viscosity and curing properties of a specific non-aqueous composition will depend on a number of variables including, for example, type of resin in each part, type of filler and amount of filler in each part and mixing method. However, the amount of Reactant A in Part A, the amount of Reactant B in Part B, and the ratio of Part A and Part B in the non-aqueous composition can generally be varied to obtain the properties desired for each composition, particularly as illustrated by the working Examples disclosed herein.

The exemplary combinations of compounds and materials for Reactant A and Reactant B are each further discussed herein below.

Acid-Base Chemistry

A two-step curing mechanism is described herein, wherein the first step involves the reaction of an acid with a base in an ionic acid-base reaction, followed by initiation of the free radical cure of a free radically curable resin. Due to the staged viscosity during application, the materials combine the flowable viscosity required for maximal adaptation to cavity walls with a universal viscosity desired for shaping of the occlusal surface.

For some embodiments of the non-aqueous compositions disclosed herein, Reactant A can include an acid and reactant B can include a base, and upon mixing flowable Part A and flowable Part B, the acid can react with the base in an ionic acid-base reaction.

A wide variety of acids can be used for Reactant A. In certain embodiments, the acid includes one or more acidic groups. In certain embodiments the acid is soluble in the free radically polymerizable resin. In certain embodiments, the acid includes an organic acid having one or more acidic groups. In certain embodiments, the organic acid further includes (meth)acrylate functionality.

Exemplary acids for use as Reactant A include, but are not limited to, those selected from the group consisting of sulfonic acids, phosphonic acids, phosphoric acids, carboxylic acids, antimonic acids, boric acids, alpha hydroxy carboxylic acid, hydroxamic acid, esters thereof, salts thereof, and combinations thereof.

In some embodiments, Part A includes 0.5 wt.-% to 40 wt.-% of the acid, based on the total weight of Part A. In certain embodiments, Part A includes 2 wt.-% to 30 wt.-% of the acid, based on the total weight of Part A. In some certain embodiments, Part A includes 5 wt.-% to 20 wt.-% of the acid, based on the total weight of Part A.

A wide variety of bases can be used for Reactant B. In certain embodiments, the base includes one or more basic groups. In certain embodiments the base is soluble in the free radically polymerizable resin. In certain embodiments, the base includes an organic amine having one or more amino groups. In certain embodiments, the organic amine further includes (meth)acrylate functionality.

Exemplary bases for use as Reactant B include, but are not limited to, those selected from the group consisting of primary amines, secondary amines, tertiary amines and salts thereof, and combinations thereof.

Exemplary bases could also include intrinsically basic metal oxides or glass particles. In some embodiments the intrinsically basic metal oxides or intrinsically basic glass particles for use as the base for Reactant B may comprise Zirconia, Alumina, Yttria, Titania, Ceria, Zinc Oxide, Aluminosilicates, doped aluminosilicates and combinations thereof. Dopants for aluminosilicates may include, for example: Ba, La, Ca, Li, and combinations thereof.

In some embodiments the intrinsically basic metal oxides or intrinsically basic glass particles comprise a surface treated with one or more labile acids. In some embodiments the one or more labile acids may be selected from the group consisting of sulfonic acids, phosphonic acids, phosphoric acids, carboxylic acids, antimonic acids, boric acids, alpha hydroxy carboxylic acid, hydroxamic acid, esters thereof, salts thereof, and combinations thereof.

Exemplary bases could also include intrinsically basic oxide or intrinsically basic glass particles surface treated with one or more silanes in combination with a labile acid.

In some embodiments, Part B includes 5 wt.-% to 40 wt.-% of the Reactant B, based on the total weight of Part B. In certain embodiments, Part B includes 2 wt.-% to 30 wt.-% of the Reactant B, based on the total weight of Part B. In some certain embodiments, Part B includes 5 wt.-% to 20 wt.-% of the Reactant B, based on the total weight of Part B.

In certain embodiments, the non-aqueous composition includes the Reactant A and the Reactant B in the composition at an equivalent ratio of 5:1 to 1:5 (acid to base).

In certain embodiments, the non-aqueous composition includes the Reactant A and Reactant B, where Reactant B is selected from a cationic salt. Cationic salts of Reactant B may be, for example, cationic salts of Zn, Bi, Na, Ba, La, Ca, Li, Sn, Al, Sr, or K and mixtures thereof. Furthermore, in certain embodiments the counter ion of the cationic salt may comprise (meth)acrylate functionality.

Polymerizable Resins

Polymerizable resins are materials having free radically active functional groups and include monomers, oligomers, and polymers having one or more ethylenically unsaturated groups. Suitable materials contain at least one ethylenically unsaturated bond, and are capable of undergoing addition polymerization.

Free radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274 (Boettcher et al.), and acrylated oligomers such as those of U.S. Pat. No. 4,642,126 (Zador et al.); and vinyl compounds such as styrene, diallyl phthalate, divinyl succinate, divinyladipate and divinylphthalate. Mixtures of two or more of these free radically polymerizable materials can be used if desired. Suitable polymerizable polymers include, for example, partially or fully acrylate- or methacrylate-functionalized polymers including, for example, functionalized poly(acrylic acid) polymers, cellulosics, poly(vinylalcohol) polymers, poly(oxyethylene)-poly(oxypropylene) block copolymers, poly(ethyleneglycol) polymers, and combinations thereof.

In certain embodiments, flowable Part A can include 5 wt.-% to 90 wt.-% free radically polymerizable resin, based on the total weight of flowable Part A. In certain embodiments, flowable Part A can include 10 wt.-% to 60 wt.-% free radically polymerizable resin, based on the total weight of flowable Part A. In some embodiments, flowable Part A can include 15 wt.-% to 40 wt.-% free radically polymerizable resin, based on the total weight of flowable Part A.

For embodiments in which flowable Part B includes a free radically polymerizable resin, flowable Part B can include 5 wt.-% to 90 wt.-% free radically polymerizable resin, based on the total weight of flowable Part B. In certain embodiments, flowable Part B can include 10 wt.-% to 60 wt.-% free radically polymerizable resin, based on the total weight of flowable Part B. In some embodiments, flowable Part B can include 15 wt.-% to 40 wt.-% free radically polymerizable resin, based on the total weight of flowable Part B.

Inorganic Fillers

In certain embodiments, flowable Part A further includes at least one inorganic filler. In certain embodiments, flowable Part B further includes at least one inorganic filler. In some embodiments, both flowable Part A and flowable Part B each include at least one inorganic filler. The at least one inorganic filler in flowable Part A and the at least one inorganic filler in flowable Part B may be the same inorganic filler or different inorganic fillers. In some embodiments, a crosslinked organic material that is insoluble in the resin system can be included in addition to, or instead of, the inorganic filler.

A filler system includes one or more fillers and may be selected from one or more materials suitable for incorporation in dental materials. In some embodiments the filler is finely divided with an average particle size (i.e., the longest dimension of the particle, such as the diameter) of no greater than about 10 micrometers and a maximum particle size of no greater than about 50 micrometers. The filler can have a unimodal or polymodal (e.g., bimodal) particle size distribution. The filler can be radiopaque, radiolucent, or nonradiopaque. Examples of suitable inorganic fillers include naturally occurring or synthetic materials such as quartz, nitrides (e.g., silicon nitride), glasses derived from, for example, Ce, Sb, Sn, Zr, Sr, Ba, or Al, colloidal silica, feldspar, borosilicate glass, kaolin, talc, titania, and zinc glass, zirconia-silica fillers; low Mohs hardness fillers such as those described in U.S. Pat. No. 4,695,251 (Randklev); and submicron silica particles (e.g., pyrogenic silicas such as those available under the trade designation "AEROSIL" such as "OX 50," "OX 130," "OX150," and "OX 200" from Degussa, Ridgefield Park, N. J., and "Cab-0-Sil M5" silica from Cabot Corp., Boston, Mass.). Examples of suitable organic filler particles include filled or unfilled pulverized polycarbonates, polyepoxides, and the like. In some embodiments, filler particles are quartz, submicron silica, and non-vitreous microparticles of the type described in U.S. Pat. No. 4,503,169 (Randklev). Mixtures of these fillers are also contemplated, as well as combination fillers made from organic and inorganic materials. In some embodiments, fluoroaluminosilicate glass fillers, either untreated or silanol treated, can be used. These glasses have the added benefit of releasing fluoride at the site of dental work when placed in the oral environment.

Fillers can be chosen to enhance certain properties, such as compressive strength, diametral tensile strength, wear resistance, appearance, translucency, radiopacity, and storage stability of the dental materials, as well as to limit exothermic effects during the initial set phase. Optionally, the surface of the filler particles may be treated with a surface treatment, such as a silane coupling agent, in order to enhance the bond between the filler and the resin system. The coupling agent may be functionalized with reactive curing groups, such as acrylates, methacrylates, and the like. In some embodiments, the total amount of filler is about 2 wt-% to about 90 wt.-%, based on the total weight of the components of the dental material. In certain embodiments, the total amount of filler is about 30 wt.-% to about 85 wt.-%, based on the total weight of the components of the dental material.

For embodiments in which flowable Part A includes at least one inorganic filler, flowable Part A can include 10 wt.-% to 90 wt.-% inorganic filler, based on the total weight of flowable Part A. In certain embodiments, flowable Part A can include 30 wt.-% to 80 wt.-% inorganic filler, based on the total weight of flowable Part A.

For embodiments in which flowable Part B includes at least one inorganic filler, flowable Part B can include 10 wt.-% to 90 wt.-% inorganic filler, based on the total weight of flowable Part B. In certain embodiments, flowable Part B can include 30 wt.-% to 80 wt.-% inorganic filler, based on the total weight of flowable Part B.

For the non-aqueous compositions described herein, at least one of flowable Part A and flowable Part B includes a free radical initiator system.

Non Acid-Reactive Fillers

The inorganic fillers disclosed herein can be non acid-reactive fillers. A non acid-reactive filler is a filler that when combined with a polyacid in the presence of water either (i) does not cure in a glass ionomer cement reaction at all, or (ii) that only shows a delayed curing reaction. In some embodiments disclosed herein, a base may be present on the surface of an inorganic filler. However, a base present on the surface of the inorganic filler typically would not render the filler to be an acid-reactive filler useful in a glass ionomer cement.

A wide variety of non acid-reactive fillers can be used in non-aqueous compositions disclosed herein. In certain embodiments, the non acid-reactive filler is non-toxic and suitable for use in the mouth of a human being. A non acid-reactive filler can be radiopaque or radiolucent. Optionally, the surface of the particles of a non acid-reactive filler can be surface treated (e.g., with silanes).

In certain embodiments, the non acid-reactive filler can include quartz, nitrides, kaolin, borosilicate glass, strontium oxide based glass, barium oxide based glass, silica, alumina, titania, zirconia, or a combination thereof.

In certain embodiments, the non acid-reactive filler can include a metal oxide such as alumina, silica, zirconia, titania, or a combination thereof. In some embodiments the metal oxide can further include modifiers or dopants such as sodium, magnesium, lithium, calcium, strontium, barium, yttrium, ytterbium, lanthanum, zinc, iron, manganese, bismuth oxides, or a combination thereof.

In certain embodiments, the non acid-reactive filler has a mean particle size of 0.005 micrometer to 20 micrometers. For some embodiments, the non acid-reactive filler has a mean particle size of 0.01 micrometer to 10 micrometers. In certain embodiments, the non acid-reactive filler has a d50 of less than 10 micrometers. For embodiments in which both the first paste and the second paste include a non acid-reactive fillers, the mean particle size of the non acid-reactive filler in the second paste can be the same or different than the mean particle size of the non acid-reactive filler in the first paste.

Exemplary non acid-reactive filler are further described, for example, in International Application Publication No. WO 2017/015193 A1 (Jahns et al.).

In certain embodiments, the non acid-reactive filler can be provided as a dispersion or sol of particles in a liquid (e.g., water). If the filler is provided as an aqueous dispersion or sol, the amount of water in the aqueous dispersion or sol has to be taken into account when the amount of water and filler in the composition is calculated or determined.

In certain embodiments, the non acid-reactive filler can include non-aggregated, water-miscible, nano-sized silica particles having at least 25% surface coverage of the particles with a silane, as further discussed herein below.

Nano-Sized Silica Particles

The inorganic fillers disclosed herein can be nano-sized silica particles.

In some embodiments, the nano-sized silica particles can be clusters of nanoparticles. Clusters of nanoparticles may be formed from a combination of non-heavy metal oxide and/or heavy metal oxide, for example as disclosed in U.S. Pat. No. 6,730,156 (Windisch et al.).

In some embodiments, nano-sized silica particles can be non-aggregated.

In some embodiments, the non-aggregated, nano-sized silica particles are substantially free of fumed silica (i.e., pyrogenic silica). However pyrogenic fillers (e.g., fumed silica) can be added as optional additives to the dental compositions.

A wide variety of non-aggregated, nano-sized silica particles can be surface treated as described herein. In some embodiments, the non-aggregated, nano-sized silica particles are available as a silica sol. In certain embodiments, the starting silica sol is NALCO 2329 or LEVASIL 50/50.

Exemplary non-aggregated, nano-sized silica particles include those available from Nalco Chemical Co. (Naperville, Ill.) under the product designation NALCO COLLOIDAL SILICAS (e.g., NALCO products 1040, 1042, 1050, 1060, 2327 and 2329), Nissan Chemical America Company, Houston, Texas (e.g., SNOWTEX-ZL, -OL, -O, -N, -C, -20L, -40, and -50); Admatechs Co., Ltd., Japan (e.g., SX009-MIE, SX009-MIF, SC1050-MJM, and SC1050-MLV); Grace GmbH & Co. KG, Worms, Germany (e.g., those available under the product designation LUDOX, e.g., P-W50, P-W30, P-X30, P-T40 and P-T40AS); Akzo Nobel Chemicals GmbH, Leverkusen, Germany (e.g., those available under the product designation LEVASIL, e.g., 50/50, 100/45, 200/30%, 200A/30, 200/40, 200A/40, 300/30 and 500/15), and Bayer Material Science AG, Leverkusen, Germany (e.g., those available under the product designation DISPERCOLL S, e.g., 5005, 4510, 4020 and 3030). Further exemplary fillers including non-aggregated, nano-sized silica particles and methods of preparing the fillers are disclosed in, for example, International Publication No. WO 01/30307 (Craig et al.).

For embodiments in which the dental composition further includes pyrogenic fillers (e.g., fumed silica), a wide variety of pyrogenic fillers such as fumed silica can be used. Exemplary fumed silicas include for example, products sold under the trade designations AEROSIL series OX-50, -130, -150, and -200, Aerosil R8200 available from Degussa AG, (Hanau, Germany), CAB-O-SIL M5 available from Cabot Corp (Tuscola, Ill.), and HDK types, e.g. HDK-H 2000, HDK H15; HDK H18, HDK H20 and HDK H30 available from Wacker.

In one embodiment, the non-aggregated, nano-sized silica particles have an average particle size of at most about 200 nanometers, in some embodiments at most about 150 nanometers, and in certain embodiments at most about 120 nanometers. In one embodiment, the non-aggregated, nano-sized silica particles have an average particle size of at least about 20 nanometers, in some embodiments at least about 50 nanometers, and in certain embodiments at least about 70 nanometers. These measurements can be based on a TEM (transmission electron microscopy) method, whereby a population of particles is analyzed to obtain an average particle size.

An exemplary method for measuring the particle diameter can be described is as follows: Samples approximately 80 nm thick are placed on 200 mesh copper grids with carbon stabilized formvar substrates (SPI Supplies-a division of Structure Probe, Inc., West Chester, PA). A transmission electron micrograph (TEM) is taken, using JEOL 200CX (JEOL, Ltd. of Akishima, Japan and sold by JEOL USA, Inc.) at 200Kv. A population size of about 50-100 particles can be measured and an average diameter can be determined.

In one embodiment, the average surface area of the non-aggregated, nano-sized silica particles is at least about 15 $m^2/g$, and in some embodiments at least about 30 $m^2/g$.

In some embodiments, the non-aggregated, nano-sized silica particles used in the dental pastes disclosed in the present application are substantially spherical and substantially non-porous. Although the silica may be essentially pure in certain embodiments, it may contain small amounts of stabilizing ions such as ammonium and alkaline metal ions in other embodiments.

Initiator Systems

For free radical polymerization (hardening), an initiation system can be selected from systems which initiate polymerization via radiation, heat, redox/auto-cure chemical reaction, or a combination thereof. For example, the combination of a photoinitiator system (i.e., radiation cure) and a redox cure can provide for improved depth of cure.

For certain embodiments of the non-aqueous compositions described herein, the free radical initiator system can include a photoinitiator system. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

For certain embodiments the free radical initiator system can include a photoinitiator system. One type of suitable initiator (i.e., initiator system) is described in U.S. Pat. No. 5,545,676 (Palazzotto et al.), which includes a three component or ternary photoinitiator system. This system includes an iodonium salt, e.g., a diaryliodonium salt, which can be a simple salt (e.g., containing an anion such as $Cl^-$, $Br^-$, $I^-$, or $C_2H_5SO_3^-$) or a metal complex salt (e.g., containing $SbF_5OH^-$ or $AsF_6^-$). Mixtures of iodonium salts can be used if desired. The second component in this ternary photoinitiator system is a sensitizer, which is capable of light absorption within the range of wavelengths of about 400 nm to about 1200 nm. The third component in this ternary photoinitiator system is an electron donor and includes amines (including aminoaldehydes and aminosilanes or other amines as described for the first initiator system), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid.

Examples of sensitizers suitable for use in a ternary photoinitiator system include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. In some embodiments, the sensitizers are ketones (e.g., monoketones or alpha-diketones), ketocoumarins, aminoarylketones, p-substituted aminostyryl ketone compounds, or combinations thereof. Exemplary visible light sensitizers include camphorquinone, glyoxal, biacetyl, 3,3,6,6-tetramethyleyclohexanedione, 3,3,7,7-tetramethyl-1,2-cycloheptanedione, 3,3,8,8-tetramethyl-1,2-cyclooctanedione, 3,3,18,18-tetramethyl-1,2-cyclooctadecanedione, dipivaloyl, benzil, furil, hydroxybenzil, 2,3-butanedione, 2,3-pentanedione, 2,3-hexanedione, 3,4-hexanedione, 2,3-heptanedione, 3,4-heptanedione, 2,3-octanedione, 4,5-octanedione, 1,2-cyclohexanedione, and combinations thereof. In certain embodiments, the sensitizer is camphorquinone.

In some embodiments, visible light-induced initiators include camphorquinone combined with a suitable hydrogen donor (e.g., an amine such as those described above for the first initiator system), and optionally a diaryliodonium simple or metal complex salt, chromophore-substituted halomethyl-s-triazine, or halomethyl oxadiazole. In certain embodiments, visible light-induced photoinitiators include combinations of an alpha-diketone (e.g., camphorquinone) with additional hydrogen donors, and optionally a diaryliodonium salt (e.g., diphenyliodonium chloride, bromide, iodide or hexafluorophosphate).

In some embodiments, ultraviolet light-induced polymerization initiators include ketones, such as benzyl and benzoin, acyloins, and acyloin ethers. In certain embodiments, ultraviolet light-induced polymerization initiators include 2,2-dimethoxy-2-phenylacetophenone available under the trade designation IRGACURE 651 and benzoin methyl ether (2-methoxy-2-phenylacetophenone), both from Ciba Specialty Chemicals Corp., Tarrytown, N.Y.

Various other initiators are known in the art, such as described in U.S. Pat. No. 7,674,850 (Karim et al.) and U.S. Pat. No. 7,816,423 (Karim et al.).

The initiator system is present in an amount sufficient to provide the desired rate of hardening (e.g., polymerizing and/or crosslinking). For a photoinitiator, this amount will be dependent in part on the light source, the thickness of the layer to be exposed to radiant energy, and the extinction coefficient of the photoinitiator. In some embodiments the initiator system is present in a total amount of at least about 0.01 wt.-%, in certain embodiments at least about 0.03 wt.-%, and in some certain embodiments at least about 0.05 wt.-%, based on the weight of the hardenable dental composition. In some embodiments the initiator system is present in a total amount of no more than about 10 wt.-%, in certain embodiments no more than about 5 wt.-%, and in some certain embodiments no more than about 2.5 wt.-%, based on the weight of the hardenable dental composition.

For certain embodiments of the non-aqueous compositions described herein, the free radical initiator system can include a redox initiator system. A redox initiator system includes redox agents. The redox agents may include an oxidizing agent and a reducing agent. Suitable polymerizable components, redox agents, optional acid-functional components, and optional fillers that are useful in the present disclosure are described in U.S. Pat. No. 7,173,074 (Mitra et al.) and U.S. Pat. No. 6,982,288 (Mitra et al.). Alternatively, the redox agents may include a free-radical initiator system containing enzymes as disclosed in U.S. Patent Application Pub. No. 2004/0122126 A1 (Wu et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. In at least some embodiments, the reducing and oxidizing agents are sufficiently shelf-stable and free of undesirable colorization to permit their storage and use under typical dental conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline, aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. In certain embodiments the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments a secondary ionic salt may be included to enhance the stability of the polymerizable composition as described in U.S. Pat. No. 6,982,288 (Mitra et al.).

The reducing and oxidizing agents are present in amounts sufficient to permit an adequate free-radical reaction rate. This can be evaluated by combining all of the ingredients of the polymerizable composition except for any optional filler, and observing whether or not a hardened mass is obtained.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

Optional Additives

The non-aqueous compositions disclosed herein may optionally include various additives known in the art including, but not limited to, flavorants, fluoridating agents, buffering agents, numbing agents, remineralization agents, desensitization agents, colorants, indicator(s), viscosity modifiers, surfactants, stabilizers, preservative agents (e.g., benzoic acid), or combinations thereof. The presence of a colorant can aid in detecting that the aqueous composition has coated all the desired intraoral surfaces. The intensity of a colorant can also aid in detecting the uniformity of the coating on the intraoral surfaces.

For embodiments of the non-aqueous compositions disclosed herein in which an additive is present in Part A, Part A includes at least 0.01 wt.-% additive, at least 0.05 wt.-% additive, or at least 0.1 wt.-% additive, based on the total weight of Part A. For the non-aqueous compositions disclosed herein in which an additive is present in Part A, Part A includes at most 5 wt.-% additive, at most 3 wt.-% additive, or at most 1 wt.-% additive, based on the total weight of Part A.

For embodiments of the non-aqueous compositions disclosed herein in which an additive is present in Part B, Part B includes at least 0.01 wt.-% additive, at least 0.05 wt.-% additive, or at least 0.1 wt.-% additive, based on the total weight of Part B. For the non-aqueous compositions disclosed herein in which an additive is present in Part B, Part B includes at most 5 wt.-% additive, at most 3 wt.-% additive, or at most 1 wt.-% additive, based on the total weight of Part B.

Methods and Devices

In one embodiment, the method includes: providing a non-aqueous composition as described herein; mixing flowable Part A and flowable Part B to provide a mixed composition; and allowing the consistency of the mixed composition to decrease to a first staged stable consistency that is lower than the arithmetic mean of the consistency of flowable Part A and the consistency of flowable Part B.

In another embodiment, the method includes providing a non-aqueous composition as described herein; mixing flowable Part A and flowable Part B to provide a mixed composition; allowing the consistency of the mixed composition to decrease to a first staged stable consistency that is lower than the arithmetic mean of the consistency of flowable Part A and the consistency of flowable Part B; and subjecting the mixed composition having the first staged stable consistency to conditions sufficient to initiate free radical polymerization to provide the hardened dental composition. In some embodiments, conditions sufficient to initiate free radical polymerization are selected from the group consisting of irradiation, heat, and combinations thereof.

Flowable Part A and flowable Part B can be brought together in a variety of ways.

In one embodiment, flowable Part A and flowable Part B may be contained in separate scalable vessels (e.g., made out of plastic or glass). For use, the practitioner may take adequate portions of the components from the vessels and mix the portions by hand on a mixing plate. Hand mixing can be achieved by dispensing about equal mass of flowable Part A and flowable Part B on a mix surface, such as mix pad or glass plate. A dental cement spatula can be used to rapidly fold the two pastes together in a side to side mixing action in a small mixing area (e.g., approximately 1 inch in diameter).

In some embodiments, flowable Part A and flowable Part B are contained in separate compartments of a storage device. The storage device typically includes two compartments for storing the respective parts, each compartment being equipped with a nozzle for delivering the respective parts. Once delivered in adequate portions, the parts can then be mixed by hand on a mixing plate.

In certain embodiments, the storage device has an interface for receiving a static mixing tip. The mixing tip is used for mixing the respective parts. Static mixing tips are available from, for example, SulzerMixpac Company. Useful storage devices include cartridges, syringes, and tubes.

The storage device typically includes two housings or compartments having a front end with a nozzle and a rear end and at least one piston movable in the housing or compartment.

Useful cartridges arc described, for example, in U.S. Patent Application Pub. No. 2007/0090079 A1 (Keller et al.) and U.S. Pat. No. 5,918,772 (Keller et al.). Useful cartridges are available from, for example, SulzerMixpac AG (Switzerland). Useful static mixing tips are described, for example, in U.S. Patent Application Pub. No. 2006/0187752 A1 (Keller et al.) and in U.S. Pat. No. 5,944,419 (Streiff). Useful mixing tips are available from, for example, Sulzer-Mixpac AG (Switzerland).

Other useful storage devices are described, for example, in WO 2010/123800 (3M), WO 2005/016783 (3M), WO 2007/104037 (3M), WO 2009/061884 (3M).

Alternatively, flowable Part A and flowable Part B can be provided in individual syringes and the individual pastes can be mixed by hand prior to use.

In certain embodiments, flowable Part A and flowable Part B can be provided as a kit that includes the multiple parts, and instructions describing one or more methods (as disclosed herein) for mixing flowable Part A and flowable Part B to form a cured composition.

In one embodiment, the present disclosure provides a device for storing flowable Part A and flowable Part B. The device includes: a first compartment containing flowable Part A; and a second compartment containing flowable Part B. In some embodiments, both the first compartment and the second compartment each independently include a nozzle or an interface for receiving an entrance orifice of a static mixing tip.

Upon mixing flowable Part A and flowable Part B of a non-aqueous composition as described herein, the composition undergoes a transition in viscosity (i.e., a "staging") that allows the composition to be sculpted and shaped. The mixed composition is said to have "staged" when the consistency (e.g., see test method section in the working examples) of the mixed composition is lower (the paste was more viscous) than either flowable Part A or flowable Part B prior to mixing.

Practitioners generally desire good handling properties in a dental material, as it often translates to time savings. For example, in dental restorative work, it is desirable that dental materials does not slump because after a practitioner places the material in the mouth and manipulates the material by contouring and feathering, the practitioner generally wants the imparted shape to remain unchanged until the material is hardened. Materials used for restorative work, having a sufficiently high yield stress, generally will not slump: that is, they will not flow under the stress of gravity. The yield stress of a material is the minimum stress required to cause the material to flow, and is described in "Rheology Principles, Measurements, and Applications" by C. W. Macosko, VCH Publishers, Inc., New York, 1994, p. 92. If the stress due to gravity is below the yield stress of the material, then the material will not flow. The stress due to gravity, however, will depend on the mass of dental material being placed as well as the shape.

"Contouring" refers to the process of shaping a material (using dental instruments) so that it resembles the natural dental anatomy. For easy contouring, materials should have a sufficiently high viscosity that they maintain their shape after manipulation with a dental instrument, and yet the viscosity should not be so high that it is difficult to shape the material. "Feathering" refers to the process of reducing the dental material to a thin film in order to blend the material into the natural dentition. This is done with a dental instrument at the margin of the manipulated material and the natural dentition. It is also desirable that the dental material not stick to placement instruments, to minimize further alteration of the shape or surface topography.

In one embodiment in which the dental material of the present disclosure is a restorative, the dental material can have little to no slump, yet easily adapt, for example, to a cavity preparation, and be easily contoured and feathered. In certain embodiments, the dental materials do not stick to placement instruments, and overall are advantageously fast and easy to use in dental procedures such as, for example, restoring tooth structure.

"Viscosity" refers to how easily a liquid or pseudo-liquid (e.g., dough, clay, or paste) flows when stress is applied (stress of gravity when poured). This term can be definite—such as a measured value (Pa s), or relative such as flows faster or slower than a comparative material, or "thin as water". The term can also be used in the general sense, and still have intuitive meaning to one skilled in the area art of the subject of interest, such as "the dental restorative had low viscosity".

Herein the term "consistency" will refer to the definite measure as described in the "consistency test method" described in the Example Section, unless otherwise stated Consistency value of a material is not the same as viscosity. In fact, consistency varies in an inverse direction compared to viscosity. In other words, a lower consistency value corresponds to a more viscous or thicker material; a higher consistency value corresponds to a lower viscosity.

Herein the term "viscosity" will refer to the general or descriptive form of the word unless otherwise noted.

Herein the term "flowable composite" or "flowable" refers to a pseudo-liquid that is filled with about 10% to about 80% filler. It has a characteristic viscosity such that it will yield and/or slump and/or flow under the stress of gravity or stress applied by hand when delivered in a syringe. It can be easily extruded through a small cannula. The viscosity is sufficiently low to allow its penetration into small undercuts as well as the ability to flow and adapt to the shape of the prepared tooth surface, which is being restored.

Herein the term "universal composite", "universal", "packable composite", "packable" or any variation thereof refers to a pseudo-liquid that is filled with about 10% to about 90% filler. It has a characteristic viscosity such that it will not substantially yield and/or slump after contouring under the stress of gravity.

For certain embodiments of the non-aqueous compositions described herein, the consistency of the mixed composition is stable when the consistency changes no more than 20 percent over 30 minutes. In certain embodiments, the consistency of the mixed composition changes no more than 20 percent over 15 minutes. In some embodiments, the consistency of the mixed composition changes no more than 15 percent over 5 minutes.

For certain embodiments of the non-aqueous compositions described herein, the consistency of the mixed composition is stable when the consistency changes no more than 10 percent over 30 days. In certain embodiments, the consistency of the mixed composition changes no more than 5 percent over 8 hours. In some embodiments, the consistency of the mixed composition changes no more than 5 percent over 30 minutes.

Staging time, also known as Interval II in FIG. 1, is the time difference between T3 and T2, when the composition of the combination of Part A and Part B is changing consistency. In certain embodiments, the first staging time is 2 seconds to 60 minutes. In other certain embodiments, the first staging time is 10 seconds to 5 minutes. In some embodiments, the first staging time is 15 seconds to 2 minutes.

After flowable part A and flowable part B are mixed and placed on a tooth surface, a staged handling state occurs, the material is contoured and feathered, following which the material can be hardened to form a lasting durable dental restoration.

The dental composition disclosed herein may be hardened by inducing the polymerizable component to polymerize. In one embodiment, free radical polymerization can then be initiated through the exposure of actinic radiation, such as blue light. In certain embodiments, the composition is irradiated with radiation having a wavelength of 400 to 1200 nanometers, and in certain embodiments with visible radiation. Visible light sources include, for example, the sun, lasers, metal vapor (e.g., sodium and mercury) lamps, incandescent lamps, halogen lamps, mercury arc lamps, fluorescent room light, flashlights, light emitting diodes, tungsten halogen lamps, and xenon flash lamps. The polymerization can lead to final properties effective to form a lasting durable dental restoration.

In another embodiment, enough time will pass such that a dark cure redox reaction will initiate the polymerization at a rate much slower the staging interaction, allowing time for contouring, leading to final properties such to make a lasting durable dental restoration.

In yet another embodiment actinic radiation will lead to the polymerization of the bulk of the restoration. Simultaneously a dark cure redox reaction will be producing radicals to polymerize areas of the restoration that may have a geometric or optical feature that blocks the exposure of light.

The resulting hardened dental composition typically has some requisite strength. A common measure of strength is diametral tensile strength, as defined in the test section. A minimal requirement for a dental material would be about 30 MPa.

A typical hardened dental material is bonded on or to a tooth surface. It usually has a general color match to the surrounding dentition, and follows the shape and contour of natural tooth structure. The hardened material is qualitatively hard and scratch resistant when probed with a dental tool. The material would also possess requisite strength values if tested outside the mouth.

In some embodiments, the mixing ratio of Part A and Part B is 10:1 to 1.10 with respect to volume, and in certain embodiments, 1:1 with respect to volume.

In other embodiments, the mixing ratio of Part A and Part B is 10:1 to 1:10 with respect to weight, and in certain embodiments 1:1 with respect to weight.

In some embodiments, the mixed composition having the first staged stable consistency forms a transient dental filling, a transient dental inlay, a transient dental onlay, a transient dental crown, a transient dental bridge, a transient denture, a transient dental appliance, or a combination thereof.

In some embodiments, the hardened dental composition forms a dental filling, a dental inlay, a dental onlay, a dental crown, a dental bridge, a denture, a dental appliance, or a combination thereof.

ILLUSTRATIVE EMBODIMENTS OF THE PRESENT DISCLOSURE

Various embodiments are disclosed that can provide stageable compositions, and methods of making and using same.

Embodiment 1A is a non-aqueous composition comprising: a flowable Part A comprising at least one resin and Reactant A; and a flowable Part B comprising at least one resin and Reactant B; wherein at least one of the resins of flowable Part A and flowable Part B further comprise a free radically polymerizable resin; wherein at least one of flowable Part A and flowable Part B further comprises a free radical initiator system; wherein flowable Part A and flowable Part B are capable of being mixed to provide a flowable mixed composition; wherein when flowable Part A and flowable Part B are mixed, Reactant A and Reactant B are capable of interacting to cause a non-free radical reaction within a first staging time to provide a first staged stable consistency for the mixed composition that is lower than the arithmetic mean of the consistency of flowable Part A and the consistency of flowable Part B; and wherein Reactant A comprises an acid and Reactant B comprises a base, and upon mixing flowable Part A and flowable Part B, the Reactant A acid is capable of reacting with the Reactant B base in an ionic acid-base reaction; and wherein the mixed composition having the first staged stable consistency is capable of forming a hardened dental composition upon initiation of free radical polymerization.

Embodiment 2A is the non-aqueous composition of embodiment 1 A, wherein the at least one resin of flowable Part B comprises at least one free radically polymerizable resin.

Embodiment 3A is the non-aqueous composition of embodiment 1A or 2A, wherein flowable Part A further comprises at least one inorganic filler.

Embodiment 4A is the non-aqueous composition of any one of embodiments 1A to 3A, wherein flowable Part B further comprises at least one inorganic filler.

Embodiment 5A is the non-aqueous composition of embodiment 3A or 4A, wherein flowable Part A and flowable Part B each comprise the same inorganic filler.

Embodiment 6A is the non-aqueous composition of embodiment 3A or 4A, wherein flowable Part A and flowable Part B each comprise different inorganic fillers.

Embodiment 7A is the non-aqueous composition of any one of embodiments 3A to 6A, wherein flowable Part A comprises 10 wt.-% to 90 wt.-% inorganic filler, based on the total weight of flowable Part A.

Embodiment 8A is the non-aqueous composition of any one of embodiments 3A to 7A, wherein flowable Part A comprises 30 wt.-% to 80 wt.-% inorganic filler, based on the total weight of flowable Part A.

Embodiment 9A is the non-aqueous composition of any one of embodiments 4A to 8A, wherein flowable Part B comprises 10 wt.-% to 90 wt.-% inorganic filler, based on the total weight of flowable Part B.

Embodiment 10A is the non-aqueous composition of any one of embodiments 4A to 9A, wherein flowable Part B comprises 30 wt.-% to 80 wt.-% inorganic filler, based on the total weight of flowable Part B.

Embodiment 11A is the non-aqueous composition of any one of embodiments 1A to 10A, wherein the free radical initiator system comprises a photoinitiator system.

Embodiment 12A is the non-aqueous composition of any one of embodiments 1A to 11A, wherein the free radical initiator system comprises a redox initiator system.

Embodiment 13A is the non-aqueous composition of any one of embodiments 1A to 12A, wherein the mixed composition having the first staged stable consistency is a contourable composition.

Embodiment 14A is the non-aqueous composition of any one of embodiments 1A to 13A, wherein consistency of the mixed composition having the first staged stable consistency changes no more than 20 percent over 30 minutes.

Embodiment 15A is the non-aqueous composition of any one of embodiments 1A to 14A, wherein the first staging time is 5 seconds to 5 minutes.

Embodiment 16A is the non-aqueous composition of any one of embodiments 1A to 15A, wherein the first staging time is 10 seconds to 2 minutes.

Embodiment 17A is the non-aqueous composition of any one of embodiments 1A to 16A, wherein the first staging time is 15 seconds to 1 minute.

Embodiment 18A is the non-aqueous composition of any one of embodiments 1A to 17A, wherein Reactant A is present on the surface of an inorganic filler.

Embodiment 19A is the non-aqueous composition of any one of embodiments 1A to 18A, wherein Reactant B is present on the surface of an inorganic filler.

Embodiment 20A is the non-aqueous composition of any one of embodiments 1A to 19A, wherein the Reactant A acid comprises an organic acid having one or more acidic groups.

Embodiment 21A is the non-aqueous composition of embodiment 20A, wherein the organic acid further comprises (meth)acrylate functionality.

Embodiment 22A is the non-aqueous composition of any one of embodiments 1A to 21A, wherein the Reactant A acid is selected from the group consisting of sulfonic acids, phosphonic acids, phosphoric acids, carboxylic acids, antimonic acids, boric acids, alpha hydroxy carboxylic acid, hydroxamic acid, esters thereof salts thereof, and combinations thereof.

Embodiment 23A is the non-aqueous composition of any one of embodiments 1A to 22A, wherein the Reactant B base comprises an organic amine having one or more amino groups.

Embodiment 24A is the non-aqueous composition of embodiment 23A, wherein the organic amine further comprises (meth)acrylate functionality.

Embodiment 25A is the non-aqueous composition of any one of embodiments 1A to 24A, wherein the Reactant B base is selected from the group consisting of primary amines, secondary amines, tertiary amines, salts thereof, and combinations thereof.

Embodiment 26A is the non-aqueous composition of embodiment 25A, wherein one or more the primary amines, secondary amines, tertiary amines, and salts thereof, are carboxylated.

Embodiment 27A is the non-aqueous composition of any one of embodiments 1A to 26A, wherein the Reactant A acid and the Reactant B base are present in the composition at an equivalent ratio of 5:1 to 1:5 (acid to base).

Embodiment 28A is the non-aqueous composition of any of the embodiments 1A to 27A, wherein the Reactant B comprises an intrinsically basic metal oxide or an intrinsically basic glass particle.

Embodiment 29A is the non-aqueous composition of 28A, wherein intrinsically basic metal oxide or intrinsically basic glass particle is surface treated with one or more silanes.

Embodiment 30A is the non-aqueous composition of 29A, wherein the one or more silanes comprise a polymerizable group.

Embodiment 31A is the non-aqueous composition of embodiment 28A, wherein the intrinsically basic metal oxide or basic glass particle comprise Zirconia, Alumina, Yttria, Titania, Ceria, Zinc Oxide, Aluminosilicates, doped Aluminosilicates or combinations thereof.

Embodiment 32A is the non-aqueous composition of embodiment 31A, wherein the doped aluminosilicates comprise dopants of Ba, La, Ca, Li, or combinations thereof.

Embodiment 33A is the non-aqueous composition of embodiment 28A, wherein the intrinsically basic metal oxide or intrinsically basic glass particle is surface treated with one or more labile acids.

Embodiment 34A is the non-aqueous composition of embodiment 33A, wherein the one or more labile acids are selected from the group consisting of sulfonic acids, phosphonic acids, phosphoric acids, carboxylic acids, antimonic acids, boric acids, alpha hydroxy carboxylic acid, hydroxamic acid, esters thereof, salts thereof, and combinations thereof.

Embodiment 35A is the non-aqueous composition of embodiment 33A, wherein the one or more labile acids further comprise a (meth)acrylate functionality.

Embodiment 36A is the non-aqueous composition of embodiment 28A, wherein the intrinsically basic oxide or glass particle comprises a surface treated with one or more silanes in combination with one or more labile acids, wherein the one or more labile acids are selected from the group consisting of sulfonic acids, phosphonic acids, phosphoric acids, carboxylic acids, antimonic acids, boric acids, alpha hydroxy carboxylic acid, hydroxamic acid, esters thereof, salts thereof, and combinations thereof.

Embodiment 37A is the non-aqueous composition of the embodiment 28A, wherein the composition further comprises primary amines, secondary amines, tertiary amines, salts thereof, and combinations thereof.

Embodiment 38A is the non-aqueous composition of embodiment 33A, comprising labile acids, further comprising primary amines, secondary amines, tertiary amines, salts thereof, and combinations thereof Embodiment 39A is the non-aqueous composition of any of the embodiments 1A to 38A, wherein the Reactant B is a cationic salt comprising Zn, Bi, Na, Ba, La, Ca, Li, Sn, Al, Sr, or K and mixtures thereof.

Embodiment 40A is the non-aqueous composition of embodiment 39A, wherein the counter ion of the cationic salt comprises (meth)acrylate functionality.

Embodiment 1B is a method of preparing a composition having a first staged stable consistency, the method comprising: providing a non-aqueous composition according to any one of embodiments 1A to 40A; mixing flowable Part A and flowable Part B to provide a mixed composition; and allowing the consistency of the mixed composition to decrease to a first staged stable consistency that is lower than the arithmetic mean of the consistency of flowable Part A and the consistency of flowable Part B.

Embodiment 2B is the method of embodiment 1B further comprising subjecting the mixed composition having the first staged stable consistency to conditions sufficient to initiate free radical polymerization to provide the hardened dental composition.

Embodiment 1C is the method of embodiment 1B or 2B, wherein mixing flowable Part A and flowable Part B comprises dispensing each part from a unit dose device through a static mixing device.

Embodiment 2C is the method of embodiment 2B, wherein conditions sufficient to initiate free radical polymerization are selected from the group consisting of irradiation, heat, and combinations thereof.

Embodiment 3C is the method of any one of embodiments 1B to 2C, wherein the mixed composition having the first staged stable consistency forms a transient dental filling, a transient dental inlay, a transient dental onlay, a transient dental crown, a transient dental bridge, a transient denture, a transient dental appliance, or a combination thereof.

Embodiment 4C is the method of any one of embodiments 2B to 2C, wherein the hardened dental composition forms a dental filling, a dental inlay, a dental onlay, a dental crown, a dental bridge, a denture, a dental appliance, or a combination thereof.

Embodiment 1D is a device for storing a non-aqueous composition according to any one of embodiments 1A to 40A comprising: a first compartment containing flowable Part A; and a second compartment containing flowable Part B.

Embodiment 2D is the device of embodiment ID, wherein both the first compartment and the second compartment each independently comprises a nozzle or an interface for receiving an entrance orifice of a static mixing tip.

Embodiment 1E is a method of preparing a composition having a first staged stable consistency, the method comprising: providing a device according to embodiment 1D or 2D; combining flowable Part A and flowable Part B to provide a mixed composition; and allowing the consistency of the mixed composition to decrease to a first staged stable consistency that is lower than the arithmetic mean of the consistency of flowable Part A and the consistency of flowable Part B.

Embodiment 1F is a method of preparing a hardened dental composition, the method comprising: providing a device according to embodiment 1D or 2D; combining flowable Part A and flowable Part B to provide a mixed composition; allowing the consistency of the mixed composition to decrease to a first staged stable consistency that is lower than the arithmetic mean of the consistency of flowable Part A and the consistency of flowable Part B; and subjecting the mixed composition having the first staged stable consistency to conditions sufficient to initiate free radical polymerization to provide the hardened dental composition.

Objects and advantages of this disclosure are further illustrated by the following non-limiting examples, but the particular materials and amounts thereof recited in these examples, as well as other conditions and details, should not be construed to unduly limit this disclosure.

EXAMPLES

The following examples are given to illustrate, but not limit, the scope of this disclosure. As used herein, all parts and percentages are by weight and all water was deionized, unless otherwise specified. Unless otherwise specified, materials can be obtained from Sigma-Aldrich Corp. (St. Louis, MO). All commercial materials were used as obtained from the vendor.

Preparatory Example 1: Acidic Monomers

The acidic monomers were prepared as follows

No Solvent—General Procedure:

The reactants were charged into a 250 ml 3-neck flask equipped with a mechanical stirrer and nitrogen. The flask was heated in an oil bath at a temperature of 140-145° C. until all components melted. The heat was then reduced to 105° C. (oil temperature) and mixing was resumed for 6-7 additional hours. 1H and 13C NMR was recorded for the product and found to be consistent with desired product.

Acid 1

Boltom P1000 (42.72 g, 363.0 milli-equivalent, Perstorp Polyols, Inc., Toledo, Ohio, USA) was charged into a 125 mL 2-neck round bottom flask equipped with a mechanical stirrer and a nitrogen stream. 4-(N,N-dimethylamino)pryidine (DMAP, 0.05 g, 0.4 mmol, Alfa Aesar, Tewksbury, MA, USA) was added followed by succinic anhydride (7.94 g, 79.3 mmol or mequivalent, Alfa Aesar, Tewksbury, MA, USA). The mixture was heated in an oil bath at 107° C. (oil temperature) overnight. Initially, the mixture was heterogeneous and cloudy. The mixture was heated and stirred overnight. The product was isolated on the next day as a pale-yellow oil.

Acid 2

Preparation of tris-2(succinylethyl) Isocyanurate

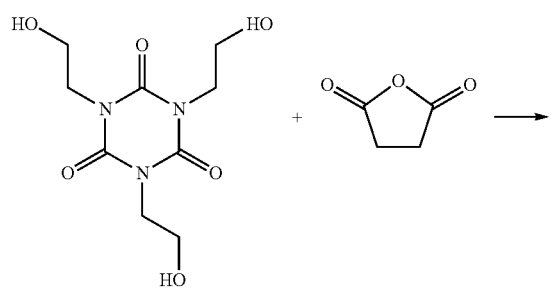

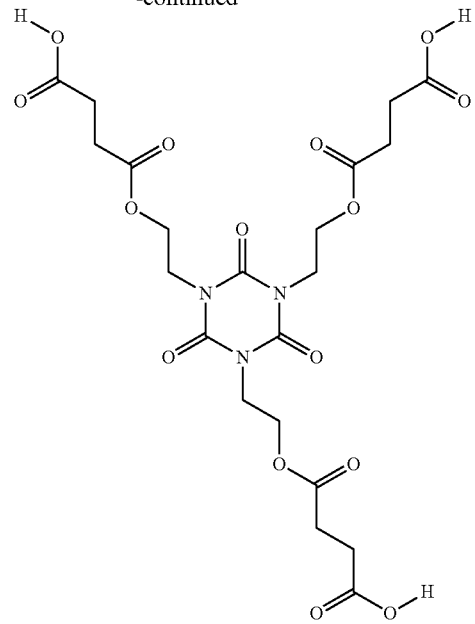

The example was prepared following the No Solvent—General Procedure. Succinic anhydride (30.2 g, 302 mmol), tris(2-hydroxyethyl) isocyanurate (26.10 g, 99.9 mmol) and DMAP (2 g, 16.21 mmol) were charged into a 250 ml 3-neck flask. Product structure was confirmed by NMR.

Acid 3

Preparation of tris-2(Maloylethyl) Isocyanurate

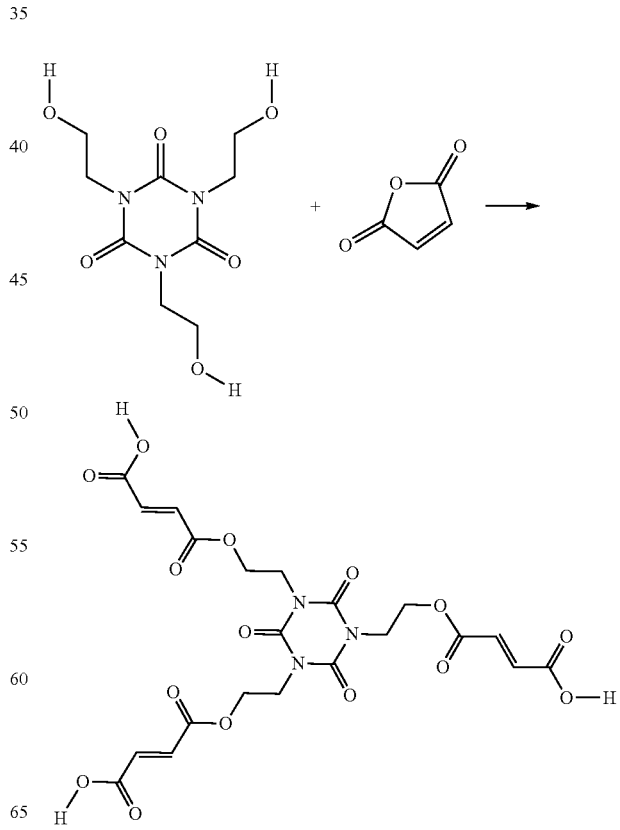

The example was prepared following the No Solvent—General Procedure. The following were added to a 3-neck flask: tris(2-hydroxyethyl) isocyanurate (29.4 g, 113 mmol) with maleic anhydride (33 g, 336.5 mmol). No DMAP used in this procedure. Product structure was confirmed by NMR.

Acid 4

Maleinized polybutadiene (7.5% by weight) ring-opened to free acid by esterification with HEMA.

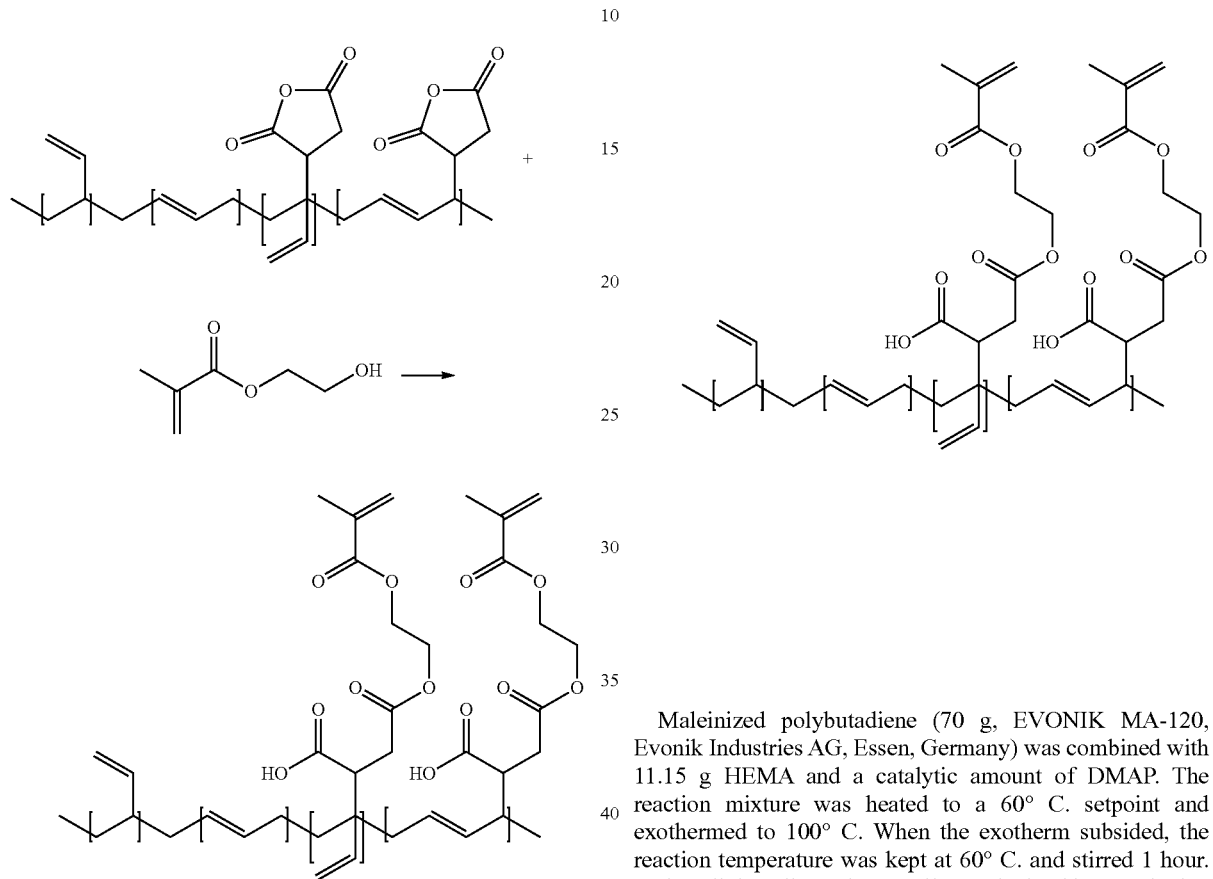

Maleinized polybutadiene (70 g, EVONIK MA-75, Evonik Industries AG, Essen, Germany) was combined with 6.97 g HEMA and a catalytic amount of DMAP. The reaction mixture was heated to a 60° C. setpoint and exothermed to 95° C. When the exotherm subsided, the reaction temperature was kept at 60° C. and stirred 1 hour. A clear, light yellow, viscous oil was obtained in quantitative yield.

Acid 5

Maleinized polybutadiene (12.0% by weight) ring-opened to free acid by esterification with HEMA.

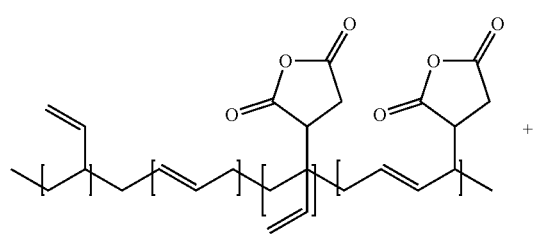

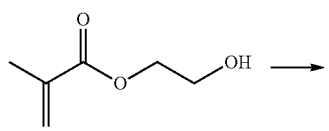

Maleinized polybutadiene (70 g, EVONIK MA-120, Evonik Industries AG, Essen, Germany) was combined with 11.15 g HEMA and a catalytic amount of DMAP. The reaction mixture was heated to a 60° C. setpoint and exothermed to 100° C. When the exotherm subsided, the reaction temperature was kept at 60° C. and stirred 1 hour. A clear, light yellow, viscous oil was obtained in quantitative yield.

Acid 6

Trimellitic anhydride chloride (6.65 g) was dissolved in dry DCM and cooled to 0°. Phthalate methacrylate alcohol (10.0 mL) was dissolved separately in dry DCM with 2.6 mL pyridine, and added dropwise to the acid chloride mixture at a rate sufficient to keep the temperature under 5° C. Once the addition was complete, the addition funnel was rinsed with fresh DCM into the reaction mixture and allowed to stir at room temperature overnight. The solids were filtered, BHT was added as stabilizer, and the DCM was stripped under vacuum. The resulting phthalate methacrylate anhydride was used in the next step without additional purification.

Phthalate methacrylate anhydride (11.90 g) from the previous step was combined with 2.03 g 1,3,5-Tris(2-hydroxyethyl)isocyanurate with catalytic DMAP, and the solids were dissolved in dry THF. The reaction was stirred and refluxed for 16 hours. The solvent was stripped under reduced pressure to give a colorless solid. Material was obtained in quantitative yield as a mixture of isomers.

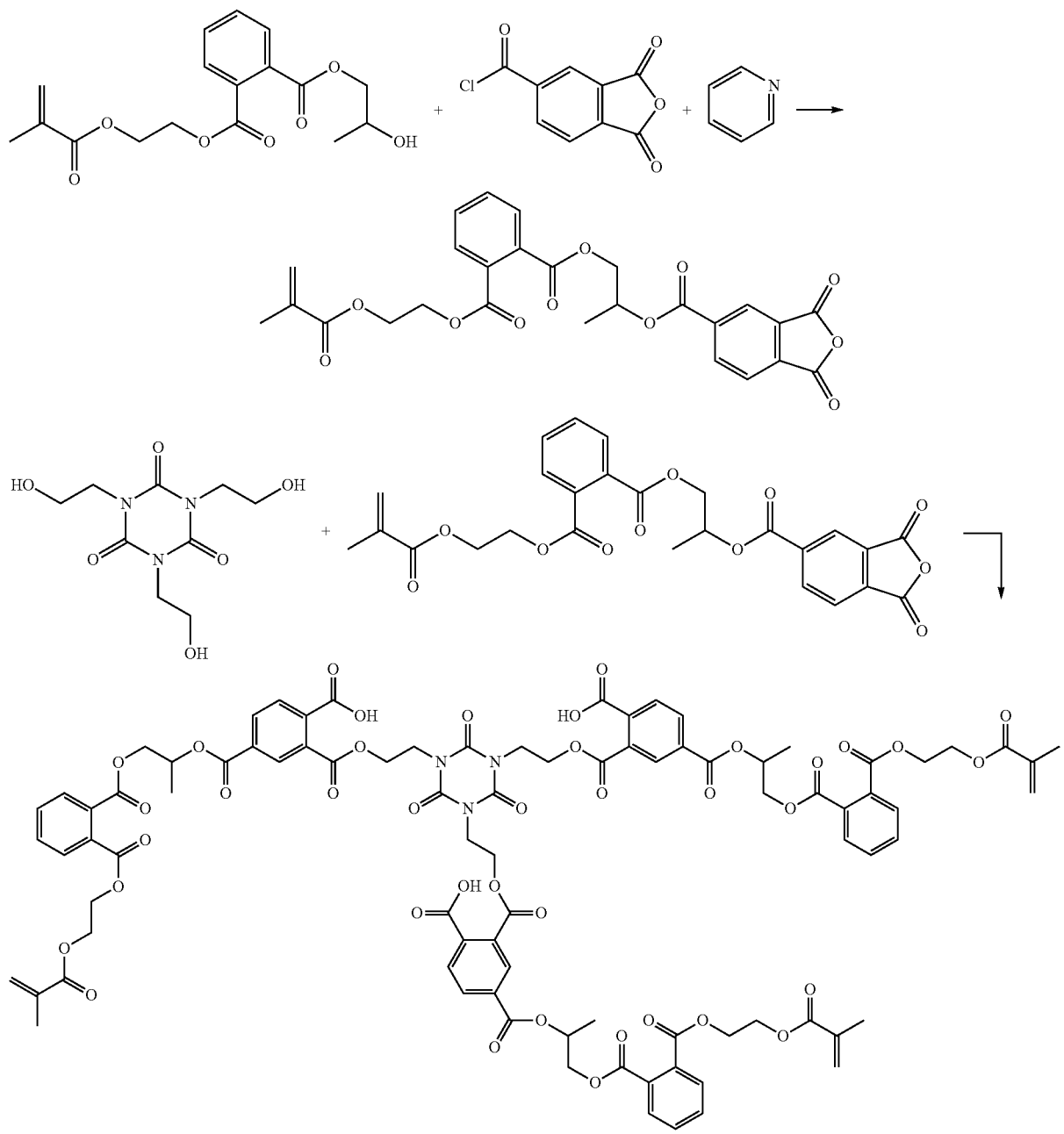
Acid 7
1,3,5-Tris(2-hydroxyethyl)isocyanurate (11.445 g) was combined with 39.990 g 4-META and 0.250 g DMAP in 250 mL dry tetrahydrofuran, and the reaction mixture was stirred and refluxed for 15 hours. The solvent was stripped under reduced pressure to give a colorless, highly viscous, sticky material that solidified as it cooled. Material was obtained in quantitative yield as a mixture of isomers.
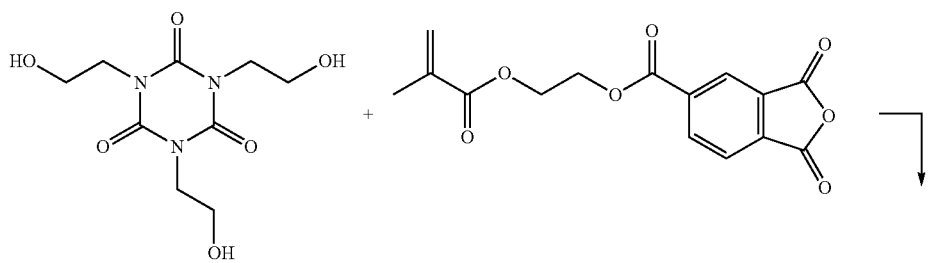

-continued

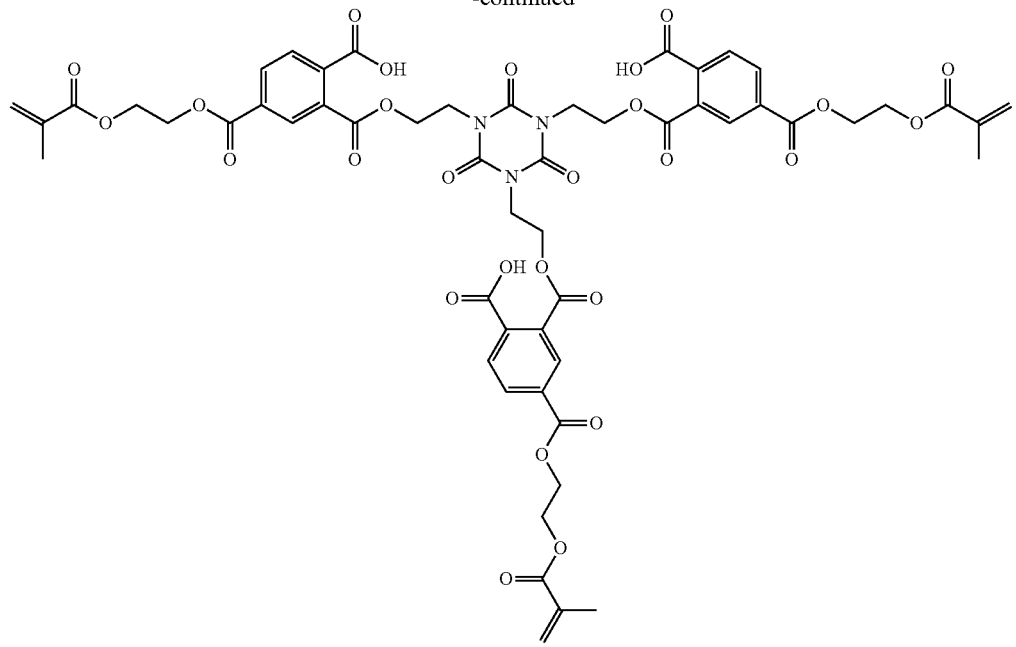

Acid 8

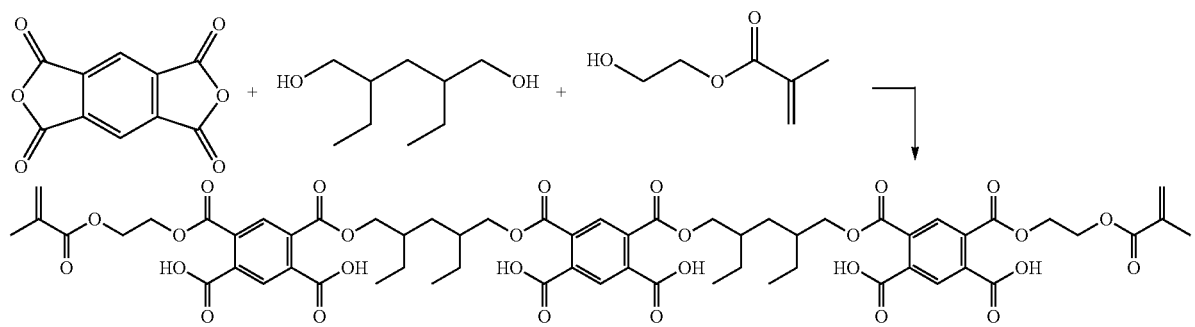

Pyromellitic dianhydride (50.00 g) was combined with 24.50 g 2,4-diethylpentane-1,5-diol (mixture of DL and meso isomers) and a catalytic amount of DMAP in 250 mL dry tetrahydrofuran. The reaction mixture was heated to reflux and the solids fully dissolved in 1 hour. The reaction mixture was refluxed an additional 2 hours, after which time 19 mL HEMA was added. The reaction mixture was stirred at reflux for 2 hours and then allowed to cool to room temperature. The solvent was stripped under reduced pressure to give a clear, colorless, highly viscous oil in quantitative yield as a mixture of isomers.

Acid 9

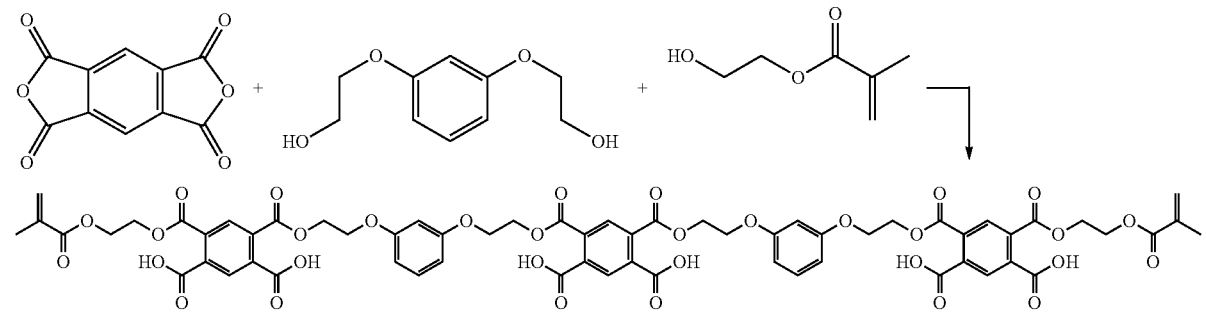

Pyromellitic dianhydride (30.02 g) was combined with 18.18 g ethoxylated resorcinol and a catalytic amount of DMAP in 125 mL dry tetrahydrofuran. The reaction mixture started as an orange color as the solvent was added. The reaction mixture was heated to a 45° C. setpoint and exothermed to 54° C. After 10 minutes the solids dissolved. When the exotherm began to subside the reaction temperature was increased to 66° C. and stirred 2 hours, during which time the reaction mixture's color changed from orange to very light yellow. 11.2 ml, HEMA was added and refluxed 2 hours. The solvent was stripped under reduced pressure to get a yellowish, very viscous liquid in quantitative yield that solidified at room temperature as a mixture of isomers.

Acid 10

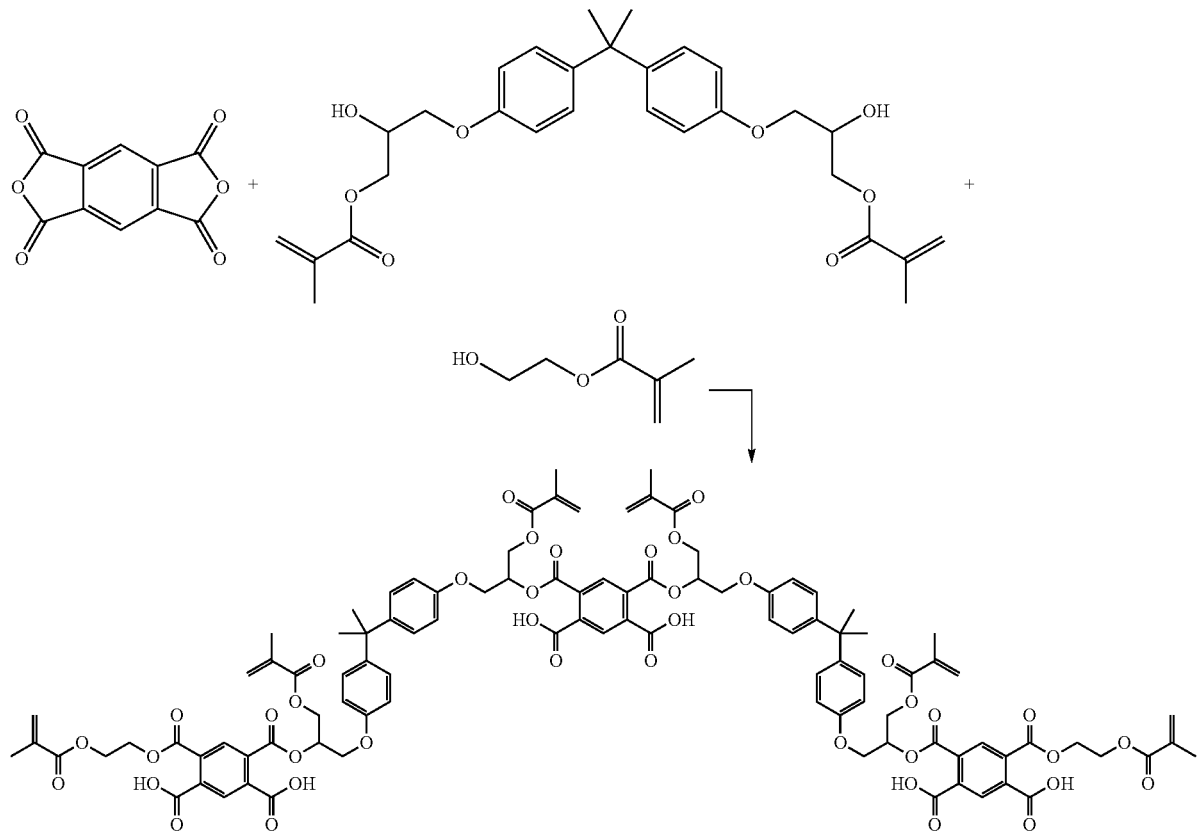

Pyromellitic dianhydride (50.030 g) was combined with 78.364 g bisGMA (mixture of isomers) and a catalytic amount of DMAP in 125 mL dry tetrahydrofuran. The reaction mixture started as a reddish color as the solvent was added. The reaction mixture was heated to a 45° C. setpoint and exothermed to 55° C. After 10 minutes the solids dissolved, and the reaction mixture became yellowish. When the exotherm began to subside, the reaction temperature was increased to 66° C. and stirred 2 hours, during which time the reaction mixture's color changed from yellow to colorless. 19 mL HEMA was added and refluxed 2 hours. The solvent was stripped under reduced pressure to give a very viscous liquid in quantitative yield that solidified at room temperature as a mixture of isomers.

Acid 11

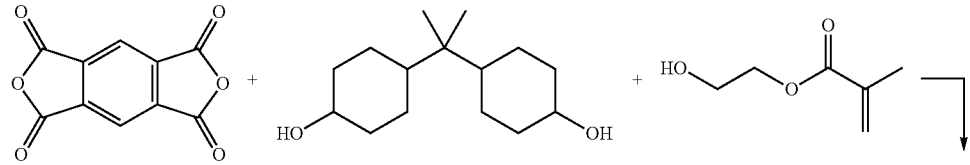

-continued

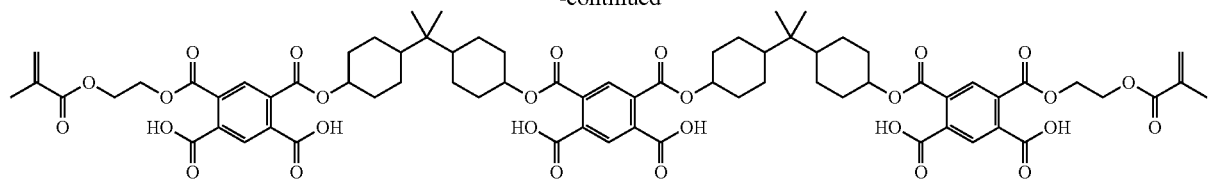

Pyromellitic dianhydride (50.007 g) was combined with 36.751 g 4,4' (propane-2,2 diyl)bis(cyclohexan-1-ol) (mixture of isomers) and a catalytic amount of DMAP in 150 mL dry tetrahydrofuran. The reaction mixture was heated to a 45° C. setpoint, during which time the reaction exothermed. When the exotherm began to subside, the reaction temperature was increased to 66° C. and stirred 3 hours. 19 mL HEMA was added and refluxed 2 hours. The solvent was stripped under reduced pressure to get a powdery solid in quantitative yield as a mixture of isomers.

Acid 12

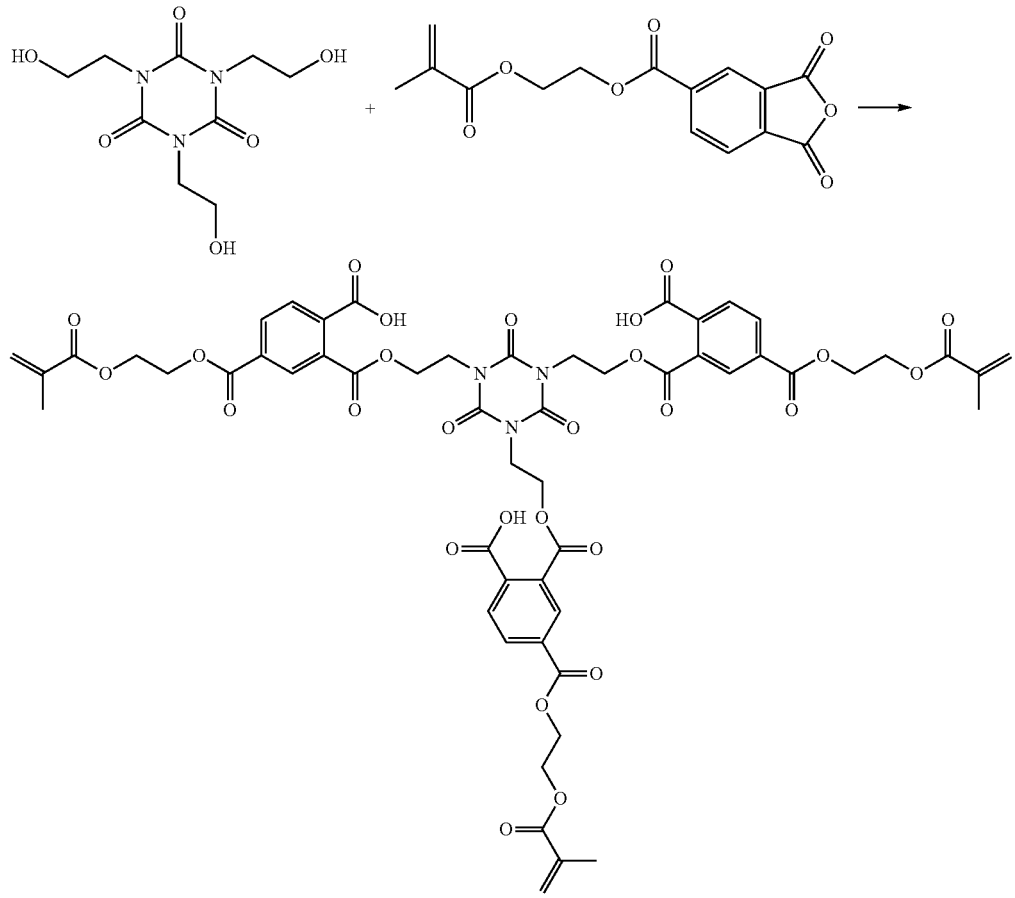

1,3,5-Tris(2-hydroxyethyl)isocyanurate (11.445 g) was combined with 39.990 g 4-META and 0.250 g DMAP in 250 mL dry tetrahydrofuran, and the reaction mixture was stirred and refluxed for 15 hours. The solvent was stripped under reduced pressure to give a colorless, highly viscous, sticky material that solidified as it cooled. Material was obtained in quantitative yield as a mixture of isomers.

Acid 13

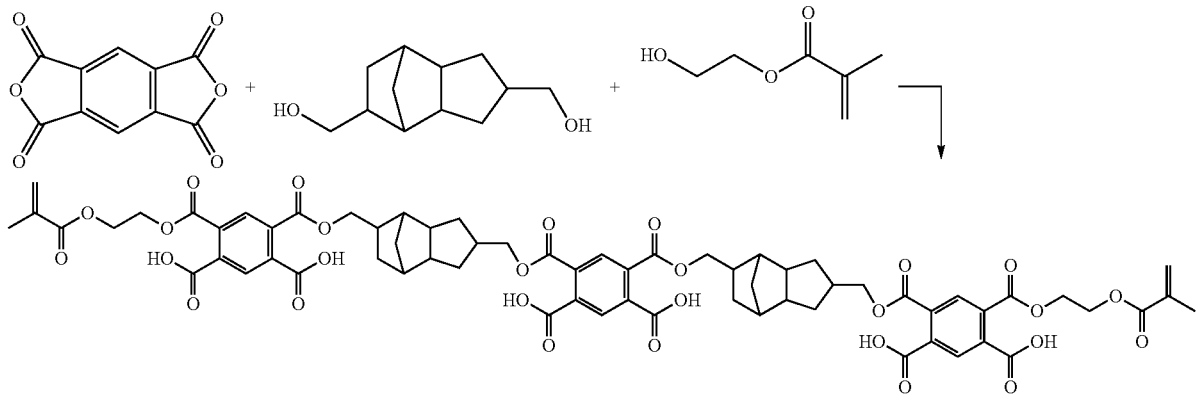

Pyromellitic dianhydride (21.929 g) was combined with 13.153 g TCD ((octahydro-1H-4,7-methanoindene-2,5-diyl) dimethanol) (mixture of isomers) and a catalytic amount of DMAP in 125 mL dry tetrahydrofuran. The reaction mixture was heated to reflux, and the solids fully dissolved in 1 hour. The reaction mixture was refluxed an additional 2 hours, and 8.2 mL HEMA was added. The reaction mixture was stirred at reflux for 2 hours, and then allowed to cool to room temperature. The solvent was stripped under reduced pressure to give a clear, colorless, highly viscous oil in quantitative yield as a mixture of isomers. The material solidified at room temperature.

Acid 14

Pyromellitic dianhydride (36.02 g) was combined with 42.25 g bisGMA (mixture of isomers) and a catalytic amount of DMAP in 150 mL dry tetrahydrofuran. The reaction mixture started as a reddish color as the solvent was added. The reaction mixture was heated to a 45° C. setpoint and exothermed to 55° C. After 10 minutes the solids dissolved, and the reaction mixture became yellowish. When the exotherm began to subside, the reaction temperature was increased to 66° C. and stirred 3 hours, during which time the reaction mixture's yellowish color faded considerably. HEMA (19 mL) was added and refluxed 2 hours. The solvent was stripped under reduced pressure to give a very viscous liquid in quantitative yield that solidified at room temperature as a mixture of isomers.

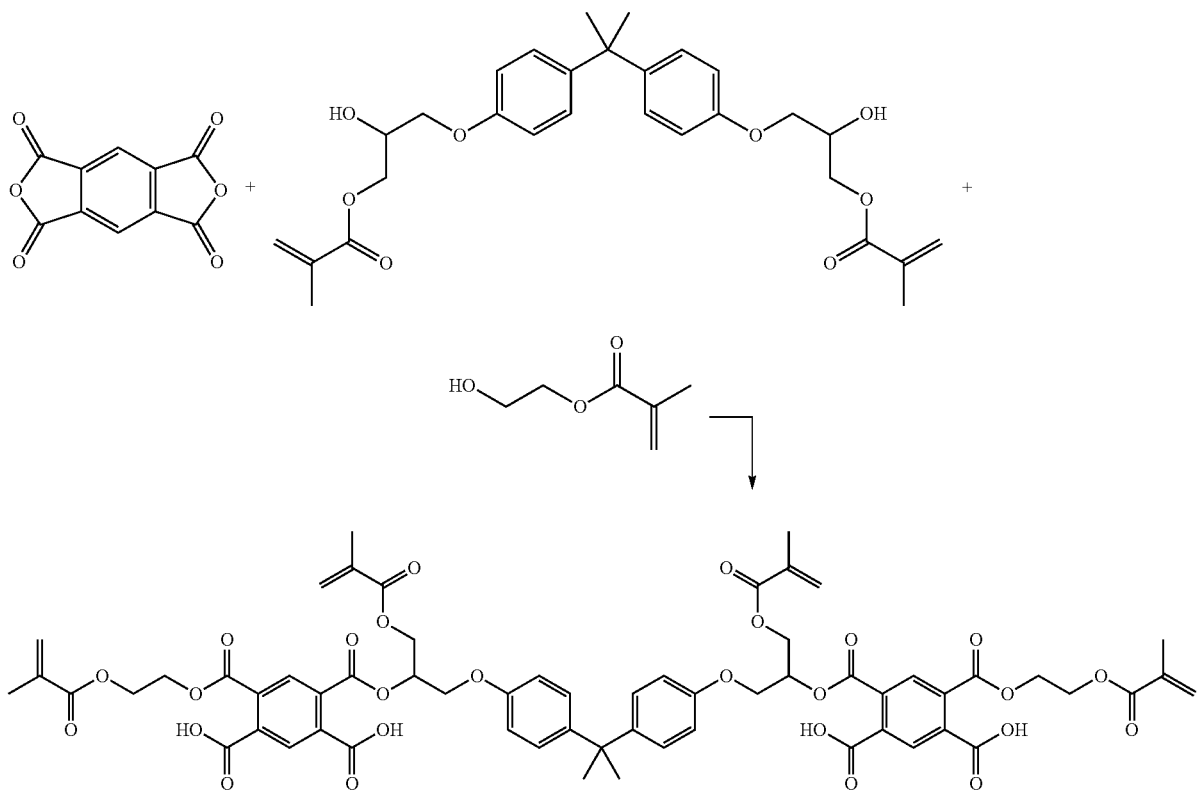

Preparatory Example 2: Basic Amines

Basic amines 1 through 7 consist of ter-polymeric amines. They were prepared by the following general procedure. The molar ratio of the constituent monomers is given in Preparatory TABLE 1.

General Procedure

The following was the general procedure followed for the preparation of ter-polymer basic amines.

Monomer 1, monomer 2 and monomer 3 were dissolved in isopropyl alcohol (150 mL, GFS Chemicals Inc., Powell, OH, USA) in a 250 mL two neck round bottom flask equipped with a mechanical stirrer and a nitrogen line bubbling in the solution bulk. AIBN (0.5% wt with respect to total monomer weight, Sigma Aldrich, St Louis, MO, USA) was added and nitrogen bubbling was continued for 30 minutes (to drive out any oxygen). The solution was then heated at 70° C. (oil temperature in an oil bath) overnight.

The heat was turned off. After cooling to room temperature, the slightly cloudy solution was precipitated in excess pet ether. The obtained residue was dried in a vacuum oven.

General Procedure for Methacrylation

The terpolymers (Base 1, calculated hydroxyl mmol equivalent weight charge) was placed in a glass jar then warmed up in an oven at around 60° C. IEM (Showa Denko America Inc. New York, NY, USA, mmol equivalence charge) was added and mixed. After cooling to room temperature, dibutytin dilaurate (about 10 drops) was added and the mixture was hand mixed with a Teflon stick. The mixture was left to stand on bench at room temperature to give a semi solid product. Complete reaction of IEM was checked by recording IR spectroscopy.

Base 1

2-N,N-Dimethylaminoethyl methacrylate/2-phenoxyethylacrylate/2-t-butylaminoethyl methacrylate Terpolymer Synthesis

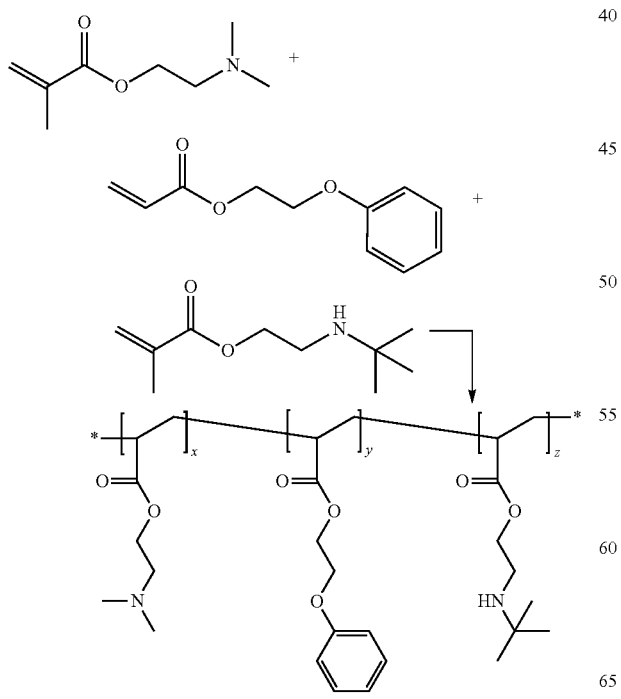

This terpolymer was prepared according to the General Procedure from 2-(N,N-dimethylamino)ethyl methacrylate (21.90 g, 139.3 mmol, Alfa Aesar, Tewksbury, MA, 01876, USA), 2-phenoxyethyl acrylate (26.30 g, 137 mmol), 2-t-butylaminoethyl methacrylate (5.79 g, 31.3 mmol, Sigma Aldrich, St Louis, MO, USA). Product was isolated as a viscous liquid.

Base 2

2-N,N-Dimethylaminoethyl methacrylate/n-butylacrylate/4-hydroxybutyl acrylate Terpolymer Synthesis

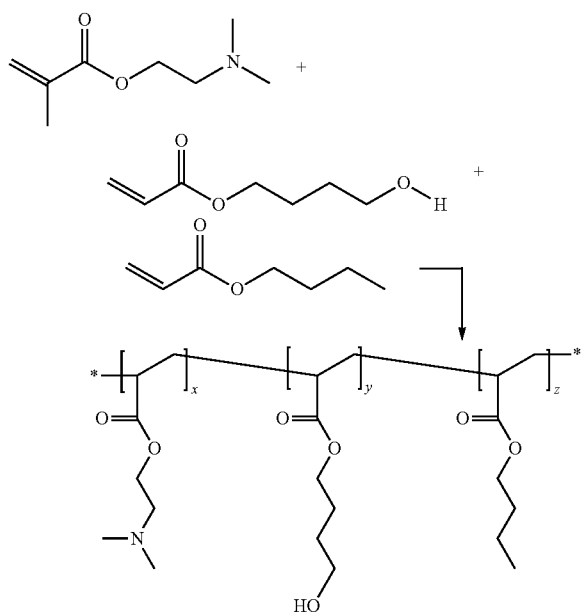

This example was prepared according to the General Procedure from 2-(N,N-dimethylamino)ethyl methacrylate (111.99 g, 712.36 mmol), n-butyl acrylate (91.31 g, 712.4 mmol, Alfa Aesar, Tewksbury, MA, 01876, USA), 4-hydroxybutyl acrylate (102.2 g, 708.9 mmol, TCI America, Portland, OR, USA). The product was isolated as a clear semi solid liquid.

Base 3

2-N,N-Dimethylaminoethyl methacrylate/2-phenoxyethylacrylate/2-hydroxyethyl methacrylate Terpolymer Synthesis

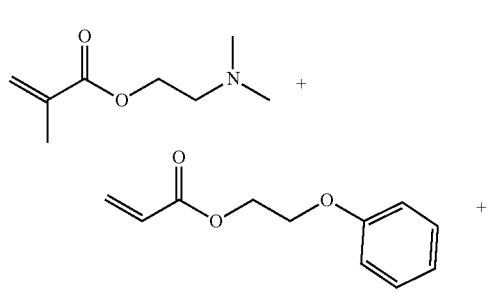

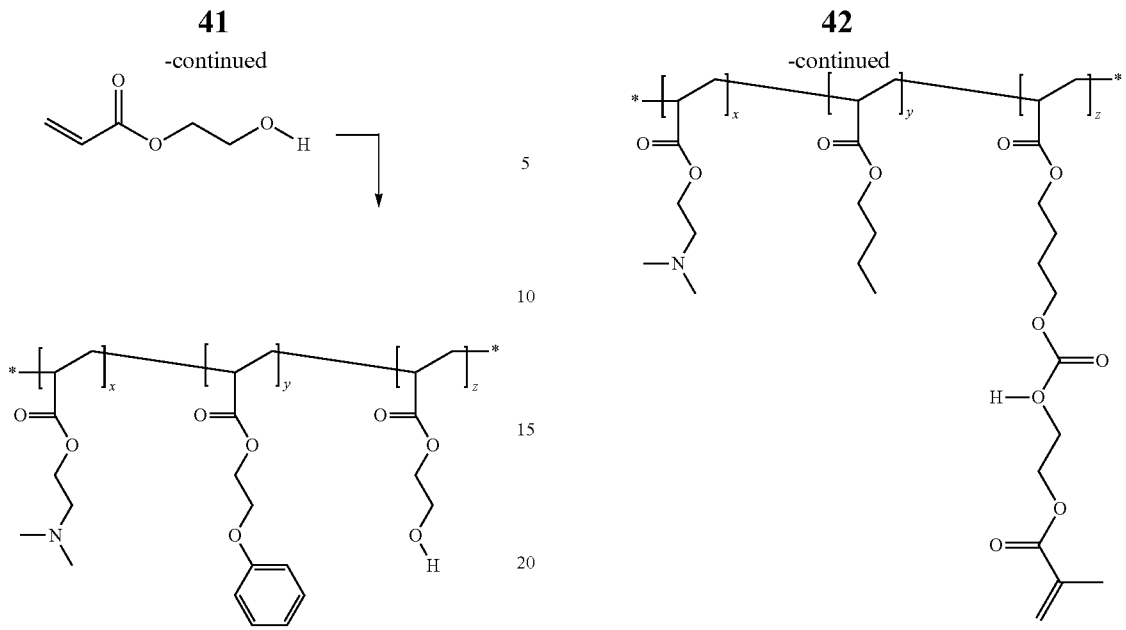

The terpolymer was prepared according to the General Procedure from 2-(N,N-dimethylamino)ethyl methacrylate (4.10 g, 26 mmol), 2-phenoxyethyl acrylate (43.45 g, 226.1 mmol), 2-hydroxyethyl methacrylate (HEMA, 3.38 g, 30 mmol, Alfa Aesar, Tewksbury, MA, 01876, USA). The product was isolated as a clear semi solid liquid.

Base 4

Methacrylation of 2-N,N-Dimethylaminoethyl methacrylate/n-butylacrylate/4-hydroxybutyl acrylate Terpolymer Synthesis using IEM.

The terpolymers (Base 1, 62 g, 145 calculated hydroxyl mmol equivalent weight) was placed in a glass jar then warmed up in an oven at around 60° C. IEM (17 g, 109.57 mmol, Showa Denko America Inc., New York, NY. USA) was added and mixed. After cooling to room temperature, dibutytin dilaurate (about 10 drops) was added and the mixture was hand mixed with a Teflon stick. The mixture was left to stand on bench at room temperature to give a semi solid product. Complete reaction of IEM was checked by recording IR spectroscopy.

Base 5

2-N,N-Dimethylaminoethyl acrylate/2-phenoxyethylacrylate/4-hydroxybutyl acrylate Terpolymer Synthesis

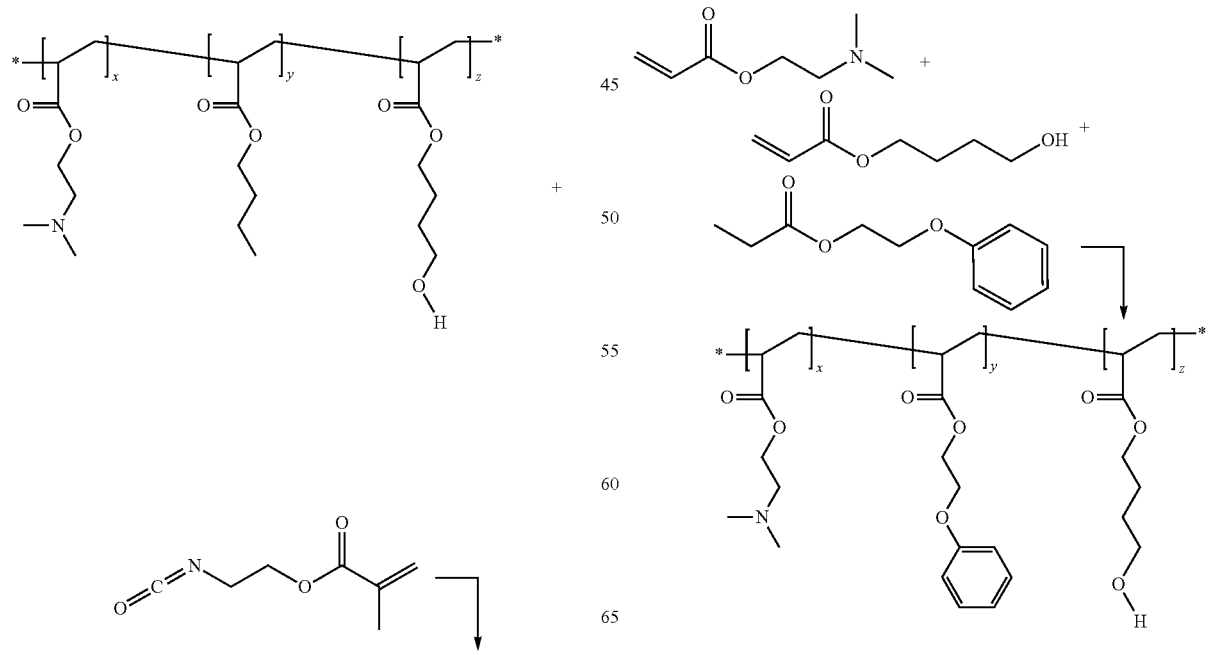

Synthesis of this terpolymer was done following the General Procedure in tetrahydrofuran (THF) as a solvent.

Base 6

2-N,N-Dimethylaminoethyl methacrylate/2-phenoxyethylacrylate/2-hydroxyethyl acrylate Terpolymer Synthesis

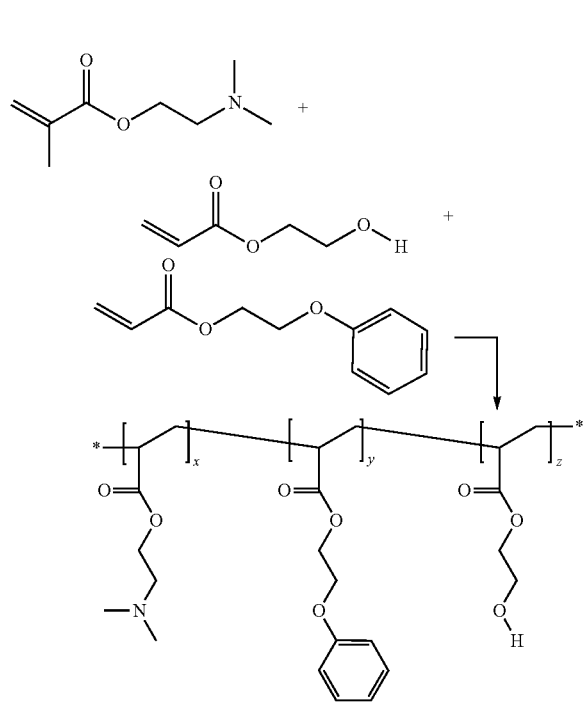

Synthesis of this terpolymer was done following the General Procedure in methyl ethyl ketone (MEK) and isopropyl alcohol as a solvent.

Basic Amine 7

Methacrylation of 2-N,N-Dimethylaminoethyl acrylate/2-hydroxyethyl acrylate/2-phenoxyethyl acrylate Terpolymer Synthesis using methacrylic anhydrid

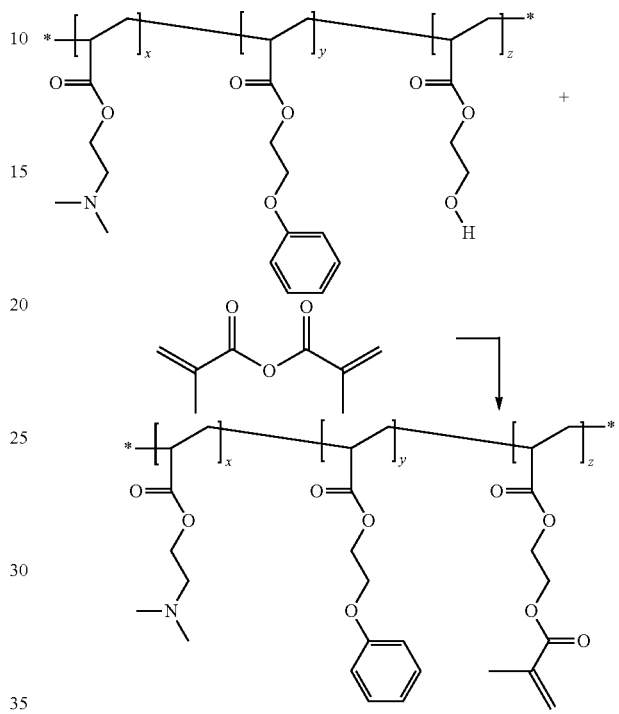

The General Procedure for Methacrylation was followed in the preparation of the methacrylated terpolymer above. The product was isolated as a viscous liquid.

TABLE 1

| Molar Ratios of Monomer Constituents of Ter-Polymer Basic Amines | | | | | | | |
|---|---|---|---|---|---|---|---|
| Component | Base 1 | Base 2 | Base 3 | Base 4 | Base 5 | Base 6 | Base 7 |
| 2-N,N-Dimethylaminoethyl methacrylate | 45 | 1 | 1 | 1 | | 50 | 50 |
| 2-N,N-Dimethylaminoethyl acrylate | | | | | 1 | | |
| 2-phenoxyethylacrylate | 45 | | 8 | | 1 | 40 | 40 |
| 2-t-butylaminoethyl methacrylate | 10 | | | | | | |
| 2-hydroxyethyl methacrylate | | | 1 | | | | |
| 4-hydroxybutyl acrylate | | 1 | | 1 | 1 | | |
| n-butylacrylate | | 1 | | 1 | | | |
| 2-hydroxyethyl acrylate | | | | | | 10 | 10 |
| IEM | | | | 75% OH | | | |
| methacrylic anhydride | | | | | | | 90% OH |

Intermediate 1

Preparation of tris(dibutylaminoglycidyl) isocyanurate

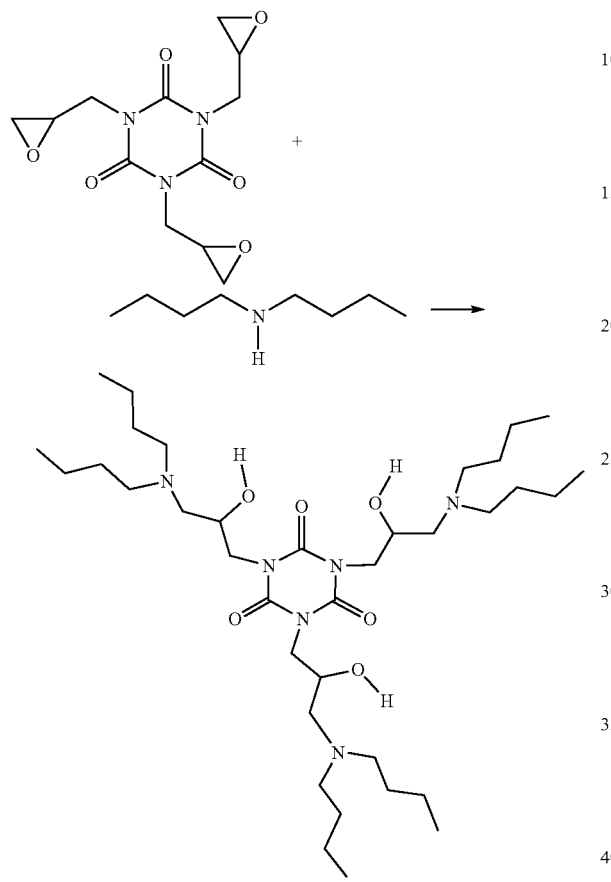

Isocyanuric triglycidyl ester (65.44 g, 220.1 mmol, TCI America, Portland, OR, USA) was suspended in ethanol (250 mL, DLI, King of Prussia, PA, USA) in a 500 mL 2-neck round bottom flask equipped with a magnetic stirring bar, a temperature controller, and condenser through which a nitrogen line was run into an oil bubbler. To the continuously stirred white suspension was added di-n-butylamine (85.27 g, 659.8 mmol, Alfa Aesar, Tewksbury, MA, 01876, USA). There as a mild exotherm upon addition. After stirring at room temperature for 15 minutes then temperature was raised slowly to 78° C. during which the mixture went from suspension to a light milky mix then a clear solution. The mixture was refluxed with continuous stirring for 2 days. The heat was turned off and, after cooling to room temperature, the solvent was removed in a rotary evaporator at 40-50° C. water bath temperature. The product was further dried in a vacuum oven overnight to give 137.5 g (90.85% yield) of a slightly hazy product. Product structure was confirmed by 1H NMR Intermediate 2

Preparation of tris(di-isobutylaminoglycidyl) Isocyanurate

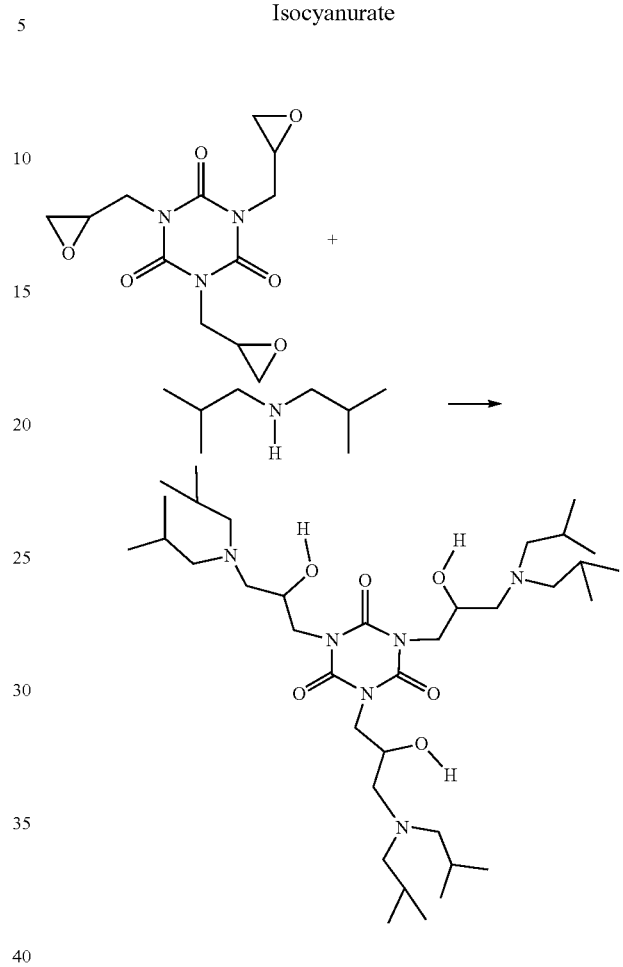

Intermediate 2 was prepared following the general preparatory procedure from Intermediate 1. Isocyanuric acid triglycidyl ester is available from TCI America (Portland, OR, USA). Di-isobutyl amine is available from Alfa Aesar (Tewksbury, MA, 01876, USA).

Intermediate 3

Preparation of Glycerol dimethacrylate glutaric acid mono-ester

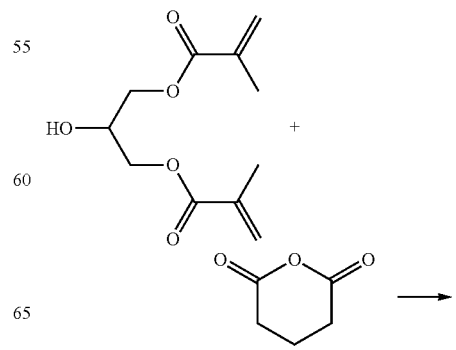

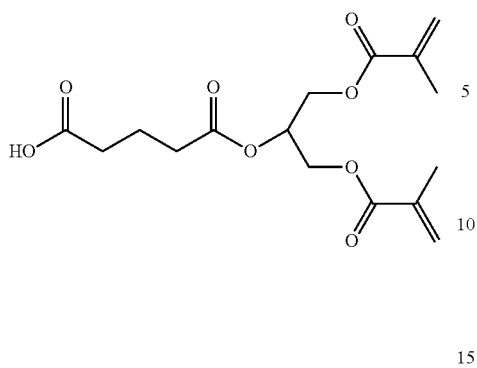

Glutaric anhydride (96 g, 841.37 mmol, Alfa Aesar, Tewksbury, MA. 01876, USA) and glycerol dimethacrylate (GDMA, 191.53 g, 839.16 mmol, TCI America, Portland. OR, USA) were charged into a 500 mL 3-neck flask equipped with a mechanical stirrer and a thermocouple. The flask contents were heated at 100° C. with a continuous stirring for 7 hours to give a light yellow/brown liquid. The structure of the product was confirmed by $^1$H NMR.

Basic Amine 8

Preparation of tris(dibutylaminoglycidyl) Isocyanurate tri-IEM

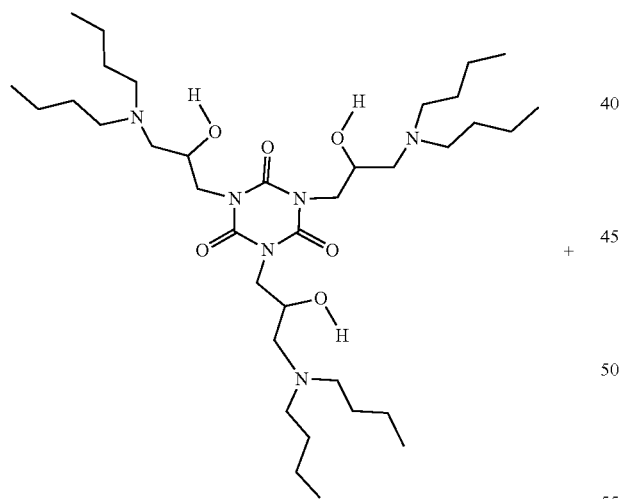

+

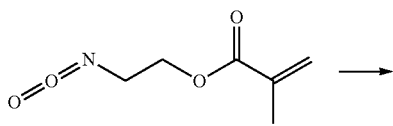

→

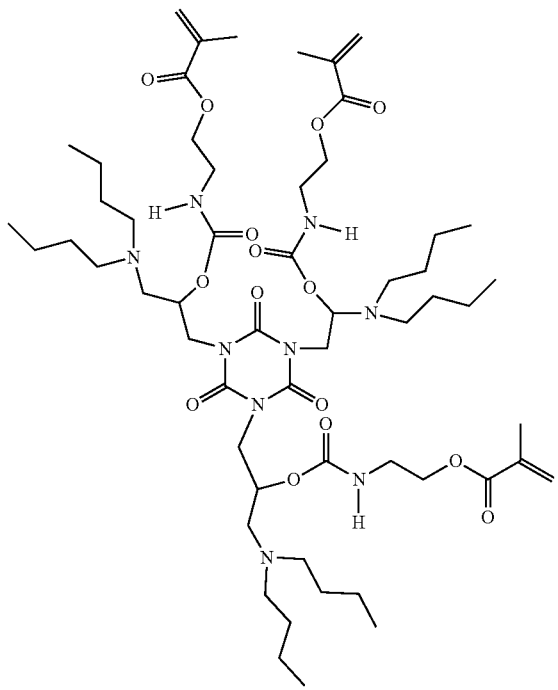

The isocyanuric acid ester triol (Intermediate 1, 180.98 g, 264.2 mmol) was placed in a glass jar. Dibutyltin dilaurate catalyst (1.5 g, 2.4 mml, Sigma Aldrich, St Louis, MO, USA) and BHT (0.3 g, 1 mmol, Sigma Aldrich, St Louis. MO, USA) were added and the contents were hand mixed using a Teflon stick. 2-Isocyanatoethyl methacrylate (IEM, 118 g, 760.55 mmol, Showa Denko America Inc., New York, NY, USA) was added in small increments with hand mixing for about 30 seconds. After the jar warms up in temperature then cools down, another IEM increment was added. This was repeated until complete IEM addition. The jar was then placed in an oven at 60° C. for 10 minutes followed by swirling. This was repeated multiple times.

IR was recorded and showed a complete disappearance of the isocyanate band around 2200-2400 cm$^{-1}$ $^1$H NMR was also recorded and was consistent with the methacrylate formation.

Basic Amine 9
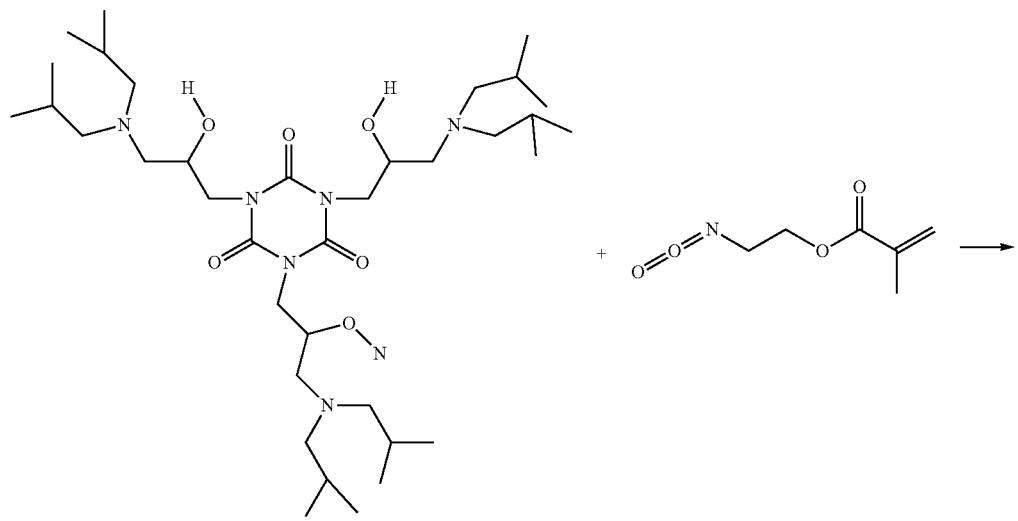
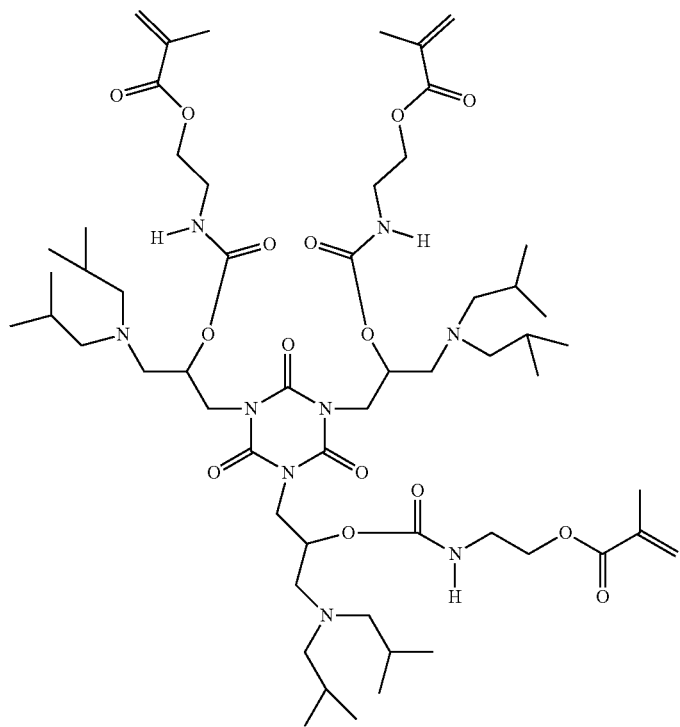
This trimer was prepared following the general preparatory procedure as described in Basic Amine 8. The reagents were tri-isobutylamine triol (Intermediate 2, 31 g. 45.22 mmol) and IEM (20 g, 128.91 mmol) in the presence of dibutyltin dilaurate catalyst and BHT inhibitor.

Basic Amine 10

Preparation of tris(dibutylaminoglycidyl) Isocyanurate hexamethacrylate

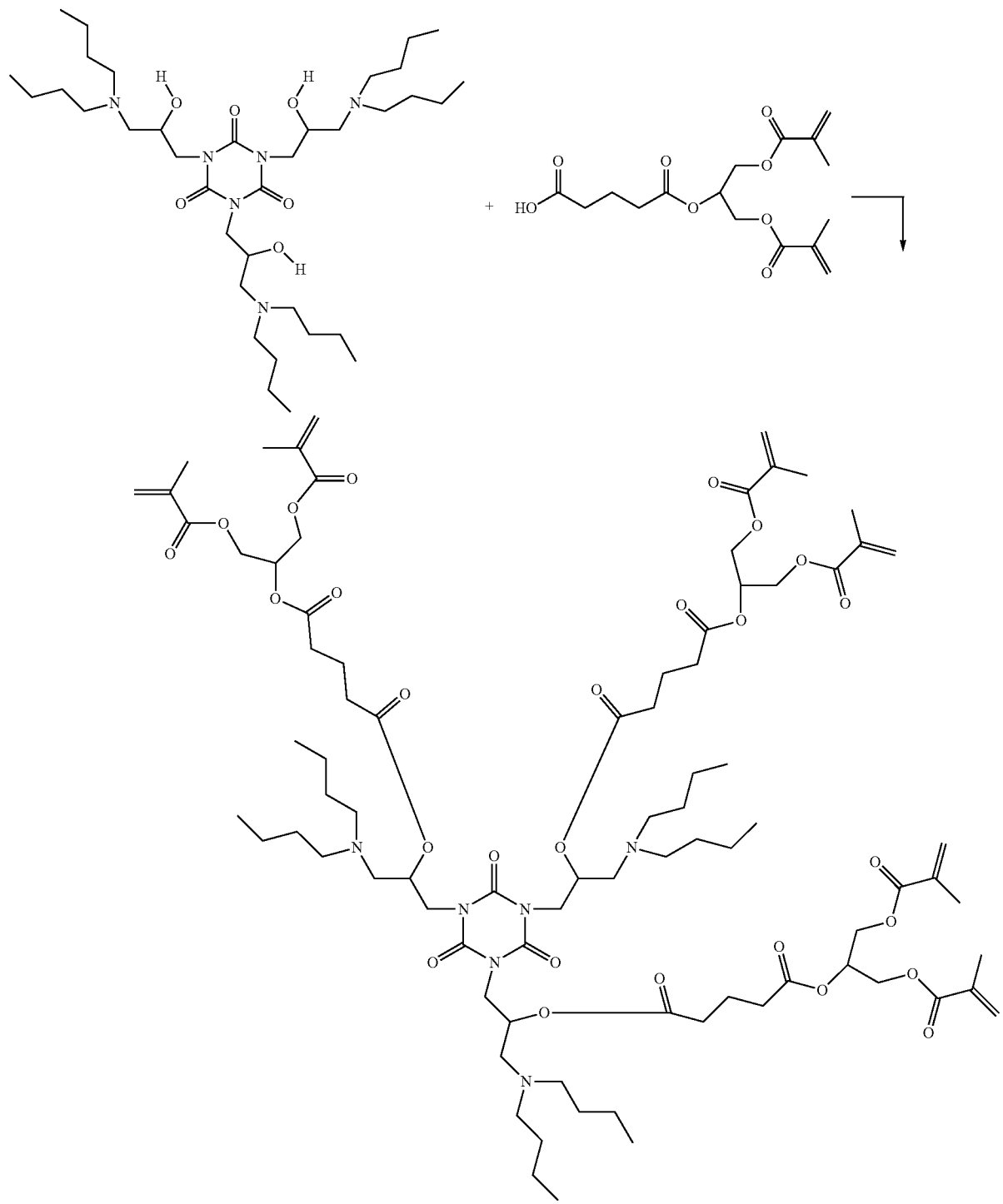

The preparatory procedure below describes the general procedure for esterification by dicyclohexy carbdiimide (DCC). This preparatory procedure will be referred to for other preparations. Tris(dibutylaminoglycidyl) Isocyanurate (Intermediate 1, 52.95 g, 77.30 mmol), glycerol dimethacrylate glutarate (79.5 g, 232 mmol Intermediate 3) and DMAP (1.5 g, 12 mmol, Novabiochem via EMD Millipore Corporation. Billerica, MA USA) were dissolved in ethyl acetate (500 mL, GFS Chemicals Inc., Powell, OH, USA) in a 2-liter 3-neck round bottom flask equipped with a mechanical stirrer, a nitrogen stream ending in an oil bubbler, a thermocouple, and dropping funnel. The mixture was cooled in an ice bath to 0-5° C. for 15 minutes. Dicyclohexyl carbodiimide (DCC, 47.6 g, 231 mmol, Alfa Aesar, Tewksbury, MA, 01876, USA) dissolved in 250 mL ethyl acetate was added to the continuously stirred mixture at cold with the temperature maintained at 0-10° C. during addition. After complete addition, stirring was continued at cold for 1-2 hours and at room temperature overnight.

The next day, the reaction was stopped and all solid formed was removed by vacuum filtration. The filtrate was extracted with 1N HCl (1×100 mL), 10% NaHCO$_3$ (1×100 mL) and water (1×100 mL). The organic layer was concentrated in a rotary evaporator. The obtained residue was left at room temperature overnight. Any crystalline solid formed was removed by filtration. The remaining viscous liquid was dried under vacuum with air-bleeding to give a yellow oil. NMR was recorded and found to be consistent with the desired product structure.

Basic Amine 11

Amine 11: Preparation of Polyamine Polyol Diacrylate

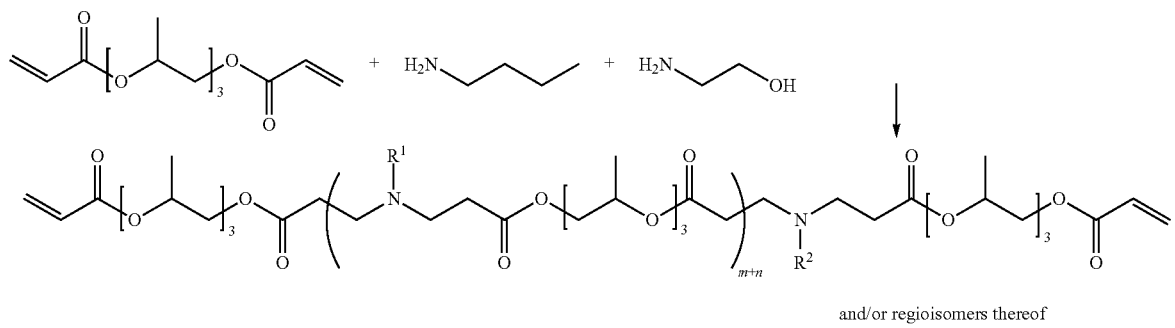

R$^1$ and R$^2$ are selected from ——CH$_2$CH$_2$CH$_2$CH$_3$ and ——CH$_2$CH$_2$OH; and
m+n = 9,
m corresponds to when R$^1$ is ——CH$_2$CH$_2$CH$_2$CH$_3$, and
n corresponds to when R$^1$ is ——CH$_2$CH$_2$OH
wherein when R$^1$ and R$^2$ is ——CH$_2$CH$_2$CH$_2$CH$_3$, m is 5
wherein when R$^1$ is ——CH$_2$CH$_2$CH$_2$CH$_3$ and R$^2$ is ——CH$_2$CH$_2$OH, m is 6

Tripropyleneoxide triacrylate (100 g, 332.9 mmol. Sigma-Aldrich Corp. St. Louis, MO), n-butylamine (13.27, 181.4 mmol, Alfa Aesar, Ward Hill, MA), 2-ethanolamine (7.4 g, 120 mmol, Alfa Aesar, Ward Hill, MA) where charged in a 500 mL glass jar. The components were continuously mixed with a mechanical stirrer. After 10 minutes, the mixture was heated to 55-60 C for 2 hours to give the product as a viscous amber color liquid.

Basic Amine 12 and 13

Preparation of Carboxylated Polyamine Polyol Amine 12 and 13

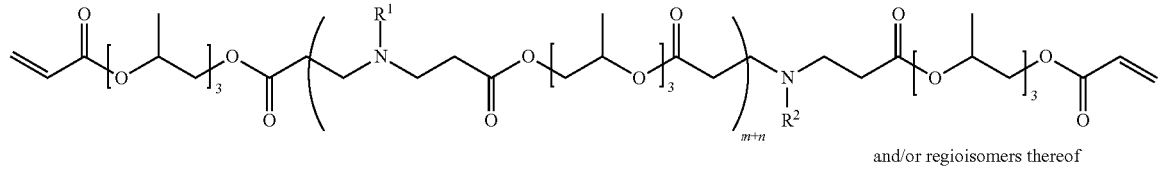

and/or regioisomers thereof

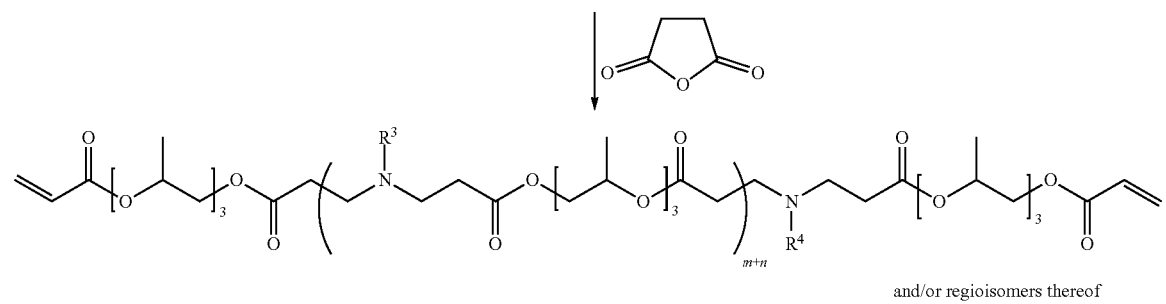

and/or regioisomers thereof $R^3$ and $R^4$ are selected from —$CH_2CH_2CH_2CH_3$— $CH_2CH_2OH$, and —$CH_2CH_2OC(O)CH_2CH_2C(O)OH$; and m+n=9, m corresponds to when $R^3$ is —$CH_2CH_2CH_2CH_3$, and n corresponds to when $R^3$ is —$CH_2CH_2OH$ or —$CH_2CH_2OC(O)CH_2CH_2C(O)OH$ wherein when $R^3$ and $R^4$ is —$CH_2CH_2CH_2CH_3$, m is 5 wherein when $R^3$ is —$CH_2CH_2CH_2CH$, and $R^4$ is —$CH_2CH_2OH$ or —$CH_2CH_2OC(O)CH_2CH_2C(O)OH$, m is 6

Basic Amine 12: less than 4 of $R^3$ and $R^4$ is —$CH_2CH_2OC(O)CH_2CH_2C(O)OH$ Basic Amine 13: each $R^3$ and $R^4$ is selected from —$CH_2CH_2CH_2CH_3$ and —$CH_2CH_2OC(O)CH_2CH_2C(O)OH$ Partial and complete carboxylation of aforementioned polyamine polyol (amine 11) were carried out by blending the polyamine polyol oligomer with succinic anhydride (Alfa Aesar, Ward Hill, MA) in a round bottom flask and continuously mixing using a mechanical stirrer at 90-100 C for 4 hours. Examples made according to the table 2.

TABLE 2

Carboxylation of Polyol

| | Amine 11: Polyamine polyol (g) | Polyamine polyol intermediate (OH mEq) | Succinic anhydride (g) | Succinic anhydride (mEq) |
|---|---|---|---|---|
| Amine 12 | 20.57 g | 20.6 | 0.52 | 5.2 |
| Amine 13 | 21.06 | 21.1 | 2.11 | 21.1 |

Preparatory Example 3: VEMA

VEMA

Preparation of 2-(2-vinyloxyethoxybonylamino)ethylmethacrylate (VEMA)

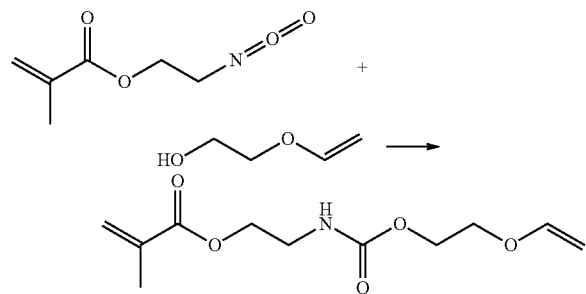

2-Vinyloxyethanol (22.9 g, 260 mmol, TCI America, Portland, OR, USA) was placed in a 150 mL glass jar followed by BHT, 0.05 g, 2-Isocyanatoethyl methacrylate (IEM, 40.3 g, 260 mmol, Showa Denko America Inc. New York, NY, USA) was added to the jar and hand mixed with a teflon stick, dibutyltin dilaurate catalyst (0.05 g, Alfa Aesar, Tewksbury, MA, 01876, USA) was added and the mixture was hand mixed for several minutes where it exothermed for a few minutes then cooled down to room temperature to give a colorless clear low viscosity liquid.

Reaction completion was confirmed by disappearance of the isocyanate band around 2250-2275 $cm^{-1}$ using an FTIR spectrophotometer. The structure of desired product was also confirmed by $^1H$ and $^{13}C$ NMR run on a 500 MHz NMR spectrophotometer.

Filler

"Filler 1" refers to zirconia-silica filler (which can be prepared as described in U.S. Pat. No. 6,624,211 B2 (Karim et al.) at column 15, line 60 through column 16, line 28) silane-treated in the following manner. Mix one hundred parts of the filler (average particle size 0.6-0.9 micrometers) with deionized water at a solution temperature of between 20-30° C. Adjust the pH1 of the resulting slurry to 3-3.3 with trifluoroacetic acid (0.278 parts). Add 7 parts (based on the one hundred parts of the filler) of 3-methacryloxypropyltrimethoxysilane (available from Wacker Chemie AG, Munich, Germany) to the slurry. Mix the slurry for 2 hours. At the end of 2 hours, neutralize the pH of the slurry with calcium hydroxide. Recover the Sf1' Zirconia/Silica by drying, crushing and screening through a 74-micron screen.

"Filler 2" refers to silica-zirconia nanocluster filler, prepared essentially as described in U.S. Pat. No. 6,730,156 B1 (Windisch et al.) at column 25, lines 50-63 (Preparatory Example A).

"Filler 3" refers to silane-treated silica-zirconia nanocluster filler, prepared essentially as described in U.S. Pat. No. 6,730,156 B1 (Windisch et al.) at column 25, lines 50-63 (Preparatory Example A) and at column 25, line 64 through column 26, line 40 (Preparatory Example B) with minor modifications, including performing the silanization in 1-methoxy-2-propanol (rather than water) adjusted to a pH of approximately 8.8 with $NH_4OH$ (rather than to a pH of 3-3.3 with trifluoroacetic acid), and obtaining the S/T Silica/Zirconia Clusters by gap drying (rather than spray drying).

"Filler 4" refers to amine functional surface treated filler 2.

Preparation of Filler 4:

Twenty five grams of filler 2 was added to a mixture of 25 g ethyl acetate and 2.625 g N-3[(amino(polypropyleneoxy)]aminopropyltrimethoxysilane 60 to 65% pure (Gelest, Morrisville, PA, Product Code SIA0599.4). Following this, 0.5 g of a 30 wt % aqueous ammonium hydroxide solution was added. This mixture was allowed to stir on a stir plate overnight to react (approximately 16 hours). The resulting mixture was dried in a solvent oven at 85-90° C. for 1.5 hours to produce the resultant filler.

Materials

"BisEMA-6" refers to ethoxylated (6 mole ethylene oxide) bisphenol A dimethacrylate, available from Sartomer Co., Inc. (Exton, PA) as "CD541";

"BisGMA" refers to 2,2-bis[4-(2-hydroxy-3-methacryloyloxypropoxy)phenyl]propane (also referred to as bisphenol A diglycidyl ether methacrylate), CAS Reg. No. 1565-94-2.

"BHT" refers to butylated hydroxytoluene (2,6-di-tert-butyl-4-methylphenol), CAS Reg. No. 128-37-0;

"BZT" refers to 2-(2'-hydroxy-5'-methacryloxyethylphenyl)-2H-benzotriazole, CAS Reg. No. 96478-09-0, available from Ciba, Inc. (Tarrytown, NY) as "TINUVIN R 796", also available from Sigma-Aldrich Corp. (St. Louis. MO):

"CPQ" refers to camphorquinone, CAS Reg. No. 10373-78-1;

"DCM" refers to dichloromethane, CAS Reg. No. 75-09-2, available from Acros Organics (Hampton, NH, USA);

"DMAP" refers to 4-(N,N-dimethylamino)pyridine, available from Alfa Aesar (Tewksbury, MA);

"DPIHFP" or "DPIPF6" or "DPI" refers to diphenyliodonium hexafluorophosphate, CAS Reg. No. 58109-40-3, available from Johnson Matthey, Alfa Aesar Division (Ward Hill, MA);

"EDMAB" refers to ethyl 4-dimethylaminobenzoate, CAS Reg. No. 10287-53-3;

"EDMAO" refers to 2 ethyl-9,10 dimethoxy anthracene, CAS Reg. No. 26708-04-3, available from Sigma-Aldrich Corp. (St. Louis, MO);

"GENIOSIL GF-31" or "GF-31" refers to 3-methacryloxypropyltrimethoxysilane, available from Wacker Chemie AG (Munich, Germany);

"HEMA" refers to 2-hydroxyethyl methacrylate, available from ESSTECH, Inc. (Essington, PA);

"IEM" refers to Isocyanatoethyl methacrylate, available from Showa Denko America Inc., New York, NY, USA;

"IRGACURE 819" refers to a bis(2,4,6-trimethylbenzoyl) phenylphosphine oxide photoinitiator, CAS Reg. No. 162881-26-7, available from Ciba Specialty Chemicals Corp. (Tarrytown, NY), also available from Sigma-Aldrich Corp. (St. Louis, MO);

"PHEMA" refers to phosphoric acid 2-hydroxyethyl methacrylate ester, CAS Reg. No. 52628-03-2, available from Sigma-Aldrich (St. Louis, MO);

"Procrylat" refers to 2,2-bis-4-(3-methacryloxypropoxy) phenyl)propane dimethacrylate, CAS Reg. No. 27689-12-9, as further described in WO2006/020760;

"SR-350" refers to trimethylolpropane trimethacrylate, CAS Reg. No. 3290-92-4, available from Sartomer Americas, Arkema Group (Exton, PA)

"TEGDMA" refers to triethyleneglycol dimethacrylate, CAS Reg. No. 109-16-0, available from Sartomer Co., Inc. (Exton, PA);

"THF" refers to tetrahydrofuran, Cas Reg. No. 109-99-9, available from Acros Organics (Hampton, NH, USA);

"TMPMP" refers to trimethylolpropane tris(3-mercaptopropionate), CAS Reg. No. 33007-83-9, available from Sigma-Aldrich (St. Louis, MO);

"UDMA" refers to diurethane dimethacrylate, CAS Reg. No. 72869-86-4, obtained under the trade designation "ROHAMERE 6661-0" from Rohm America LLC (Piscataway, NJ); also available from Dajac Laboratories (Trevose, PA);

"Carboxyethyl acrylate" refers to 2-carboxyethyl acrylate, CAS Reg. No. 24615-84-7, available from Sigma-Aldrich (St. Louis, MO);

Mono-2-methacryloyloxyethyl succinate CAS Reg. No. 20882-04-6, available from Sigma-Aldrich (St. Louis, MO);

Methacryloyloxyhexyl phosphate: Prepared essentially as described in Rusin, et, al: US20090208909A1 "YbF$_3$" refers to ytterbium fluoride, 100 nm particle size, available from Sukgyung AT Co. Ltd., (Korea);

"S/T 20 nm Silica" refers to silane-treated silica nanoparticle filler having a nominal particle size of approximately 20 nanometers, prepared essentially as described in U.S. Pat. No. 6,572,693 B1 (Wu et al.) at column 21, lines 63-67 (Nano-sized particle filler, Type #2);

"S/T 75 nm Silica" refers to silane-treated silica nanoparticle filler having a nominal particle size of approximately 75 nanometers, prepared essentially as described in U.S. Pat. No. 6,899,948 B2 (Zhang et al.) at column 31, lines 30-40 (Filler C);

Definitions 2-part formulation: In the exemplified 2-part formulations, they are referred to as the A-side or the B-side of the formulation, the A or B paste, the acid paste or base/amine containing paste, or any combination there-of. The A-side and B-side can be combined by hand, static mix tip or any assisted mechanical mixing.

Herein the term "flowable composite" or "flowable" refers to a pseudo-liquid that is filled with about 10% to about 80% filler. It has a characteristic viscosity such that it will yield and/or slump and/or flow under the stress of gravity or stress applied by hand when delivered in a syringe. It can be easily extruded through a small cannula. The viscosity is sufficiently low to allow its penetration into small undercuts as well as the ability to flow and adapt to the shape of the prepared tooth surface.

Herein the term "universal composite", "universal", "packable composite", "packable" or any variation thereof refers to a pseudo-liquid that is filled with about 10% to about 90% filler. It has a characteristic viscosity such that it will not substantially yield and/or slump after contouring under the stress of gravity.

Abbreviations

"cm" refers to centimeter;
"FT-ir" refers to Fourier Transform infrared spectroscopy;
"g" refers to gram;
"GPa" refers to giga pascals;
"h" or "hr" refers to hour;
"in" refers to inch;
"L" refers to liter;
"min" refers to minutes;
"mL" refers to milliliter;
"mm" refers to millimeter;
"mmol" refers to millimol;
"mEq" refers to milli-equivalence
"MPa" refers to mega pascals;
"NMR" refers to nuclear magnetic resonance;
"rpm" refers to revolutions per minute;
"sec" or "s" refers to seconds;

Test Methods

Consistency

Place a first 4 inch by 4 inch (10.2 centimeter by 10.2 centimeter) square glass plate on a stable, flat, level surface. Place 150±5 milligrams of test material at the center of the first glass plate. Place a second identical glass plate on top of the test material, pressing the test material between the two glass plates. Apply a weight such that the mass of the glass plate plus the weight is 1027±10 grams on top of the second glass plate to apply an even force to the test material for 120 seconds. Remove the weight and measure the diameter of the material film spread between the two plates. Measure the diameter in "consistency" units. One consistency unit is equal to 1/32 inch (0.031 inch=0.079 cm=0.79 mm).

Hand Mixing

Dispense about equal mass of A and B paste on 4 inch by 4 inch glass plate. Target 0.15 to 0.25 gram. Using a dental cement spatula, rapidly fold the two pastes together in a side to side mixing action in a small mixing area (approximately 1 inch diameter).

Stage Rank

Determined by trained operator when performing hand mixing method.

1=no observed stage
2=thickened, still sticky
3=thickened, soft, not sticky
4=ideal—similar to universal composite Diametral Tensile Strength Diametral tensile strength was measured per the following procedure. The uncured composite sample was injected into a glass that was about 30 mm long with a 4-mm inside diameter. It was filled about ½ full and capped with silicone rubber plugs. The tube was compressed axially at approximately 3 kg/cm$^2$ pressure for 5 minutes. While still under pressure, the sample was then light cured for 60 seconds by exposure to a dental curing light with a radiant exitance of greater than 1000 mW/cm$^2$. The tube was rotated as it cured to ensure equal exposure. A Buehler IsoMet 4000 (Illinois Tool Works, Lake Bluff, Illinois, USA) saw was then used to section disks about 2 mm thick from the tube. The resulting disks were stored in distilled water at 37° C. for about 24 hours prior to testing Measurements were carried out using an appropriate materials test frame (eg. Instron 5966, Instron Corp., Canton, MA) with a 10 kilonewton load cell at a crosshead speed of 1 mm per minute. Diametral tensile strength was calculate as describe in Craig's Restorative Dental Materials, (Ronals L. Sakaguchi and John M. Powers. "Testing of Dental Materials and Biomechanics." *Craig's Restorative Dental Materials*, thirteenth ed., Elsevier, 2012, p. 86). Results were reported in MPa.

Example 1

The following A-Side Pastes were prepared by the following procedure.

A BHT stabilized stock solution of bisGMA and TEGDMA was prepared. Examples of suitable acids, CPQ, Irgacure 819, DPIHFP and EDMOA were then dissolved in an aliquot of the stock solution. Once the resin was fully dissolved it was added to a mix cup. Then filler 1 was added on top of the resin. The mixture was mixed (DAC 150, Flacteck Inc, Landrum SC) 3 cycles of 1 minute at 3000 rpm to produce paste. Formulation Table 1-1 gives the formulations.

TABLE 1-1

Acid Containing Formulations

| | Formulation | | | | | | |
|---|---|---|---|---|---|---|---|
| Inventive Acid | EX 1-1A Acid 1 | EX 1-2A Acid 2 | EX 1-3A Acid 3 | EX 1-4A Acid 4 | EX 1-5A Acid 5 | EX 1-6A Acid 6 | EX 1-7A Acid 7 |
| Acid | 16.01% | 8.02% | 8.02% | 7.97% | 8.00% | 7.99% | 8.00% |
| BISGMA | 16.43% | 21.38% | 21.06% | 22.04% | 21.99% | 22.08% | 22.08% |
| TEGDMA | 7.05% | 10.06% | 10.44% | 9.45% | 9.43% | 9.41% | 9.41% |
| BHT | 0.06% | 0.06% | 0.06% | 0.06% | 0.06% | 0.06% | 0.06% |
| CPQ | 0.08% | 0.08% | 0.09% | 0.08% | 0.08% | 0.08% | 0.08% |
| Irgacure 819 | 0.20% | 0.20% | 0.20% | 0.20% | 0.20% | 0.20% | 0.20% |
| DPIHFP | 0.12% | 0.12% | 0.12% | 0.12% | 0.12% | 0.12% | 0.12% |
| EDMOA | 0.06% | 0.06% | 0.06% | 0.06% | 0.06% | 0.06% | 0.06% |
| Filler 1 | 59.99% | 60.02% | 59.95% | 60.02% | 60.06% | 60.00% | 59.99% |

The following B-Side Pastes were prepared by the following procedure.

A BHT stabilized stock solution of bisGMA and TEGDMA was prepared. Basic amine. CPQ, EDMAB, Irgacure 819 and EDMAO were dissolved in an aliquot of the stock solution. Once the resin was fully dissolved it was added to a mix cup. Then Filler 1 was added on top of the resin. The mixture was mixed (DAC 150, Flacteck Inc, Landrum SC) 3 cycles of 1 minute at 3000 rpm to produce paste. Formulation Table 1-2 gives the formulations.

TABLE 1-2

Basic Amine Containing Formulations

| | Formulation | | | | | |
|---|---|---|---|---|---|---|
| Inventive Amine | EX 1-1B Amine 1 | EX 1-2B Amine 2 | EX 1-3B Amine 3 | EX 1-4B Amine 4 | EX 1-5B Amine 5 | Comparative 1-1B Comparative |
| Amine | 7.69% | 8.02% | 7.98% | 8.11% | 8.00% | 0.00% |
| BISGMA | 21.85% | 21.62% | 21.65% | 21.54% | 21.63% | 27.22% |
| TEGDMA | 9.37% | 9.27% | 9.28% | 9.24% | 9.27% | 11.67% |
| BHT | 0.06% | 0.06% | 0.06% | 0.06% | 0.06% | 0.06% |
| CPQ | 0.08% | 0.08% | 0.08% | 0.08% | 0.08% | 0.08% |
| EDMAB | 0.70% | 0.70% | 0.70% | 0.70% | 0.70% | 0.70% |
| Irgacure 819 | 0.20% | 0.20% | 0.20% | 0.20% | 0.20% | 0.20% |
| EDMOA | 0.06% | 0.06% | 0.06% | 0.06% | 0.06% | 0.06% |
| Filler 1 | 59.99% | 59.99% | 59.99% | 60.01% | 60.00% | 60.01% |

Consistency of the individual A and B pastes were measured. Then, the A-side and B-side pastes were combined by placing an about equal mass of each on a glass plate, then mixing by hand spatulation (Test Method section HandMixing). Consistency of the combined paste was measured within about 5 minutes of bringing the A-side and B-side pastes together.

Table 1-3 demonstrates the decrease (thickening) in consistency when the two pastes are mixed. A material was considered staged when the consistency of the combined A-side+B-side paste was less than or equal to the arithmatic mean of the two input materials.

TABLE 1-3

Resulting Consistency upon Combining A and B Pastes

| Formulation | Paste | Individual consistency | Arithmetic mean consistency | Combined Consistency - Observed |
|---|---|---|---|---|
| Ex 1-1 | EX 1-1A | 38 | 37 | 32 |
|  | EX 1-1B | 36 |  |  |
| Ex 1-2 | EX 1-1A | 38 | 32 | 28 |
|  | EX 1-2B | 27 |  |  |
| Ex 1-3 | EX 1-1A | 38 | 40 | 43* |
|  | EX 1-3B | 43 |  |  |
| Ex 1-4 | EX 1-1A | 38 | 32 | 30 |
|  | EX 1-4B | 27 |  |  |
| Ex 1-5 | EX 1-1A | 38 | 39 | 38 |
|  | EX 1-5B | 40 |  |  |
| Comparative 1 | EX 1-1A | 38 | 44 | 44 |
|  | Comparative 1-1B | 49 |  |  |
| Ex 1-6 | EX 1-2A | 35 | 36 | 32 |
|  | EX 1-1B | 36 |  |  |
| Ex 1-7 | EX 1-2A | 35 | 31 | 30* |
|  | EX 1-2B | 27 |  |  |
| Ex 1-8 | EX 1-2A | 35 | 39 | 40* |
|  | EX 1-3B | 43 |  |  |
| Ex 1-9 | EX 1-2A | 35 | 31 | 31* |
|  | EX 1-4B | 27 |  |  |
| Ex 1-10 | EX 1-2A | 35 | 38 | 33 |
|  | EX 1-5B | 40 |  |  |
| Comparative 2 | EX 1-2A | 35 | 42 | 42 |
|  | Comparative 1-1B | 49 |  |  |
| Ex 1-11 | EX 1-3A | 35 | 35 | 27 |
|  | EX 1-1B | 36 |  |  |
| Ex 1-12 | EX 1-3A | 35 | 31 | 29 |
|  | EX 1-2B | 27 |  |  |
| Ex 1-13 | EX 1-3A | 35 | 39 | 40* |
|  | EX 1-3B | 43 |  |  |
| Ex 1-14 | EX 1-3A | 35 | 31 | 30 |
|  | EX 1-4B | 27 |  |  |
| Ex 1-15 | EX 1-3A | 35 | 37 | 33 |
|  | EX 1-5B | 40 |  |  |
| Comparative 3 | EX 1-3A | 35 | 42 | 40 |
|  | Comparative 1-1B | 49 |  |  |
| Ex 1-16 | EX 1-4A | 35 | 36 | 33 |
|  | EX 1-1B | 36 |  |  |
| Ex 1-17 | EX 1-4A | 35 | 31 | 29 |
|  | EX 1-2B | 27 |  |  |
| Ex 1-18 | EX 1-4A | 35 | 39 | 39* |
|  | EX 1-3B | 43 |  |  |
| Ex 1-19 | EX 1-4A | 35 | 31 | 30* |
|  | EX 1-4B | 27 |  |  |
| Ex 1-20 | EX 1-4A | 35 | 38 | 34 |
|  | EX 1-5B | 40 |  |  |
| Comparative 4 | EX 1-4A | 35 | 42 | 42 |
|  | Comparative 1-1B | 49 |  |  |
| Ex 1-21 | EX 1-5A | 34 | 35 | 32 |
|  | EX 1-1B | 36 |  |  |
| Ex 1-22 | EX 1-5A | 34 | 30 | 30 |
|  | EX 1-2B | 27 |  |  |
| Ex 1-23 | EX 1-5A | 34 | 38 | 41* |
|  | EX 1-3B | 43 |  |  |
| Ex 1-24 | EX 1-5A | 34 | 30 | 27 |
|  | EX 1-4B | 27 |  |  |
| Ex 1-25 | EX 1-5A | 34 | 37 | 34 |
|  | EX 1-5B | 40 |  |  |
| Comparative 5 | EX 1-5A | 34 | 42 | 40 |
|  | Comparative 1-1B | 49 |  |  |
| Ex 1-26 | EX 1-6A | 50 | 43 | 35 |
|  | EX 1-1B | 36 |  |  |
| Ex 1-27 | EX 1-6A | 50 | 38 | 31 |
|  | EX 1-2B | 27 |  |  |
| Ex 1-28 | EX 1-6A | 50 | 46 | 44 |
|  | EX 1-3B | 43 |  |  |
| Ex 1-29 | EX 1-6A | 50 | 38 | 32 |
|  | EX 1-4B | 27 |  |  |
| Ex 1-30 | EX 1-6A | 50 | 45 | 41 |
|  | EX 1-5B | 40 |  |  |
| Comparative 6 | EX 1-6A | 50 | 50 | 50 |
|  | Comparative 1-1B | 49 |  |  |
| Ex 1-31 | EX 1-7A | 37 | 36 | 33 |
|  | EX 1-1B | 36 |  |  |
| Ex 1-32 | EX 1-7A | 37 | 32 | 27 |
|  | EX 1-2B | 27 |  |  |
| Ex 1-33 | EX 1-7A | 37 | 40 | 41* |
|  | EX 1-3B | 43 |  |  |
| Ex 1-34 | EX 1-7A | 37 | 32 | 30 |
|  | EX 1-4B | 27 |  |  |
| Ex 1-35 | EX 1-7A | 37 | 38 | 36 |
|  | EX 1-5B | 40 |  |  |
| Comparative 7 | EX 1-7A | 37 | 43 | 43 |
|  | Comparative 1-1B | 49 |  |  |

*Staging behavior was not observed at given ratio of A/B and/or given concentration of A + B Example 2

The following A-Side Pastes were prepared by the following procedure.

A BHT stabilized stock solution of equal parts, Procrylat, TEGDMA and bisEMA6 was prepared. Examples of suitable acids were then dissolved in an aliquot of the stock solution. Photo initiators were not added to these resins because only staging behavior was of interest.

Once the resin was fully dissolved it was added to a mix cup. Then Filler 1 was added on top of the resin. The mixture was mixed (DAC 150, Flacteck Inc, Landrum SC) 3 cycles of 1 minute at 3000 rpm to produce paste. Formulation Table 2-1 gives the formulations.

TABLE 2-1

Acid Containing Formulations

Formulation

| Inventive Acid | EX 2-1A Acid 8 | EX 2-2A Acid 9 | EX 2-3A Acid 10 | EX 2-5A Acid 11 | EX 2-6A Acid 12 | EX 2-7A Acid 13 | EX 2-8A Acid 5 |
|---|---|---|---|---|---|---|---|
| ACID | 7.59% | 7.60% | 7.57% | 7.58% | 7.59% | 7.59% | 7.61% |
| Procrylat | 10.11% | 10.11% | 10.11% | 10.11% | 10.11% | 10.11% | 10.10% |
| TEGDMA | 10.11% | 10.11% | 10.11% | 10.11% | 10.12% | 10.11% | 10.11% |
| bisEMA6 | 10.14% | 10.14% | 10.14% | 10.14% | 10.15% | 10.14% | 10.13% |
| BHT | 0.05% | 0.05% | 0.05% | 0.05% | 0.05% | 0.05% | 0.05% |
| Filler 1 | 62.00% | 61.99% | 62.02% | 62.01% | 61.98% | 62.00% | 62.00% |

The following B-Side Pastes were prepared by the following procedure.

A BHT stabilized stock solution of equal parts, Procrylat, TEGDMA and bisEMA6 was prepared. Examples of suitable basic amines were then dissolved in an aliquot of the stock solution. Photo initiators were not added to these resins because only staging behavior was of interest. Once the resin was fully dissolved it was added to a mix cup. Then FILLER 1 was added on top of the resin. The mixture was mixed (DAC 150, Flacteck Inc, Landrum SC) 3 cycles of 1 minute at 3000 rpm to produce paste. Formulation Table 2-2 gives the formulations.

TABLE 2-2

Base Containing Formulations

| Formulation | EX 2-1B | EX 2-2B |
|---|---|---|
| Inventive Amine | Amine 7 | Amine 8 |
| BASE | 7.60% | 7.59% |
| Procrylat | 10.11% | 10.11% |
| TEGDMA | 10.11% | 10.11% |
| bisEMA6 | 10.14% | 10.14% |
| BHT | 0.05% | 0.05% |
| Filler 1 | 61.99% | 62.00% |

Consistency of the individual A and B pastes were measured. Then, the acid and base pastes were combined by placing an about equal mass of each on a glass plate, then mixing by hand spatulation. Consistency of the combined paste was measured within about 5 minutes of bringing the A-side and B-side pastes together.

Table 2-3 demonstrates the decrease in consistency (an increase in thickening) when the two pastes are mixed. A material was considered staged when the consistency of the combined A-side+B-side paste was less than or equal to the arithmatic mean of the two input materials.

TABLE 2-3

Resulting Consistency upon Combining A and B Pastes

| EXAMPLE (Ex) | Paste | Individual consistency | Arithmetic mean consistency | Combined Consistency - Observed |
|---|---|---|---|---|
| Ex 2-1 | EX 2-1A | 53 | 51 | 21 |
|  | EX 2-1B | 49 |  |  |
| Ex 2-2 | EX 2-1A | 53 | 47 | 29 |
|  | EX 2-2B | 40 |  |  |
| Ex 2-3 | EX 2-2A | 50 | 50 | 18 |
|  | EX 2-1B | 49 |  |  |
| Ex 2-4 | EX 2-2A | 50 | 45 | 30 |
|  | EX 2-2B | 40 |  |  |

TABLE 2-3-continued

Resulting Consistency upon Combining A and B Pastes

| EXAMPLE (Ex) | Paste | Individual consistency | Arithmetic mean consistency | Combined Consistency - Observed |
|---|---|---|---|---|
| Ex 2-5 | EX 2-3A | 50 | 50 | 30 |
|  | EX 2-1B | 49 |  |  |
| Ex 2-6 | EX 2-3A | 50 | 45 | 28 |
|  | EX 2-2B | 40 |  |  |
| Ex 2-7 | EX 2-4A | 41 | 45 | 42 |
|  | EX 2-1B | 49 |  |  |
| Ex 2-8 | EX 2-4A | 41 | 41 | 22 |
|  | EX 2-2B | 40 |  |  |
| Ex 2-9 | EX 2-5A | 48 | 49 | 28 |
|  | EX 2-1B | 49 |  |  |
| Ex 2-10 | EX 2-5A | 48 | 44 | 24 |
|  | EX 2-2B | 40 |  |  |
| Ex 2-11 | EX 2-6A | 46 | 48 | 28 |
|  | EX 2-1B | 49 |  |  |
| Ex 2-12 | EX 2-6A | 46 | 43 | 27 |
|  | EX 2-2B | 40 |  |  |
| Ex 2-13 | EX 2-7A | 48 | 49 | 18 |
|  | EX 2-1B | 49 |  |  |
| Ex 2-14 | EX 2-7A | 48 | 44 | 32 |
|  | EX 2-2B | 40 |  |  |
| Ex 2-15 | EX 2-8A | 42 | 45 | 34 |
|  | EX 2-1B | 49 |  |  |
| Ex 2-16 | EX 2-8A | 42 | 41 | 32 |
|  | EX 2-2B | 40 |  |  |

Example 3

A BHT stabilized stock solution of equal parts, Procrylat, TEGDMA, and bisEMA6 was prepared. Examples of acids, CPQ, DPIHFP and EDMOA were then dissolved in an aliquot of the stock solution. Once the resin was fully dissolved it was added to a mix cup. Then Filler 1 was added on top of the resin. The mixture was mixed (DAC 150. Flacteck Inc. Landrum SC) 3 cycles of 1 minute at 3000 rpm to produce paste. Formulation Table 3-1 gives the formulations.

TABLE 3-1

Acid Containing Formulations

| | Formulation | | | | |
|---|---|---|---|---|---|
| | EX 3-1A | EX 3-2A | EX 3-3A | EX 3-4A | Comparative 3-1A |
| Inventive Acid | Acid 5 | Acid 4 | Acid 10 | Acid 10 | Comparative |
| Acid | 7.00% | 6.94% | 5.22% | 3.48% | 0.00% |
| Procrylat | 9.22% | 9.24% | 9.81% | 10.39% | 11.54% |
| TEGDMA | 9.23% | 9.25% | 9.82% | 10.39% | 11.55% |
| bisEMA6 | 9.22% | 9.25% | 9.82% | 10.40% | 11.55% |
| BHT | 0.04% | 0.04% | 0.04% | 0.05% | 0.05% |
| CPQ | 0.09% | 0.09% | 0.09% | 0.09% | 0.09% |
| DPIHFP | 0.13% | 0.13% | 0.13% | 0.13% | 0.13% |
| EDMOA | 0.07% | 0.07% | 0.07% | 0.07% | 0.07% |
| Filler 1 | 65.00% | 64.99% | 65.00% | 65.00% | 65.02% |

The following B-Side Pastes were prepared by the following procedure.

A BHT stabilized stock solution of equal parts, Procrylat, TEGDMA, and bisEMA6 was prepared. Basic amine, CPQ, EDMAB, and EDMAO were dissolved in an aliquot of the stock solution. Once the resin was fully dissolved it was added to a mix cup. Then Filler 1 was added on top of the resin. The mixture was mixed (DAC 150, Flacteck Inc, Landrum SC) 3 cycles of 1 minute at 3000 rpm to produce paste. Table 3-2 gives the formulations.

TABLE 3-2

Basic Amine Containing Formulations

| | Formulation | | | | | |
|---|---|---|---|---|---|---|
| Inventive Base | EX 3-1B Amine 7 | EX 3-2B Base 6 | EX 3-3B Amine 8 | EX 3-4B Amine 8 | EX 3-5B Amine 7 | Comparative 3-1B Comparative |
| Base | 6.90% | 6.83% | 5.24% | 6.90% | 5.25% | 0.00% |
| Procrylat | 9.07% | 9.09% | 9.64% | 9.07% | 9.63% | 11.42% |
| TEGDMA | 9.07% | 9.09% | 9.64% | 9.07% | 9.64% | 11.42% |
| bisEMA6 | 9.10% | 9.12% | 9.67% | 9.10% | 9.66% | 11.45% |
| BHT | 0.04% | 0.04% | 0.04% | 0.04% | 0.04% | 0.05% |
| CPQ | 0.07% | 0.07% | 0.07% | 0.07% | 0.07% | 0.07% |
| EDMAB | 0.70% | 0.70% | 0.66% | 0.70% | 0.66% | 0.53% |
| EDMOA | 0.05% | 0.05% | 0.05% | 0.05% | 0.05% | 0.05% |
| Filler 1 | 65.00% | 65.01% | 64.99% | 65.00% | 65.00% | 65.01% |

Consistency of the individual A-side and B-side pastes were measured. Then, the acid and base pastes were combined by placing about an equal mass of each on a glass plate, then mixing by hand spatulation (Test Method section HandMixing). Consistency of the combined paste was measured within about 5 minutes of bringing the A-side and B-side pastes together.

Select examples were tested for diametral tensile strength. Combinations of A and B pastes were combined in an about 1:1 ratio by mass. About 2 g of each paste was placed on a 4 inch by 4 inch glass plate. The two materials were hand mixed with a dental cement spatula until the material was fully mixed. After mixing the staged materials were loaded into syringes, de-gassed, and diametral tensile strength samples were prepared and tested as described in the test method section.

Results Table 3-3 shows the consistency of the individual pastes, the consistency of the A+B paste, and the diametral tensile strength of the combined materials.

TABLE 3-3

Resulting Consistency and Diametral Tensile Strength Upon Combining A + B Pastes

| EXAMPLE (Ex) | Paste: | Individual consistency | Arithmetic mean consistency | Combined Consistency - Observed | Diametral Tensile Strength (MPa) |
|---|---|---|---|---|---|
| Ex 3-1 | EX 3-1A | 38 | 38 | 20 | 47 |
| | EX 3-1B | 38 | | | |
| Ex 3-2 | EX 3-1A | 38 | 41 | 21 | — |
| | EX 3-2B | 44 | | | |
| Ex 3-3 | EX 3-1A | 38 | 40 | 37 | 59 |
| | EX 3-4B | 42 | | | |
| Ex 3-4 | EX 3-2A | 41 | 40 | 22 | — |
| | EX 3-1B | 38 | | | |
| Ex 3-5 | EX 3-2A | 41 | 43 | 24 | — |
| | EX 3-2B | 44 | | | |
| Ex 3-6 | EX 3-2A | 41 | 41 | 38 | — |
| | EX 3-4B | 42 | | | |
| Ex 3-7 | EX 3-3A | — | — | — | 71 |
| | EX 3-3B | — | | | |
| Ex 3-8 | EX 3-4A | 40 | 39 | 14 | — |
| | EX 3-1B | 38 | | | |
| Ex 3-9 | EX 3-4A | 40 | 42 | 13 | — |
| | EX 3-2B | 44 | | | |
| Ex 3-10 | EX 3-4A | 40.0 | 41 | 19 | — |
| | EX 3-4B | 42.0 | | | |
| Ex 3-11 | EX 3-4A | 40.0 | — | — | 59 |
| | EX 3-5B | — | | | |

TABLE 3-3-continued

Resulting Consistency and Diametral Tensile Strength Upon Combining A + B Pastes

| EXAMPLE (Ex) | Paste: | Individual consistency | Arithmetic mean consistency | Combined Consistency - Observed | Diametral Tensile Strength (MPa) |
|---|---|---|---|---|---|
| Comparative | Comparative 3-1A | 46 | 47 | 45 | 82 |
| | Comparative 3-1B | 48 | | | |

Example 4

The following A-Side Pastes were prepared by the following procedure.

A BHT stabilized stock solution of equal parts, Procrylat, TEGDMA, and bisEMA6 was prepared. Acid, CPQ, DPIHFP and EDMOA were then dissolved in an aliquot of the stock solution. Once the resin was fully dissolved it was added to a mix cup. Then filler 1 was added on top of the resin. The mixture was mixed (DAC 150, Flacteck Inc, Landrum SC) 3 cycles of 1 minute at 3000 rpm to produce paste. Table 4-1 gives the formulations.

TABLE 4-1

Acid Containing Formulations

| Formulation | EX 4-1A | EX 4-2A | EX 4-3A |
|---|---|---|---|
| Inventive Acid | Acid 10 | Acid 12 | Acid 9 |
| Acid | 5.10% | 3.66% | 3.44% |
| Procrylat | 9.86% | 10.34% | 10.42% |
| TEGDMA | 9.86% | 10.34% | 10.42% |
| bisEMA6 | 9.87% | 10.34% | 10.42% |
| BHT | 0.04% | 0.05% | 0.05% |
| CPQ | 0.07% | 0.07% | 0.07% |
| DPIHFP | 0.14% | 0.14% | 0.14% |
| EDMOA | 0.05% | 0.05% | 0.05% |
| Filler 1 | 65.01% | 65.01% | 64.99% |

The following B-Side Pastes were prepared by the following procedure.

A BHT stabilized stock solution of equal parts, Procrylat, TEGDMA, and bisEMA6 was prepared. Basic amine, CPQ, EDMAB, and EDMAO were dissolved in an aliquot of the stock solution. Once the resin was fully dissolved it was added to a mix cup. Then Filler 1 was added on top of the resin. The mixture was mixed (DAC 150, Flacteck Inc, Landrum SC) 3 cycles of 1 minute at 3000 rpm to produce paste. Table 4-2 gives the formulations.

TABLE 4-2

Basic Amine Containing Formulations

| Formulations | EX 4-1B | EX 4-2B | EX 4-3B |
|---|---|---|---|
| Inventive Amine | Amine 8 | Amine 9 | Amine 10 |
| Amine | 6.04% | 6.02% | 8.53% |
| Procrylat | 9.37% | 9.38% | 8.54% |
| TEGDMA | 9.36% | 9.37% | 8.53% |
| bisEMA6 | 9.36% | 9.37% | 8.53% |
| BHT | 0.04% | 0.04% | 0.04% |
| CPQ | 0.07% | 0.07% | 0.07% |
| EDMAB | 0.70% | 0.70% | 0.70% |
| EDMOA | 0.05% | 0.05% | 0.05% |
| Filler 1 | 65.01% | 65.00% | 65.01% |

Consistency was measured of individual A and B pastes. Then, the acid and base pastes were combined by placing about an equal mass of each on a glass plate, then mixing by hand spatulation (Test Method section Hand Mixing). Consistency of the combined paste was measured within about 5 minutes of bringing the A-side and B-side pastes together.

A-side and B-side combinations were prepared for diametral tensile strength testing. Since it was such a large quantity of material needed, they were combined in a speed mixer cup and mixed for 20 seconds at 2500 rpm. After mixing the staged materials were loaded into syringes, de-gassed, and diametral tensile strength samples were prepared and tested.

Results Table 4-3 shows the consistency of the individual pastes, and the consistency of the A+B paste, and the diametral tensile strength of the combined materials.

TABLE 4-3

Resulting Consistency and Diametral Tensile Strength Upon Combining A + B Pastes

| EXAMPLE (Ex) | Paste: | Individual consistency | Arithmetic mean consistency | Combined Consistency - Observed | Diametral Tensile Strength (MPa) |
|---|---|---|---|---|---|
| Ex 4-1 | EX 4-1A | 42 | 44 | 15.5 | 68.7 |
|  | EX 4-1B | 46 |  |  |  |
| Ex 4-2 | EX 4-1A | 42 | 44 | 23.8 | 65.4 |
|  | EX 4-2B | 46 |  |  |  |
| Ex 4-3 | EX 4-1A | 42 | 50 | 18.5 | 70.5 |
|  | EX 4-3B | 58 |  |  |  |
| Ex 4-4 | EX 4-2A | 43 | 45 | 16.0 | 63.9 |
|  | EX 4-1B | 46 |  |  |  |
| Ex 4-5 | EX 4-2A | 43 | 45 | 23.5 | 63.3 |
|  | EX 4-2B | 46 |  |  |  |
| Ex 4-6 | EX 4-2A | 43 | 50 | 17.8 | 61.2 |
|  | EX 4-3B | 58 |  |  |  |
| Ex 4-7 | EX 4-3A | 45 | 45 | 19.0 | 61.8 |
|  | EX 4-1B | 45 |  |  |  |
| Ex 4-8 | EX 4-3A | 45 | 46 | 24.5 | 66.7 |
|  | EX 4-2B | 46 |  |  |  |
| Ex 4-9 | EX 4-3A | 45 | 51 | 22.5 | 67.9 |
|  | EX 4-3B | 58 |  |  |  |
| Comparative | Filtek Supreme Ultra Flowable | 44.0 | — | — | 68.0 |
| Comparative | Filtek Bulk Fill Posterior | 15.3 | — | — | — |

It can be seen from the data in Table 14: Consistency that the individual A or B pastes had a consistency similar to the commercially available flowable composite and the A+B pastes had a consistency similar to the self supporting/sculptable composite. It can also be seen that diametral tensile strength was similar to that of a commercially available composite.

Example 5

The following formulations were prepared to demonstrate that a non-carboxylic, such as phosphoric acid could be used to stage materials.

The following A-Pastes were prepared by the following procedures.

A BHT stabilized stock solution of equal parts, Procrylat, TEGDMA, and bisEMA6 was prepared. Acid PHEMA, CPQ, DPIHFP and EDMOA were then dissolved in an aliquot of the stock solution. Once the resin was fully dissolved it was added to a mix cup. Then Filler 1 was added on top of the resin. The mixture was mixed (DAC 150, Flacteck Inc. Landrum SC) 3 cycles of 1 minute at 3000 rpm to produce paste. Table 5-1 gives the formulations.

TABLE 5-1

Acid Containing Formulations

| Ingredient | EX 5-1A | EX 5-2A |
|---|---|---|
| PHEMA | 8.23% | 4.40% |
| TEGDMA | 8.82% | 9.42% |
| BisEMA6 | 8.82% | 9.42% |

TABLE 5-1-continued

Acid Containing Formulations

| Ingredient | EX 5-1A | EX 5-2A |
|---|---|---|
| Procrylat | 8.82% | 9.42% |
| BHT | 0.04% | 0.04% |
| CPQ | 0.08% | 0.09% |
| DPIHFP | 0.13% | 0.14% |
| EDMOA | 0.06% | 0.07% |
| Filler 1 | 65.00% | 67.00% |

The following B-Pastes were prepared by the following procedure.

A BHT stabilized stock solution of equal parts, Procrylat, TEGDMA, and bisEMA6 was prepared. Amine 8, CPQ, EDMAB, and EDMOA were dissolved in an aliquot of the stock solution. Once the resin was fully dissolved it was added to a mix cup. Then Filler 1 or Filler 4 was added on top of the resin. The mixture was mixed (DAC 150, Flacteck Inc, Landrum SC) 3 cycles of 1 minute at 3000 rpm to produce paste. Table 5-2 gives the formulations.

TABLE 5-2

Basic Amine Containing Formulations

| Ingredient | EX 5-1B | EX 5-2B |
|---|---|---|
| Basic Amine 8 | 6.90% | 6.90% |
| TEGDMA | 9.07% | 9.07% |
| BisEMA6 | 9.10% | 9.10% |
| Procrylat | 9.07% | 9.07% |
| BHT | 0.04% | 0.04% |
| CPQ | 0.07% | 0.07% |
| EDMAB | 0.70% | 0.70% |
| EDMOA | 0.05% | 0.05% |
| Filler 1 | 65.00% | — |
| Filler 4 | — | 65.00% |

Consistency of the individual A-side and B-side pastes were measured. Then, the A and B pastes were combined by placing about an equal mass of each on a glass plate, then mixing by hand spatulation (Test Method section Hand Mixing). Consistency of the combined paste was measured within about 5 minutes of bringing the A-side and B-side pastes together.

Next, all combinations of A and B pastes were combined in a 1:1 ratio by mass. Since a large quantity of material needed, they were combined in a mix cup and mixed (DAC 150, Flacteck Inc. Landrum SC) for 20 seconds at 2500 rpm. After mixing the staged materials were loaded into syringes, de-gassed, and diametral tensile strength samples were prepared and tested.

Table 5-3 shows the consistency of the individual pastes, the consistency of A+B paste, and the diametral tensile strength of the combined materials after it was hardened to its final stage by irradiation.

TABLE 5-3

Resulting Consistency and Diametral Tensile Strength Upon Combining A + B Pastes

| Example (Ex) | Paste: | Individual consistency | Arithmetic mean consistency | Combined Consistency - Observed | Diametral Tensile Strength (MPa) |
|---|---|---|---|---|---|
| Ex 5-1 | Ex 5-1A | 42 | 41 | 22 | 58 |
|  | Ex 5-1B | 40 |  |  |  |
| Ex 5-2 | Ex 5-1A | 42 | 41 | 20 | 56 |
|  | Ex 5-2B | 40 |  |  |  |
| Ex 5-3 | Ex 5-2A | 42 | 41 | 18 | 65 |
|  | Ex 5-1B | 40 |  |  |  |
| Ex 5-4 | Ex 5-2A | 42 | 41 | 20 | 63 |
|  | Ex 5-2B | 40 |  |  |  |
| Comparative | Filtek Supreme Ultra Flowable | 44 | — | — | 68 |
| Comparative | Filtek Bulk Fill Posterior | 15 | — | — | — |

Example 6

The following A-Side Pastes were prepared by the following procedure.

A BHT stabilized stock solution of TEGDMA and bisEMA6 was prepared. The acid was then dissolved in an aliquot of the stock solution. Photo initiators were not added to these resins because only staging behavior was of interest. Once the resin was fully dissolved it was added to a mix cup. Then filler 3 and S/T 20 nmn silica were added on top of the resin. The mixture was mixed (DAC 150, Flacteck Inc, Landrum SC) 3 cycles of 1 minute at 3000 rpm to produce paste. Table 6-1 gives the formulations.

TABLE 6-1

Acid Containing Formulations

| | Formulation | | | | | |
|---|---|---|---|---|---|---|
| Inventive Acid | EX 6-1A Acid 10 | Ex 6-2A Acid 10 | Ex 6-3A Acid 10 | Ex 6-4A Acid 14 | Ex 6-5A Acid 14 | Ex 6-6A Acid 14 |
| Acid | 4.99% | 7.00% | 9.00% | 5.00% | 6.99% | 8.00% |
| bisEMA6 | 20.97% | 19.57% | 18.17% | 20.97% | 19.58% | 18.87% |
| TEGDMA | 8.99% | 8.39% | 7.79% | 8.99% | 8.39% | 8.09% |
| BHT | 0.05% | 0.04% | 0.04% | 0.04% | 0.04% | 0.04% |
| Filler 3 | 58.50% | 58.50% | 58.50% | 58.50% | 58.50% | 58.50% |
| S/T 20 nm Silica | 6.50% | 6.50% | 6.50% | 6.50% | 6.50% | 6.50% |

The following B-Pastes were prepared by the following procedure.

A stock solution of bisGMA, TEGDMA and BHT was prepared. Photo initiators were not added to these resins because only staging behavior was of interest. The resin and inventive basic amine was added to a mix cup. They were mixed for 1 min at 1500 rpm. Then Filler 3 and S/T 20 nm Silica was added on top of the resin. The components were mixed (DAC 150, Flacteck Inc, Landrum SC) 3 cycles of 1 minute at 3000 rpm to produce paste. Table 6-2 gives the formulations.

TABLE 6-2

Basic Amine Containing Formulations

| Inventive Basic Amine | EX 6-1B Amine 11 | Ex 6-2B Amine 12 | Ex 6-3B Amine 12 | Ex 6-4B Amine 12 | Ex 6-5B Amine 13 | Ex 6-6B Amine 13 | Ex 6-7B Amine 13 |
|---|---|---|---|---|---|---|---|
| Amine | 7.00% | 5.01% | 7.00% | 9.00% | 5.00% | 7.00% | 8.00% |
| bisEMA6 | 19.58% | 20.98% | 19.58% | 18.12% | 20.98% | 19.59% | 18.87% |
| TEGDMA | 8.38% | 8.97% | 8.38% | 7.78% | 8.98% | 8.37% | 8.09% |
| BHT | 0.04% | 0.04% | 0.04% | 0.04% | 0.04% | 0.04% | 0.04% |
| Filler 3 | 58.49% | 58.50% | 58.49% | 58.50% | 58.50% | 58.50% | 58.50% |
| S/T 20 nm Silica | 6.50% | 6.50% | 6.50% | 6.50% | 6.50% | 6.50% | 6.50% |

Consistency was measured of individual A and B pastes. Then, aliquots of equal mass A and B were combined. Table 6-3 shows the consistency of the individual pastes, and the consistency of the A+B paste.

TABLE 6-3

Resulting Consistency Upon Combining A + B Pastes

| Example | Paste | Individual consistency | Arithmetic mean consistency | Combined Consistency - Observed |
|---|---|---|---|---|
| Ex 6-1 | Ex 6-1A | 33.0 | 36.8* | 41.0 |
|  | Ex 6-2B | 40.5 |  |  |
| Ex 6-2 | Ex 6-1A | 33.0 | 36.5 | 33.5 |
|  | Ex 6-3B | 40.0 |  |  |
| Ex 6-3 | Ex 6-1A | 33.0 | 36.8 | 30.0 |
|  | Ex 6-4B | 38.5 |  |  |
| Ex 6-4 | Ex 6-1A | 33.0 | 34.5 | 32.5 |
|  | Ex 6-5B | 36.0 |  |  |
| Ex 6-5 | Ex 6-1A | 33.0 | 34.0 | 31.0 |
|  | Ex 6-6B | 35.0 |  |  |
| Ex 6-6 | Ex 6-1A | 33.0 | 32.5 | 27.0 |
|  | Ex 6-7B | 32.0 |  |  |
| Ex 6-7 | Ex 6-2A | 31.5 | 34 | 26.0 |
|  | Ex 6-1B | 36.5 |  |  |
| Ex 6-8 | Ex 6-2A | 31.5 | 36.0 | 30.0 |
|  | Ex 6-2B | 40.5 |  |  |
| Ex 6-9 | Ex 6-2A | 31.5 | 35.8 | 26.0 |
|  | Ex 6-3B | 40.0 |  |  |
| Ex 6-10 | Ex 6-2A | 31.5 | 35.0 | 24.5 |
|  | Ex 6-4B | 38.5 |  |  |
| Ex 6-11 | Ex 6-2A | 31.5 | 33.8 | 27.0 |
|  | Ex 6-5B | 36.0 |  |  |
| Ex 6-12 | Ex 6-2A | 31.5 | 33.3 | 24.5 |
|  | Ex 6-6B | 35.0 |  |  |
| Ex 6-13 | Ex 6-2A | 31.5 | 31.8 | 22.0 |
|  | Ex 6-7B | 32.0 |  |  |
| Ex 6-14 | Ex 6-3A | 29.0 | 34.8 | 23.0 |
|  | Ex 6-2B | 40.5 |  |  |
| Ex 6-15 | Ex 6-3A | 29.0 | 34.5 | 22.5 |
|  | Ex 6-3B | 40.0 |  |  |
| Ex 6-16 | Ex 6-3A | 29.0 | 33.8 | 21.5 |
|  | Ex 6-4B | 38.5 |  |  |
| Ex 6-17 | Ex 6-3A | 29.0 | 32.5 | 22.0 |
|  | Ex 6-5B | 36.0 |  |  |
| Ex 6-18 | Ex 6-3A | 29.0 | 32.0 | 19.0 |
|  | Ex 6-6B | 35.0 |  |  |
| Ex 6-19 | Ex 6-3A | 29.0 | 30.5 | 19.5 |
|  | Ex 6-7B | 32.0 |  |  |
| Ex 6-20 | Ex 6-4A | 37.0 | 38.8 | 34.5 |
|  | Ex 6-2B | 40.5 |  |  |
| Ex 6-21 | Ex 6-4A | 37.0 | 38.5 | 32.5 |
|  | Ex 6-3B | 40.0 |  |  |
| Ex 6-22 | Ex 6-4A | 37.0 | 37.8 | 27.5 |
|  | Ex 6-4B | 38.5 |  |  |
| Ex 6-23 | Ex 6-4A | 37.0 | 36.5 | 28.5 |
|  | Ex 6-5B | 36.0 |  |  |
| Ex 6-24 | Ex 6-4A | 37.0 | 36.0 | 28.5 |
|  | Ex 6-6B | 35.0 |  |  |
| Ex 6-25 | Ex 6-4A | 37.0 | 34.5 | 26.0 |
|  | Ex 6-7B | 32.0 |  |  |
| Ex 6-26 | Ex 6-5A | 35.0 | 37.8 | 26.0 |
|  | Ex 6-2B | 40.5 |  |  |
| Ex 6-27 | Ex 6-5A | 35.0 | 37.5 | 25.5 |
|  | Ex 6-3B | 40.0 |  |  |
| Ex 6-28 | Ex 6-5A | 35.0 | 36.8 | 24.0 |
|  | Ex 6-4B | 38.5 |  |  |
| Ex 6-29 | Ex 6-5A | 35.0 | 35.5 | 25.5 |
|  | Ex 6-5B | 36.0 |  |  |
| Ex 6-30 | Ex 6-5A | 35.0 | 35.0 | 24.5 |
|  | Ex 6-6B | 35.0 |  |  |
| Ex 6-31 | Ex 6-5A | 35.0 | 33.5 | 23.0 |
|  | Ex 6-7B | 32.0 |  |  |
| Ex 6-32 | Ex 6-6A | 33.5 | 37.0 | 27.0 |
|  | Ex 6-2B | 40.5 |  |  |
| Ex 6-33 | Ex 6-6A | 33.5 | 36.8 | 23.5 |
|  | Ex 6-3B | 40.0 |  |  |
| Ex 6-34 | Ex 6-6A | 33.5 | 36.0 | 24.5 |
|  | Ex 6-4B | 38.5 |  |  |
| Ex 6-35 | Ex 6-6A | 33.5 | 34.8 | 26.0 |
|  | Ex 6-5B | 36.0 |  |  |
| Ex 6-36 | Ex 6-6A | 33.5 | 34.3 | 24.0 |
|  | Ex 6-6B | 35.0 |  |  |
| Ex 6-37 | Ex 6-6A | 33.5 | 32.8 | 22.0 |
|  | Ex 6-7B | 32.0 |  |  |

*Staging behavior was not observed at given ratio of A/B and/or given concentration of A+ B Conclusion: Polyamine polyol and carboxylated polyamine polyols produced staging materials when paired an appropriate acid.

Example 7

This example demonstrates that the amine can be located on the surface of the filler.

The following A-Pastes were prepared by the following procedure.

A stock solution of bisGMA, TEGDMA, and bisEMA6 was prepared. Acid 10, CPQ and DPIHFP were dissolved in an aliquot of the stock solution. Once the resin was fully dissolved it was added to a mix cup. Then Filler 3 was added on top of the resin. The mixture was mixed (DAC 150, Flacteck Inc, Landrum SC) 3 cycles of 1 minute at 3000 rpm to produce paste. Table 7-1 gives the formulations.

TABLE 7-1

Acid Containing Formulations

| Ingredient | Ex 7-1A |
|---|---|
| Acid 10 | 7.05% |
| bisGMA | 11.44% |
| TEGDMA | 9.81% |
| BisEMA6 | 11.46% |
| CPQ | 0.08% |
| DPIHFP | 0.16% |
| Filler 3 | 60.00% |

The following B-Pastes were prepared by the following procedure.

Three separate resin blends were prepared. Resin blends either contained a blend of 70% wt bisGMA to 30% wt TEGDMA or a blend equal parts Procrylat, TEGDMA, bisEMA6 and 0.15% wt BHT, or a blend of 80% wt Procrylat to 20% wt DDDMA. Photo initiators were not added to these resins because only staging behavior was of interest. The resin was added to a mix cup. Then Filler 3 or Filler 4 was added on top of the resin. Once the resin was fully dissolved it was added to a mix cup. Then Filler 4 was added on top of the resin. The mixture was mixed (DAC 150, Flacteck Inc, Landrum SC) 3 cycles of 1 minute at 3000 rpm to produce paste. Table 7-2 gives the formulations.

TABLE 7-2

Basic Amine Containing Formulations

| | Formulation | | |
|---|---|---|---|
| | Ex 7-1B | Ex 7-2B | Ex 7-3B |
| bisGMA | 24.50% | — | — |
| TEGDMA | 10.49% | 11.64% | — |
| BisEMA6 | — | 11.64% | — |
| Procrylat | — | 11.64% | 27.99% |
| DDDMA | — | — | 7.00% |
| BHT | — | 0.05% | — |
| Filler 3 | — | — | — |
| Filler 4 | 65.01% | 65.03% | 65.01% |

Consistency was measured of individual A and B pastes. Then, aliquots of equal mass A was combined with Ex 7-1B, Ex 7-2B and Ex 7-3B, Table 7-3 shows the consistency of the individual pastes, and the consistency of the A+B paste.

TABLE 7-3

Resulting Consistency Upon Combining A + B Pastes

| Example | Paste | Individual consistency | Arithmetic mean consistency | Combined Consistency-Observed |
|---|---|---|---|---|
| Ex 7-1 | Ex 7-1A | 40 | 40 | 23.0 |
| | Ex 7-1B | 40 | | |
| Ex 7-2 | Ex 7-1A | 40 | 35 | 22.3 |
| | Ex 7-2B | 30 | | |
| Ex 7-3 | Ex 7-1A | 40 | 34 | 20.5 |
| | Ex 7-3B | 28 | | |

Conclusion: The basic amine surface treatment produced staging materials when paired an appropriate acid.

Example 8

The following A-Side Pastes were prepared by the following procedure.

A BHT stabilized stock solution of TEGDMA and bisEMA6 was prepared. The acid was then dissolved in an aliquot of the stock solution. Photo initiators were not added to these resins because only staging behavior was of interest. Once the resin was fully dissolved it was added to a mix cup. Then filler 3 and S/T 20 nmn silica were added on top of the resin. The mixture was mixed (DAC 150, Flacteck Inc, Landrum SC) 3 cycles of 1 minute at 3000 rpm to produce paste. Table 8-1 gives the formulations.

TABLE 8-1

Acid Containing Formulations

| | Formulation | |
|---|---|---|
| | EX 8-1A | Ex 8-2A |
| Inventive Acid | Acid 10 | Acid 10 |
| Acid | 6.88% | 10.44% |
| bisEMA6 | 19.64% | 17.17% |
| TEGDMA | 8.42% | 7.35% |
| BHT | 0.05% | 0.04% |
| Filler 3 | 58.51% | 58.50% |
| S/T 20 nm Silica | 6.50% | 6.50% |

The following B-Pastes were prepared by the following procedure.

A stock solution of bisGMA, TEGDMA and BHT was prepared. Photo initiators were not added to these resins because only staging behavior was of interest. The stock solution was added to the mix cup along with an acid surface treated zirconia. They were mixed for 1 min at 1500 rpm. Then Filler 3 and S/T 20 nm Silica was added on top of the resin. The components were mixed (DAC 150, Flacteck Inc, Landrum SC) 3 cycles of 1 minute at 3000 rpm to produce paste. Table 8-2 gives the formulations.

Preparation of Acid Surface Treated Zirconia Examples:
Zirconia 1:

7.498 g of mono-2-methacryloyloxyethyl succinate was dissolved into 100 g of isopropyl alcohol. This mixture was then added with vigorous stirring to 100 g of a 29.6% ZrO2 aqueous sol of 4-12 nm zirconia particles stabilized by acetic acid (zirconia particles prepared as described in U.S. Pat. No. 7,429,422 (Davidson et al), with 29.6% yttria modified zirconium oxide as solids).

After approximately 2 minutes of stirring, the sample was poured into a Pyrex tray and dried at 85 C for 1.5 hours to yield a dry solid.

Zirconia 2:

5.62 g of mono-2-methacryloyloxyethyl succinate was dissolved into 100 g of isopropyl alcohol. This mixture was then added with vigorous stirring to 100 g of a 29.6% ZrO2 aqueous sol of 4-12 nm zirconia particles stabilized by acetic acid (zirconia particles prepared as described in U.S. Pat. No. 7,429,422 (Davidson et al), with 29.6% yttria modified zirconium oxide as solids).

After approximately 2 minutes of stirring, the sample was poured into a Pyrex tray and dried at 85 C for 1.5 hours to yield a dry solid.

Zirconia 3:

1.87 g of mono-2-methacryloyloxyethyl succinate was dissolved into 100 g of isopropyl alcohol. This mixture was then added with vigorous stirring to 100 g of a 29.6% ZrO2 aqueous sol of 4-12 nm zirconia particles stabilized by acetic acid (zirconia particles prepared as described in U.S. Pat. No. 7,429,422 (Davidson et al), with 29.6% yttria modified zirconium oxide as solids).

After approximately 2 minutes of stirring, the sample was poured into a Pyrex tray and dried at 85 C for 1.5 hours to yield a dry solid.

TABLE 8-2

Modified Zirconia Particle 1:

|  | Ex 8-1B | Ex 8-2B | Ex 8-3B | Ex 8-4B |
|---|---|---|---|---|
| Zirconia 1 | 10.00% | 19.84% | 39.90% | 65.05% |
| bisGMA | 24.47% | 24.58% | 24.48% | 24.43% |
| TEGDMA | 10.48% | 10.54% | 10.49% | 10.47% |
| BHT | 0.05% | 0.05% | 0.05% | 0.05% |
| Filler 3 | 55.00% | 44.99% | 25.08% | 0.00% |

TABLE 8-3

Modified Zircoia Particle 2:

|  | Ex 8-5B | Ex 8-6B | Ex 8-7B | Ex 8-8B |
|---|---|---|---|---|
| Zirconia 2 | 9.86% | 19.95% | 40.05% | 64.98% |
| bisGMA | 24.56% | 24.49% | 24.38% | 24.48% |
| TEGDMA | 10.53% | 10.50% | 10.45% | 10.49% |
| BHT | 0.05% | 0.05% | 0.05% | 0.05% |
| Filler 3 | 55.00% | 45.01% | 25.07% | 0.00% |

TABLE 8-4

Modified Zircoia Particle 3:

|  | Ex 8-9B | Ex 8-10B | Ex 8-11B | Ex 8-12B |
|---|---|---|---|---|
| Zirconia 3 | 9.97% | 19.87% | 37.82% | 64.84% |
| sigma | 24.46% | 24.55% | 25.98% | 24.58% |
| TEGDMA | 10.48% | 10.52% | 11.13% | 10.53% |
| BHT | 0.05% | 0.05% | 0.05% | 0.05% |
| Filler 3 | 55.04% | 45.00% | 25.02% | 0.00% |

Consistency was measured of individual A and B pastes. Then, aliquots of equal mass A and B were combined. Table 8-5 shows the consistency of the individual pastes, and the consistency of the A+B paste.

TABLE 8-5

Resulting Consistency Upon Combining A + B Pastes

| Example | Paste | Individual consistency | Arithmetic mean consistency | Combined Consistency-Observed |
|---|---|---|---|---|
| Ex 8-1 | Ex 8-1A | 34.0 | 38.3 | 25.5 |
|  | Ex 8-1B | 42.5 |  |  |
| Ex 8-2 | Ex 8-1A | 34.0 | 37 | 20.5 |
|  | Ex 8-2B | 40.0 |  |  |
| Ex 8-3 | Ex 8-1A | 34.0 | 31.8 | 16.0 |
|  | Ex 8-3B | 29.5 |  |  |
| Ex 8-4 | Ex 8-1A | 34.0 | 28.5 | 13.0 |
|  | Ex 8-4B | 23.0 |  |  |
| Ex 8-5 | Ex 8-1A | 34.0 | 39.3 | 25.0 |
|  | Ex 8-5B | 44.5 |  |  |
| Ex 8-6 | Ex 8-1A | 34.0 | 39.0 | 21.5 |
|  | Ex 8-6B | 44.0 |  |  |
| Ex 8-7 | Ex 8-1A | 34.0 | 36.8 | 15.5 |
|  | Ex 8-7B | 39.5 |  |  |
| Ex 8-8 | Ex 8-1A | 34.0 | 33.0 | 12.5 |
|  | Ex 8-8B | 32.0 |  |  |
| Ex 8-9 | Ex 8-1A | 34.0 | 38.0 | 23.0 |
|  | Ex 8-9B | 42.0 |  |  |
| Ex 8-10 | Ex 8-1A | 34.0 | 38.8 | 20.0 |
|  | Ex 8-10B | 43.5 |  |  |
| Ex 8-11 | Ex 8-1A | 34.0 | 38.0 | 16.5 |
|  | Ex 8-11B | 42.0 |  |  |
| Ex 8-12 | Ex 8-1A | 34.0 | 33.3 | 12.5 |
|  | Ex 8-12B | 32.5 |  |  |
| Ex 8-13 | Ex 8-2A | 32.0 | 37.3 | 28.5 |
|  | Ex 8-1B | 42.5 |  |  |
| Ex 8-14 | Ex 8-2A | 32.0 | 36.0 | 24.0 |
|  | Ex 8-2B | 40.0 |  |  |
| Ex 8-15 | Ex 8-2A | 32.0 | 30.8 | 17.5 |
|  | Ex 8-3B | 29.5 |  |  |
| Ex 8-16 | Ex 8-2A | 32.0 | 27.5 | 13.0 |
|  | Ex 8-4B | 23.0 |  |  |
| Ex 8-17 | Ex 8-2A | 32.0 | 38.3 | 27.5 |
|  | Ex 8-5B | 44.5 |  |  |
| Ex 8-18 | Ex 8-2A | 32.0 | 38.0 | 22.5 |
|  | Ex 8-6B | 44.0 |  |  |
| Ex 8-19 | Ex 8-2A | 32.0 | 35.8 | 17.0 |
|  | Ex 8-7B | 39.5 |  |  |
| Ex 8-20 | Ex 8-2A | 32.0 | 32.0 | 13.0 |
|  | Ex 8-8B | 32.0 |  |  |
| Ex 8-21 | Ex 8-2A | 32.0 | 37.0 | 26.5 |
|  | Ex 8-9B | 42.0 |  |  |
| Ex 8-22 | Ex 8-2A | 32.0 | 37.8 | 21.0 |
|  | Ex 8-10B | 43.5 |  |  |
| Ex 8-23 | Ex 8-2A | 32.0 | 37.0 | 15.5 |
|  | Ex 8-11B | 42.0 |  |  |
| Ex 8-24 | Ex 8-2A | 32.0 | 32.3 | 12.5 |
|  | Ex 8-12B | 32.5 |  |  |

Conclusion: The mono-2-methacryloyloxyethyl succinate modified zirconia produced a staging material when paired with an appropriate acid.

Example 9

The following A-Side Pastes were prepared by the following procedure.

A BHT stabilized stock solution of TEGDMA and bisEMA6 was prepared. The acid was then dissolved in an aliquot of the stock solution. Once the resin was fully dissolved it was added to a mix cup along with CPQ and EDMAB. Then filler 3 and S/T 20 nmn silica were added on top of the resin. The mixture was mixed (DAC 150, Lactic Inc, Landrum SC) 3 cycles of 1 minute at 3000 rpm to produce paste. Table 9-1 gives the formulations.

TABLE 9-1

Acid Containing Formulations

| | Formulation |
|---|---|
| | EX 9-1A |
| Acid 10 | 7.00% |
| bisEMA6 | 19.31% |
| TEGDMA | 8.28% |
| BHT | 0.04% |
| CPQ | 0.01% |
| EDMAB | 0.36% |
| Filler 3 | 58.50% |
| S/T 20 nm Silica | 6.50% |

The following B-Pastes were prepared by the following procedure.

A stock solution of bisGMA, TEGDMA and BHT was prepared. The stock solution was added to the mix cup along with acid surface treated zirconia that was solvent exchanged into bisGMA/TEGDMA, CPQ and EDMAB. They were mixed for 1 min at 1500 rpm. Then Filler 3 and S/T 20 nm Silica was added on top of the resin. The components were mixed (DAC 150, Flacteck Inc, Landrum SC) 3 cycles of 1 minute at 3000 rpm to produce paste. Table 9-2 gives the formulations.

Preparation of Acid Surface Treated Zirconia Examples:

Zirconia 4:

4.63 g of carboxyethyl acrylate were dissolved in 120 g of 1-methoxy-2-propanol. This mixture was then added with vigorous stirring to 100 g of a 29.6% zirconia aqueous sol of 4-12 nm zirconia particles stabilized by acetic acid (zirconia particles prepared as described in U.S. Pat. No. 7,429,422 (Davidson et al), with 29.6% yttria modified zirconium oxide as solids). The alcohol/nanoparticle sol/surface modifier mixture was allowed to react for 1 hour. 22.858 g of a 50/50 weight mixture of bisGMA/TEGDMA was added to it and stirred to disperse/dissolve. Then the 1-methoxy-2-propanol and water were stripped from the system using a rotary evaporator until no more evidence of bubbling/solvent removal was observed.

Zirconia 5:

0.772 g of mono-2-methacryloyloxyethyl succinate and 7.274 g of 3-methacryloxypropyltrimethoxysilane were dissolved in 100 g of 1-methoxy-2-propanol.

This mixture was then added with vigorous stirring to 100 g of a 29.6% zirconia aqueous sol of 4-12 nm zirconia particles stabilized by acetic acid (zirconia particles prepared as described in U.S. Pat. No. 7,429,422 (Davidson et al), with 29.6% yttria modified zirconium oxide as solids).

The alcohol/nanoparticle sol/surface modifier mixture was heated to 85 C and allowed to react for 1 hour after reaching temperature on a rotary evaporator.

The sample was taken off heat and allowed to sit at room temperature for 2 days After this time, 23.65 g of a 5050 weight mixture of bisGMA/TEGDMA was added to it and stirred to disperse/dissolve. Then the 1-methoxy-2-propanol and water were stripped from the system using a rotary evaporator until no more evidence of bubbling/solvent removal was observed.

TABLE 9-2

Particle with Basic Surface Zircoia 4 and 5:

| | Formulation | | | | | |
|---|---|---|---|---|---|---|
| Modified Zirconia | EX 9-1B zirconia 4 | EX 9-2B zirconia 4 | EX 9-3B zirconia 4 | EX 9-4B zirconia 5 | EX 9-5B zirconia 5 | EX 9-6B zirconia 5 |
| Zirconia | 20.00% | 30.00% | 51.84% | 20.00% | 30.00% | 51.84% |
| bisGMA | 17.24% | 17.25% | 17.25% | 17.25% | 17.25% | 17.25% |
| TEGDMA | 17.24% | 17.25% | 17.25% | 17.25% | 17.25% | 17.25% |
| BHT | 0.05% | 0.05% | 0.05% | 0.05% | 0.05% | 0.05% |
| CPQ | 0.09% | 0.09% | 0.09% | 0.09% | 0.09% | 0.09% |
| EDMAB | 0.36% | 0.36% | 0.36% | 0.36% | 0.36% | 0.36% |
| Filler 3 | 40.52% | 31.50% | 11.84% | 40.50% | 31.50% | 11.84% |
| S/T 20 nm Silica | 4.50% | 3.50% | 1.32% | 4.50% | 3.50% | 1.32% |

Consistency was measured of individual A and B pastes. Then, aliquots of equal mass A and B were combined. Table 9-3 shows the consistency of the individual pastes, and the consistency of the A+B paste.

TABLE 9-3

Resulting Consistency Upon Combining A + B Pastes

| Example | Paste | Individual consistency | Arithmetic mean consistency | Combined Consistency-Observed |
|---|---|---|---|---|
| Ex 9-1 | Ex 9-1A | 31.0 | 41.3 | 22.0 |
| | Ex 9-1B | 51.5 | | |
| Ex 9-2 | Ex 9-1A | 31.0 | 41.0 | 19.5 |
| | Ex 9-2B | 51.0 | | |
| Ex 9-3 | Ex 9-1A | 31.0 | 37.5 | 15.0 |
| | Ex 9-3B | 44.0 | | |
| Ex 9-4 | Ex 9-1A | 31.0 | 41.8 | 33.0 |
| | Ex 9-4B | 52.5 | | |
| Ex 9-5 | Ex 9-1A | 31.0 | 41.5 | 26.5 |
| | Ex 9-5B | 52.0 | | |
| Ex 9-6 | Ex 9-1A | 31.0 | 34.8 | 19.0 |
| | Ex 9-6B | 38.5 | | |

Conclusion: Zirconia surface modified with carboxyethyl acrylate or a combination of mono-2-methacryloyloxyethyl succinate and 3-methacryloxypropyltrimethoxysilane produced a material that staged when combined with an appropriate acid.

Example 10

The following A-Side Pastes were prepared by the following procedure.

A BHT stabilized stock solution of TEGDMA and bisEMA6 was prepared. The acid was then dissolved in an aliquot of the stock solution. Initiators were omitted from this formulation because only staging behavior was of interest. Then filler 3 and S/T 20 nmn silica were added on top of the resin. The mixture was mixed (DAC 150, Lactic Inc, Landrum SC) 3 cycles of 1 minute at 3000 rpm to produce paste. Table 10-1 gives the formulations.

TABLE 10-1

Acid Containing Formulations

| | Formulation |
|---|---|
| | EX 10-1A |
| Acid 10 | 7.00% |
| bisEMA6 | 19.56% |
| TEGDMA | 8.40% |
| BHT | 0.04% |
| Filler 3 | 58.50% |
| S/T 20 nm Silica | 6.50% |

The following B-Pastes were prepared by the following procedure.

A stock solution of bisGMA, TEGDMA and BHT was prepared. The stock solution was added to the mix cup along with acid surface treated zirconia that was solvent exchanged into bisGMA/TEGDMA. They were mixed for 1 min at 1500 rpm. Then Filler 3 and S/T 20 nm Silica was added on top of the resin. The components were mixed (DAC 150, Flacteck Inc. Landrum SC) 3 cycles of 1 minute at 3000 rpm to produce paste. Table 10-2 gives the formulations.

Preparation of Acid Surface Treated Zirconia Examples:

Zirconia 6:

100.0 g Acid reduced ZrO2 sol (29.6% solids) was weighed into a mixing vessel and Mixed with a mixture of 100 g 1-methoxy-2-propanol and 6.006 g mono-2-methacryloyloxyethyl succinate and 3.024 g methacryloyloxyhexyl phosphate. This mixture was stirred to allow to react the acids to the zirconia surface. To this mixture was added 23.592 g of a 50/50 weight % BisGMA/TEGDMA mixture. The material was then stripped on a rotovap to remove the solvent and water and gave an opalescent dispersion.

Zirconia 7:

100 g acid reduced ZrO2 sol (29.6% solids) was weighed into a mixing vessel and mixed with 2.251 g mono-2-methacryloyloxyethyl succinate and 50 g 1-methoxy-2-propanol. To this was added a mixture of 10.636 g methacryloyloxyhexyl phosphate and 50 g 1-methoxy-2-propanol. Finally, a mixture of 20.72 g 50/50 weight % BisGMA/TEGDMA was added. The material was then stripped on a rotovap to remove solvent and water.

TABLE 10-2

Particle with Basic Surface Zircoia 6 and 7:

| | Formulation | | | | | |
|---|---|---|---|---|---|---|
| Modified Zirconia | EX 10-1B zirconia 6 | EX 10-2B zirconia 6 | EX 10-3B zirconia 6 | EX 10-4B zirconia 7 | EX 10-5B zirconia 7 | EX 10-6B zirconia 7 |
| Zirconia | 20.00% | 30.00% | 51.84% | 20.00% | 30.00% | 51.84% |
| bisGMA | 17.46% | 17.46% | 17.46% | 17.46% | 17.46% | 17.46% |
| TEGDMA | 17.46% | 17.46% | 17.46% | 17.46% | 17.46% | 17.46% |
| BHT | 0.05% | 0.05% | 0.05% | 0.05% | 0.05% | 0.05% |
| Filler 3 | 40.53% | 31.53% | 11.87% | 40.53% | 31.53% | 11.87% |
| S/T 20 nm Silica | 4.50% | 3.50% | 1.32% | 4.50% | 3.50% | 1.32% |

Consistency was measured of individual A and B pastes. Then, aliquots of equal mass A and B were combined. Table 10-3 shows the consistency of the individual pastes, and the consistency of the A+B paste.

TABLE 10-3

Resulting Consistency Upon Combining A + B Pastes

| Example | Paste | Individual consistency | Arithmetic mean consistency | Combined Consistency-Observed |
|---|---|---|---|---|
| Ex 10-1 | Ex 10-1A | 30.0 | 44.0 | 26.5 |
| | Ex 10-1B | 58.0 | | |
| Ex 10-2 | Ex 10-1A | 30.0 | 43.5 | 23.8 |
| | Ex 10-2B | 57.0 | | |
| Ex 10-3 | Ex 10-1A | 30.0 | 43.5 | 18.0 |
| | Ex 10-3B | 57.0 | | |
| Ex 10-4 | Ex 10-1A | 30.0 | 42.5 | 37.0 |
| | Ex 10-4B | 55.0 | | |
| Ex 10-5 | Ex 10-1A | 30.0 | 41.5 | 31.5 |
| | Ex 10-5B | 53.0 | | |
| Ex 10-6 | Ex 10-1A | 30.0 | 44.0 | 25.0 |
| | Ex 10-6B | 58.0 | | |

Conclusion: Zirconia surface modified with a combination of mono-2-methacryloyloxyethyl succinate and methacryloyloxyhexyl phosphate produced a material that staged when combined with an appropriate acid.

Example 11

In a 2-part system where the actives interact to form a new state the A and B materials must be considered in 2 dimensions: the concentration of A+B and the ratio A/B.

Both will have an impact on the state of the material when combined.

The following example illustrates the impact of molar equivalence of acid or amine concentration and the ratio of A/B in a system staged with an acid and basic amine.

The following A-Pastes were prepared by the following procedure.

A stock solution of equal parts Procrylat, TEGDMA, and bisEMA6 was prepared. Acid 10, CPQ, DPIHFP, and EDMAO were dissolved in an aliquot of the stock solution. Once the resin was fully dissolved it was added to a mix cup. Then Filler 1 was added on top of the resin. The mixture was mixed (DAC 150, Flacteck Inc, Landrum SC) 3 cycles of 1 minute at 3000 rpm to produce paste. Table 11-1 gives the formulations.

TABLE 11-1

Acid Containing Formulations

| Formulation | Ex 11-1A | Ex 11-2A | Ex 11-3A | Ex 11-4A | Ex 11-5A | Ex 11-6A | Ex 11-7A | Ex 11-8A | Ex 11-9A |
|---|---|---|---|---|---|---|---|---|---|
| Acid 10 | 3.50% | 5.25% | 7.00% | 8.74% | 4.13% | 4.65% | 5.32% | 5.73% | 4.85% |
| Procrylat | 10.41% | 9.83% | 9.25% | 8.67% | 10.19% | 10.04% | 10.08% | 9.66% | 9.97% |
| TEGDMA | 10.41% | 9.83% | 9.25% | 8.67% | 10.19% | 10.04% | 10.08% | 9.66% | 9.97% |
| bisEMA6 | 10.41% | 9.83% | 9.25% | 8.67% | 10.19% | 10.04% | 10.08% | 9.66% | 9.97% |
| CPQ | 0.07% | 0.07% | 0.07% | 0.07% | 0.07% | 0.07% | 0.07% | 0.07% | 0.07% |
| DPIHFP | 0.14% | 0.14% | 0.14% | 0.14% | 0.14% | 0.14% | 0.14% | 0.14% | 0.14% |
| EDMOA | 0.05% | 0.05% | 0.05% | 0.05% | 0.05% | 0.05% | 0.05% | 0.05% | 0.05% |
| Filler 1 | 65.01% | 65.00% | 64.99% | 64.99% | 65.04% | 64.97% | 64.18% | 65.03% | 64.98% |

The following B-Pastes were prepared by the following procedure.

A stock solution of equal parts Procrylat, TEGDMA, and bisEMA6 was prepared. Amine 8, CPQ, EDMAB, and EDMAO were dissolved in an aliquot of the stock solution. Once the resin was fully dissolved it was added to a mix cup. Then Filler 1 was added on top of the resin. The mixture was mixed (DAC 150, Flacteck Inc, Landrum SC) 3 cycles of 1 minute at 3000 rpm to produce paste. Formulation Table 11-2 gives the formulations.

TABLE 11-2

Basic Amine Containing Formulations

| Formulations | Ex 11-1B | Ex 11-2B | Ex 11-3B | Ex 11-4B | Ex 11-5B | Ex 11-6B | Ex 11-7B | Ex 11-8B | Ex 11-9B |
|---|---|---|---|---|---|---|---|---|---|
| Amine 8 | 3.50% | 5.25% | 7.00% | 8.74% | 8.43% | 7.86% | 7.38% | 6.59% | 7.63% |
| Procrylat | 10.23% | 9.64% | 9.06% | 8.48% | 8.57% | 8.76% | 8.95% | 9.19% | 8.86% |
| TEGDMA | 10.23% | 9.64% | 9.06% | 8.48% | 8.57% | 8.76% | 8.95% | 9.19% | 8.86% |
| bisEMA6 | 10.23% | 9.64% | 9.06% | 8.48% | 8.57% | 8.76% | 8.95% | 9.19% | 8.86% |
| CPQ | 0.07% | 0.07% | 0.07% | 0.07% | 0.07% | 0.07% | 0.07% | 0.07% | 0.07% |
| EDMAB | 0.70% | 0.70% | 0.70% | 0.70% | 0.70% | 0.70% | 0.70% | 0.70% | 0.70% |
| EDMOA | 0.05% | 0.05% | 0.05% | 0.05% | 0.05% | 0.05% | 0.05% | 0.05% | 0.05% |
| Filler 1 | 64.99% | 65.01% | 65.00% | 65.00% | 65.04% | 65.04% | 64.95% | 65.02% | 64.97% |

A-side and the corresponding B-side (Ex 11-1A-+Ex 11-1B, Ex 11-2A+Ex 11-2B, etc.) pastes were hand mixed 1:1 by mass. Stage Rank was determined.

The concentration of A+B expressed in mmol/g (total formulation) were calculated. The ratio of A/B in mol/mol acid to base (amine) equivalence (poly acid & poly base) were calculated. Results Table 11-3 shows minimum A+B concentration to stage, and a range of A/B ratios that are acceptable.

TABLE 11-3

Resulting Consistency and Stage Rank Upon Combining A + B Pastes

| A Paste | B Paste | A + B mmol/g total | A/B (mol/mol equiv) | Stage Rank |
|---|---|---|---|---|
| Ex 11-1A | Ex 11-1B | 0.09 | 1.15 | 1.0 |
| Ex 11-1A | Ex 11-2B | 0.11 | 0.78 | 2.0 |
| Ex 11-1A | Ex 11-3B | 0.13 | 0.57 | 2.0 |
| Ex 11-1A | Ex 11-4B | 0.15 | 0.45 | 2.0 |
| Ex 11-2A | Ex 11-1B | 0.11 | 1.73 | 3.0 |
| Ex 11-2A | Ex 11-2B | 0.13 | 1.16 | 3.0 |
| Ex 711-2A | Ex 11-3B | 0.15 | 0.88 | 3.5 |
| Ex 11-2A | Ex 11-4B | 0.17 | 0.68 | 4.0 |
| Ex 11-3A | Ex 11-1B | 0.13 | 2.30 | 4.0 |
| Ex 11-3A | Ex 11-2B | 0.16 | 1.54 | 4.0 |
| Ex 11-3A | Ex 11-3B | 0.18 | 1.17 | 4.0 |
| Ex 11-3A | Ex 11-4B | 0.20 | 0.93 | 4.0 |
| Ex 11-4A | Ex 11-1B | 0.16 | 2.88 | 4.0 |

TABLE 11-3-continued

Resulting Consistency and Stage Rank Upon Combining A + B Pastes

| A Paste | B Paste | A + B mmol/g total | A/B (mol/mol equiv) | Stage Rank |
|---|---|---|---|---|
| Ex 11-4A | Ex 11-2B | 0.18 | 1.91 | 4.0 |
| Ex 11-4A | Ex 11-3B | 0.20 | 1.42 | 4.0 |
| Ex 11-4A | Ex 11-4B | 0.22 | 1.15 | 4.0 |
| Ex 11-5A | Ex 11-5B | 0.15 | 0.56 | 2.0 |
| Ex 11-6A | Ex 11-6B | 0.15 | 0.68 | 2.5 |
| Ex 11-7A | Ex 11-7B | 0.16 | 0.82 | 3.0 |
| Ex 11-8A | Ex 11-8B | 0.15 | 1.00 | 4.0 |
| Ex 11-9A | Ex 11-9B | 0.15 | 0.73 | 3.0 |

Conclusion: For this acid/base pair combo, in the given resin system, the results indicate a minimum of the sum of the active ingredients of about 0.1 mmol/g and an effective ratio range of about 0.4 to 3.

Example 12

The following A-Side Pastes were prepared by the following procedure.

A BHT stabilized stock solution of TEGDMA and bisEMA6 was prepared. The acid was then dissolved in an aliquot of the stock solution. Initiators were omitted from this formulation because only staging behavior was of interest. Then filler 3 and S/T 20 nmn silica were added on top of the resin. The mixture was mixed (DAC 150, Lactic Inc, Landrum SC) 3 cycles of 1 minute at 3000 rpm to produce paste. Table 12-1 gives the formulations.

TABLE 12-1

Acid Containing Formulations

| | Formulation |
|---|---|
| | EX 12-1A |
| Acid 10 | 7.00% |
| bisEMA6 | 19.56% |
| TEGDMA | 8.40% |
| BHT | 0.04% |
| Filler 3 | 58.50% |
| S/T 20 nm Silica | 6.50% |

The following B-Pastes were prepared by the following procedure.

A stock solution of 70% bisGMA and 30% TEGDMA was prepared. The stock solution was added to the mix cup along with the calcium salt that was prepared in bisGMA/TEGDMA. They were mixed for 1 min at 1500 rpm. Then Filler 3 and S/T 20 nm Silica was added on top of the resin. The components were mixed (DAC 150, Flacteck Inc, Landrum SC) 3 cycles of 1 minute at 3000 rpm to produce paste. Table 12-2 gives the formulations.

Calcium Salt 1:

2.468 g of calcium hydroxide (Sigma-Aldrich, CAS 1305-62-0) was weighed into a mixing vessel and mixed with 15.338 g mono-2-(methacryloyloxy)ethyl succinate (Sigma-Aldrich, CAS 20882-04-6) and 7.631 g of bisGMA and 7.632 g of TEGDMA. The resulting mixture was a clear liquid.

Calcium Salt 2:

2.110 g of calcium hydroxide (Sigma-Aldrich, CAS 1305-62-0) was weighed into a mixing vessel and mixed with 13.045 g mono-2-(methacryloyloxy)ethyl maleate (Sigma-Aldrich, CAS 51978-15-5) and 7.014 g of bisGMA and 7.021 g of TEGDMA. The resulting mixture was a clear liquid.

TABLE 12-2

Basic Amine Containing Formulations

| | Formulations | |
|---|---|---|
| | Ex 12-1B | Ex 12-2B |
| Salt | Calcium Salt 1 | Calcium Salt 2 |
| Salt | 1.5035 g | 1.5043 g |
| 70% BisGMA/30% TEGDMA stock | 1.7942 g | 1.6733 g |
| Filler 3 | 3.5835 g | 3.4521 g |
| S/T 20 nm Silica | 0.3982 g | 0.3836 g |

Consistency was measured of individual A and B pastes. Then, aliquots of equal mass A and B were combined. Table 12-3 shows the consistency of the individual pastes, and the consistency of the A+B paste.

TABLE 12-3

Resulting Consistency Upon Combining A + B Pastes

| Example | Paste | Individual consistency | Arithmetic mean consistency | Combined Consistency-Observed |
|---|---|---|---|---|
| Ex 12-1 | Ex 12-1A | 37.5 | 34.3 | 18.5 |
| | Ex 12-1B | 31.0 | | |
| Ex 12-2 | Ex 12-1A | 37.5 | 37.0 | 18.5 |
| | Ex 12-2B | 36.5 | | |

Conclusion: Salts of calcium and mono-2-(methacryloyloxy)ethyl succinate or mono-2-(methacryloyloxy)ethyl maleate produced a material that staged when combined with an appropriate acid.

All cited references, patents, or patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A non-aqueous composition comprising:
a flowable Part A comprising at least one resin and Reactant A, and is characterized by a flowable Part A consistency,
Reactant A is:
an organic acid,
an organic acid comprising (meth)acrylate functionality, or
a metal oxide surface-treated with an organic acid;
a flowable Part B comprising at least one resin and Reactant B, and is characterized by a flowable Part B consistency,
Reactant B is:
an organic amine comprising (meth)acrylate functionality or derived from an organic amine comprising (meth)acrylate functionality, or
a metal oxide surface-treated with an amine functionalized silane; and a free radical initiator system within one or more of flowable Part A and flowable Part B;

wherein one or more of the at least one resin is a free radical polymerizable resin;

wherein when flowable Part A and flowable Part B are mixed in first step to provide a flowable mixed composition:

Reactant A and Reactant B react in an acid-base reaction to form a conjugate ion pair within a first staging time, and the flowable mixed composition is characterized by a first staged stable consistency, the first staged stable consistency having a value lower than the arithmetic mean of the flowable Part A consistency and the flowable Part B consistency; and wherein when free radical polymerization is initiated in a second step, one or more of the at least one resin, Reactant A, and Reactant B polymerizes to form a hardened composition suitable as a hardened dental composition.

2. The non-aqueous composition of claim 1, wherein at least one of flowable Part A and flowable Part B, further comprises 10 wt.-% to 90 wt.-% inorganic filler.

3. The non-aqueous composition of claim 1, wherein the free radical initiator system comprises a photoinitiator system or a redox initiator system.

4. The non-aqueous composition of claim 1, wherein consistency of the mixed composition having the first staged stable consistency changes no more than 20 percent over 30 minutes.

5. The non-aqueous composition of claim 1, wherein the first staging time is 5 seconds to 5 minutes.

6. The non-aqueous composition of claim 1, wherein:

Reactant A is the organic acid or the the organic acid comprising the (meth)acrylate functionality, and Reactant B is the organic amine comprising the (meth)acrylate functionality.

7. The non-aqueous composition of claim 1, wherein Reactant B is the organic amine comprising the (meth)acrylate functionality.

8. The non-aqueous composition of claim 1, wherein the Reactant A and the Reactant B are present in the composition at an equivalent ratio of 5:1 to 1:5 (acid to base).

9. The non-aqueous composition of claim 1, wherein Reactant B is the metal oxide surface-treated with an amine functionalized silane.

10. The non-aqueous composition of claim 9, wherein the metal oxide comprises Zirconia, Alumina, Yttria, Titania, Ceria, Zinc Oxide, Aluminosilicates, doped Aluminosilicates or combinations thereof.

11. A method of preparing a composition having a first staged stable consistency, the method comprising:

providing a non-aqueous composition according to claim 1;

mixing flowable Part A and flowable Part B to provide a flowable mixed composition; and allowing the consistency of the flowable composition to decrease to a first staged stable consistency that is lower than the arithmetic mean of the flowable Part A consistency and the flowable Part B consistency.

12. A method of preparing a hardened dental composition, the method comprising:

providing a non-aqueous composition according to claim 1;

mixing flowable Part A and flowable Part B to provide a flowable mixed composition;

allowing the consistency of the flowable mixed composition to decrease to a first staged stable consistency that is lower than the arithmetic mean of the flowable Part A consistency and the flowable Part B consistency; and subjecting the flowable mixed composition having the first staged stable consistency to conditions sufficient to initiate free radical polymerization to provide the hardened dental composition.

13. The method of claim 11, wherein mixing flowable Part A and flowable Part B comprises dispensing each part from a unit dose device through a static mixing device.

14. The method of claim 12, wherein conditions sufficient to initiate free radical polymerization are selected from the group consisting of irradiation, heat, and combinations thereof.

15. The method of claim 11, wherein the mixed composition having the first staged stable consistency forms a transient dental filling, a transient dental inlay, a transient dental onlay, a transient dental crown, a transient dental bridge, a transient denture, a transient dental appliance, or a combination thereof, and wherein the hardened dental composition forms a dental filing, a dental inlay, a dental onlay, a dental crown, a dental bridge, a denture, a dental applicant, or a combination thereof.

16. A device for storing a non-aqueous composition according to claim 1 comprising:

a first compartment containing flowable Part A; and a second compartment containing flowable Part B.

17. The device of claim 16, wherein both the first compartment and the second compartment each independently comprises a nozzle or an interface for receiving an entrance orifice of a static mixing tip.

18. The non-aqueous composition of claim 9, wherein the metal oxide is a silica-zirconia nanocluster filler.

19. The non-aqueous composition of claim 1, wherein Reactant A is selected from:

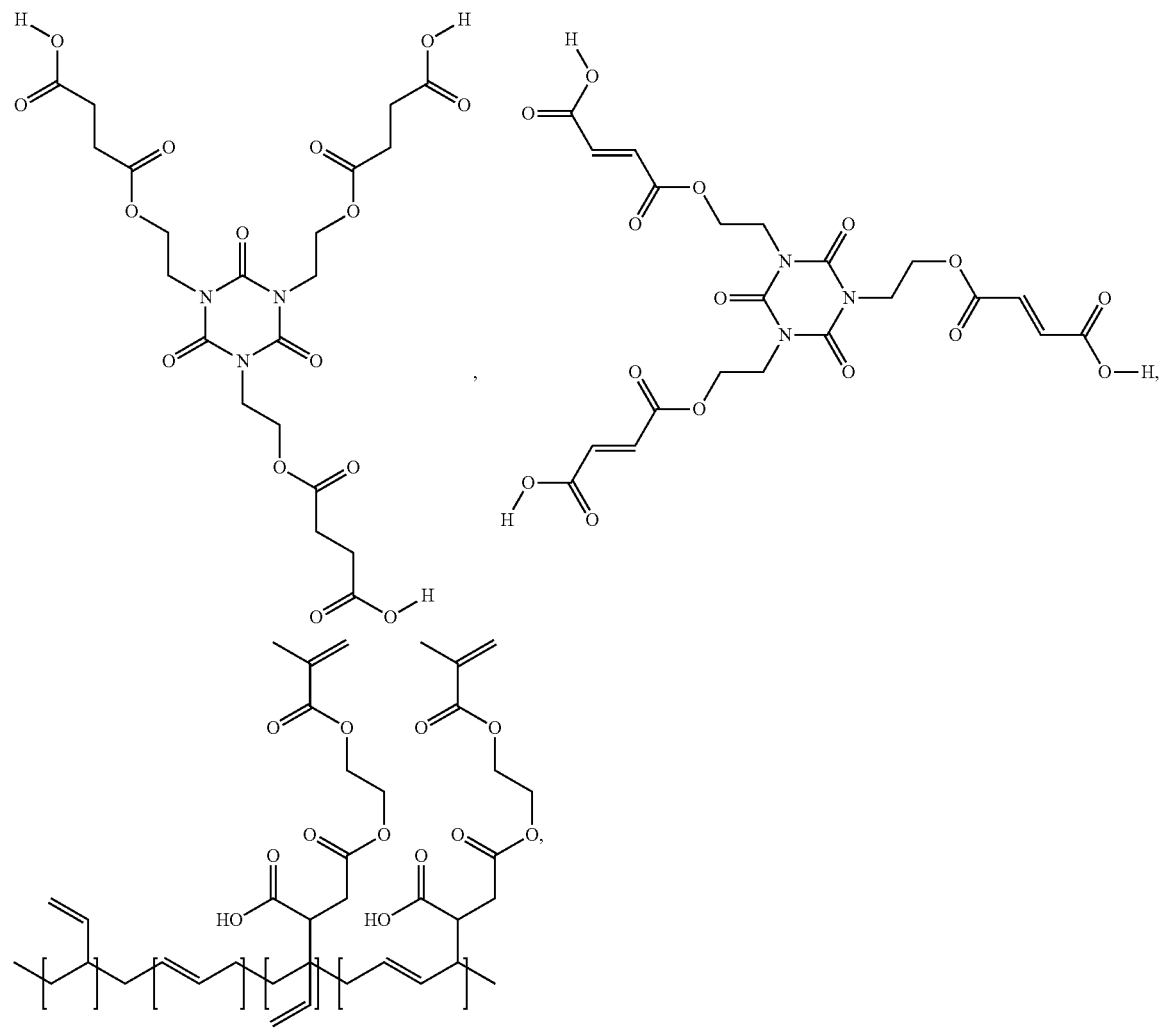
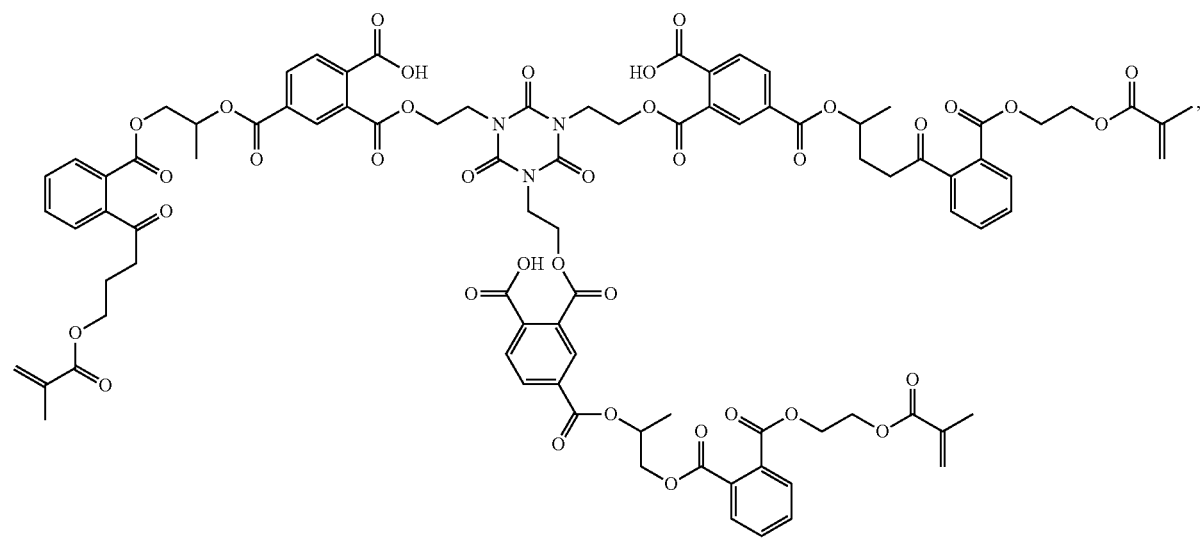

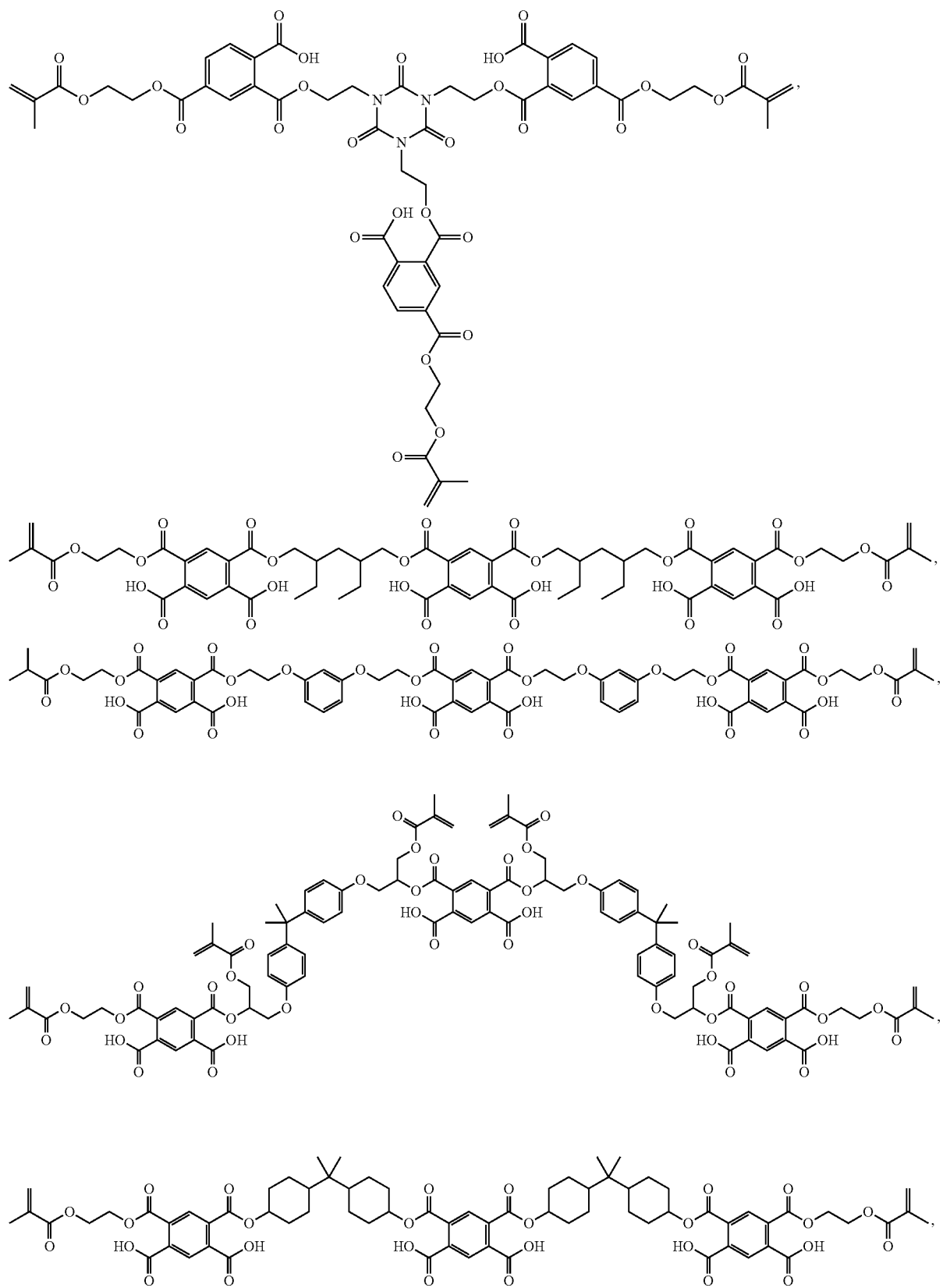

-continued
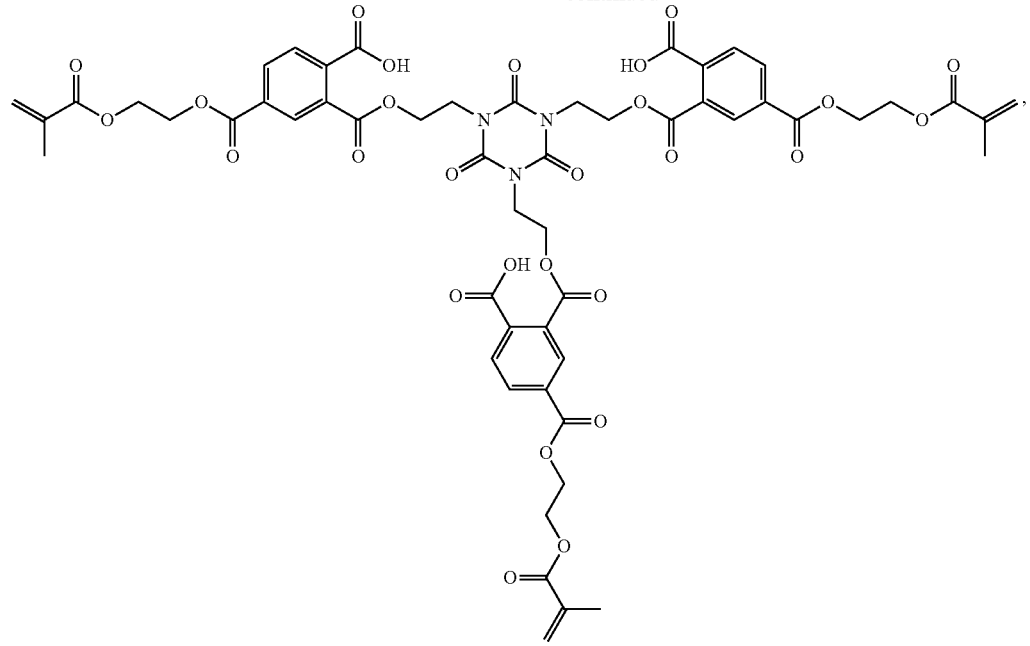
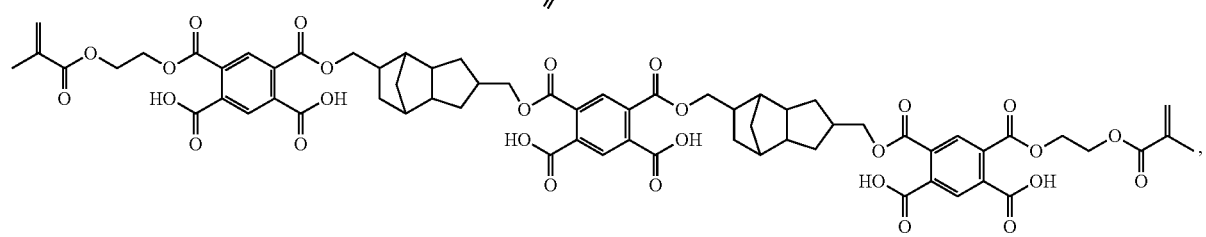
and
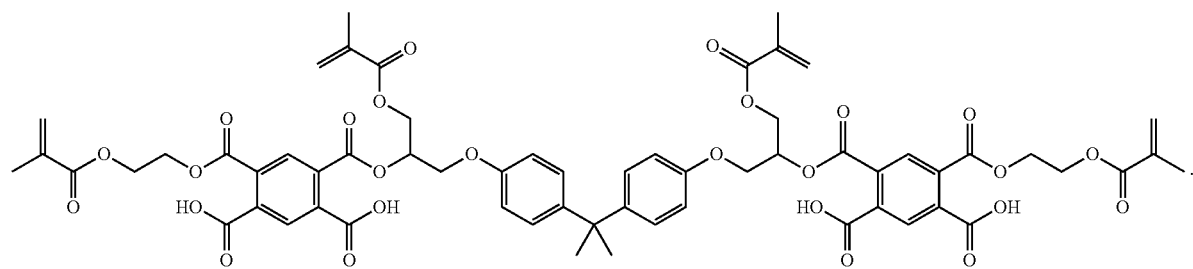
20. The non-aqueous composition of claim 1, wherein Reactant B is selected from:
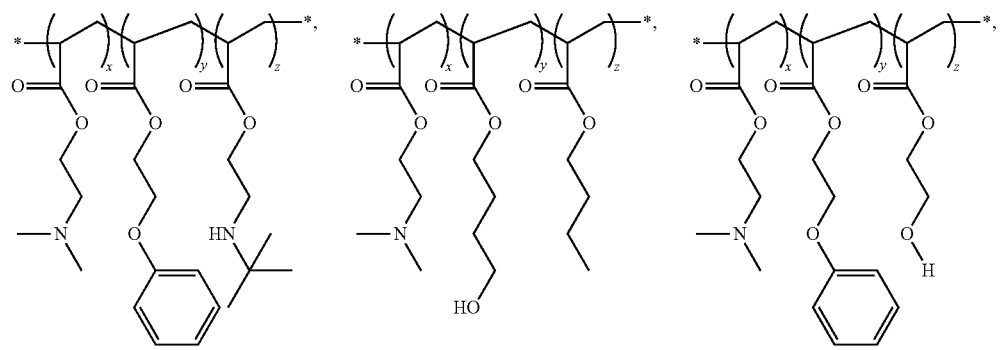

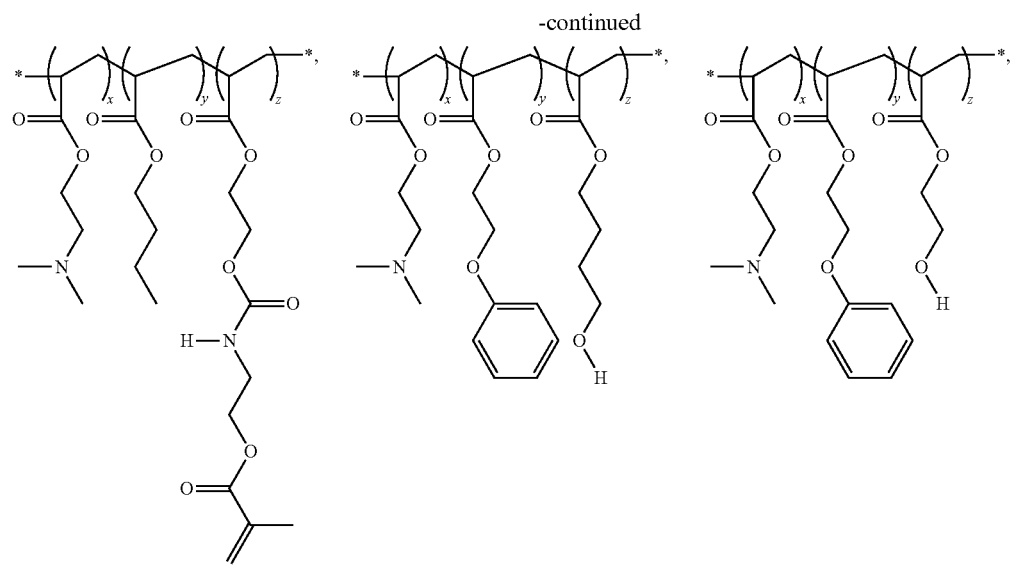
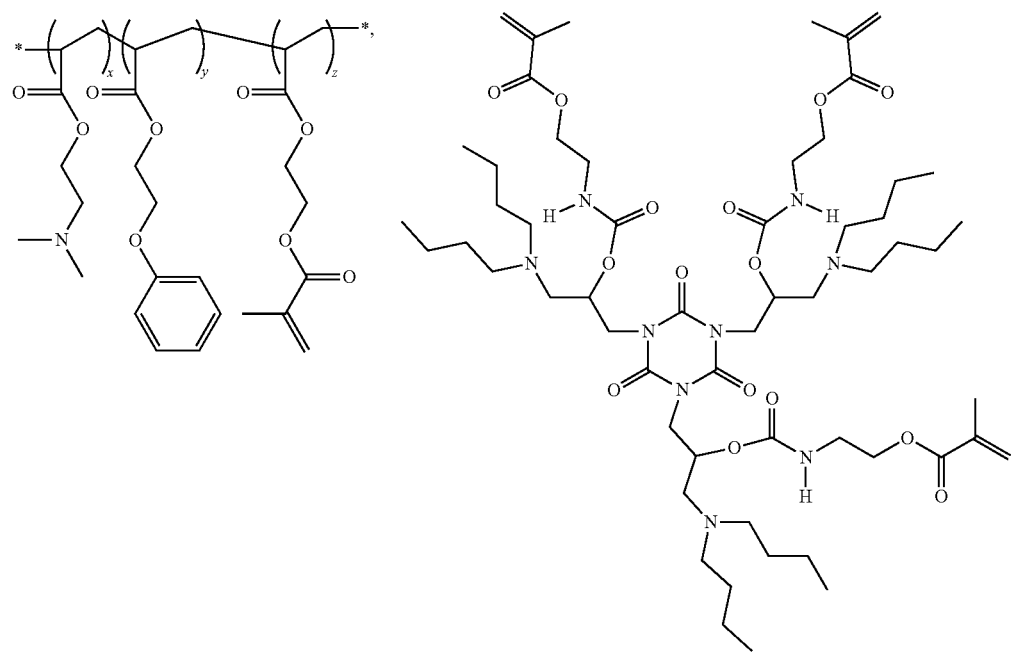

-continued
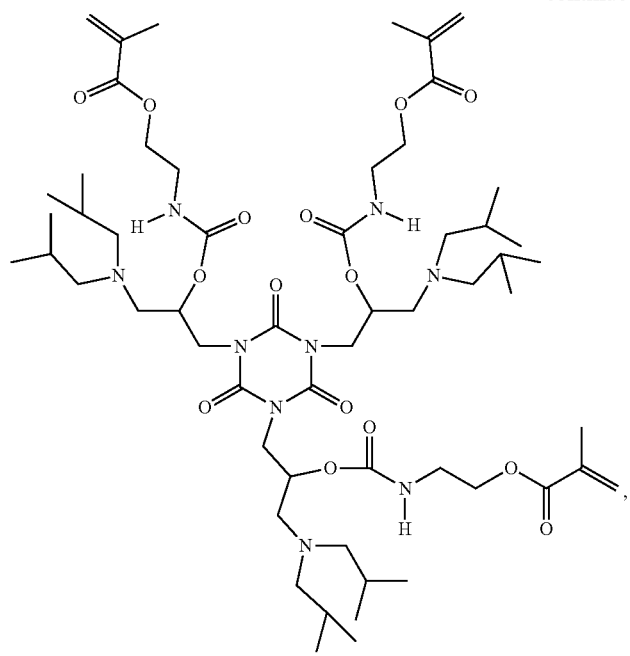
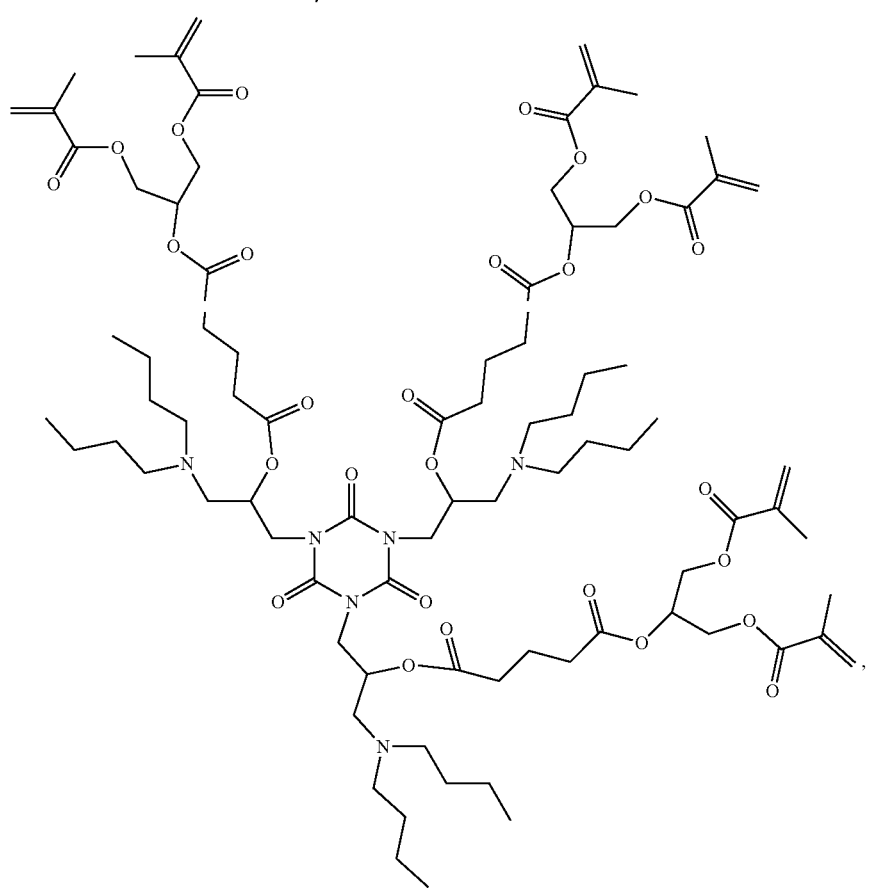
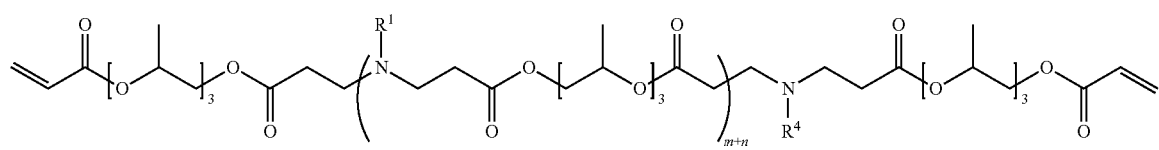

wherein:
R$^1$ and R$^2$ are selected from —CH$_2$CH$_2$CH$_2$CH$_3$ and —CH$_2$CH$_2$OH; and
m+n=9, m corresponds to when R$^3$ is —CH$_2$CH$_2$CH$_2$CH$_3$, and n corresponds to when R$^3$ is —CH$_2$CH$_2$OH,
when R$^1$ and R$^2$ is —CH$_2$CH$_2$CH$_2$CH$_3$, then m is 5,
when R$^1$ is —CH$_2$CH$_2$CH$_2$CH$_3$ and R$^2$ is —CH$_2$CH$_2$OH, then m is 6, and

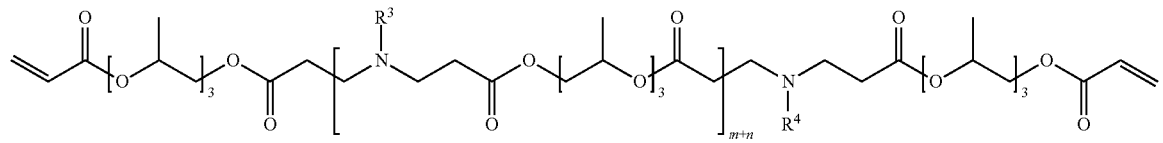

wherein:
R$^3$ and R$^4$ are selected from —CH$_2$CH$_2$OH, and —CH$_2$CH$_2$OC(O)CH$_2$CH$_2$C(O)OH;
m+n=9, m corresponds to when R$^3$ is —CH$_2$CH$_2$CH$_2$CH$_3$, and n corresponds to when R$^3$ is —CH$_2$CH$_2$OH or —CH$_2$CH$_2$OC(O)CH$_2$CH$_2$C(O)OH,
when R$^3$ and R$^4$ is —CH$_2$CH$_2$CH$_2$CH$_3$, then m is 5,
when R$^3$ is —CH$_2$CH$_2$CH$_2$CH$_3$ and R$^4$ is —CH$_2$CH$_2$OH or —H$_2$CH$_2$OC(O)CH$_2$CH$_2$C(O)OH, then m is 6.

* * * * *

UNITED STATES PATENT AND TRADEMARK OFFICE
CERTIFICATE OF CORRECTION

PATENT NO. : 11,793,731 B2
APPLICATION NO. : 16/954726
DATED : October 24, 2023
INVENTOR(S) : Gregory A. Kobussen Page 1 of 2

It is certified that error appears in the above-identified patent and that said Letters Patent is hereby corrected as shown below:

In the Claims

Column 90

Line 60 (approx.), In Claim 20, delete " 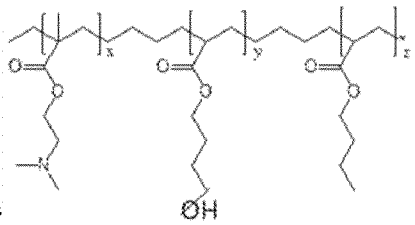 " and insert

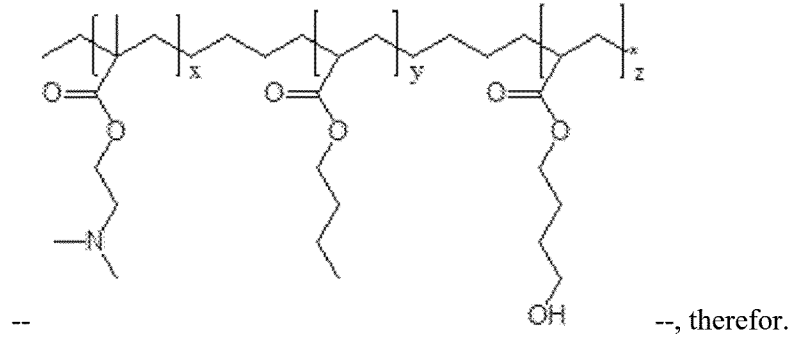 --, therefor.

Signed and Sealed this
Sixth Day of August, 2024

Katherine Kelly Vidal
Director of the United States Patent and Trademark Office

CERTIFICATE OF CORRECTION (continued)
U.S. Pat. No. 11,793,731 B2

Column 93

Line 1 (approx.), In Claim 20, delete " 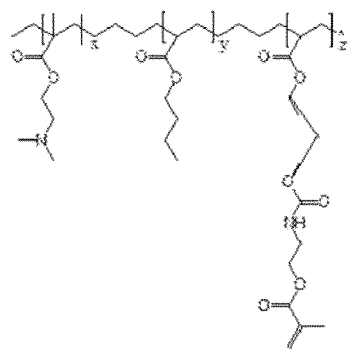 " and insert

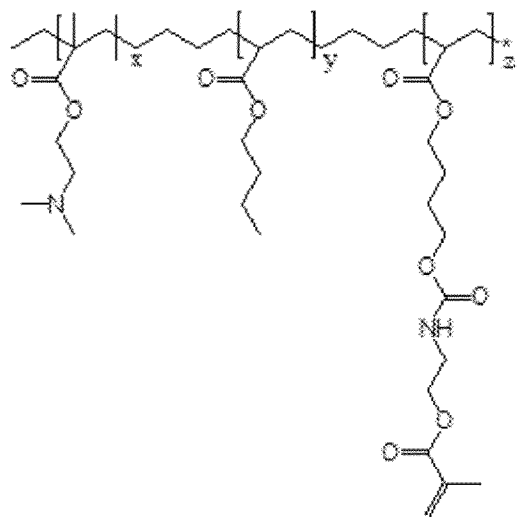

-- --, therefor.

Column 97
Line 4, In Claim 20, delete "m corresponds to when $R^3$ is" and insert -- m corresponds to when $R^1$ is --, therefor.
Line 5-6, In Claim 20, delete "n corresponds to when $R^3$ is" and insert -- n corresponds to when $R^1$ is --, therefor.